United States Patent
Liu et al.

(10) Patent No.: US 12,398,139 B2
(45) Date of Patent: Aug. 26, 2025

(54) MODULATORS OF AMPA RECEPTOR SIGNALING

(71) Applicants: Centre for Addiction and Mental Health, Toronto (CA); The University Court of the University of Aberdeen, Aberdeen (GB)

(72) Inventors: Fang Liu, Toronto (CA); Iain Greig, Aberdeen (GB); Dongxu Zhai, Toronto (CA); Stephen Allan Smith, London (GB); Chiara Zanato, Aberdeen (GB); Chih-Chung Tseng, Aberdeen (GB)

(73) Assignees: Centre for Addiction and Mental Health, Toronto (CA); The University Court of the University of Aberdeen, Aberdeen (GB)

( * ) Notice: Subject to any disclaimer, the term of this patent is extended or adjusted under 35 U.S.C. 154(b) by 938 days.

(21) Appl. No.: 17/310,996

(22) PCT Filed: Mar. 5, 2020

(86) PCT No.: PCT/IB2020/051920
§ 371 (c)(1),
(2) Date: Sep. 3, 2021

(87) PCT Pub. No.: WO2020/178782
PCT Pub. Date: Sep. 10, 2020

(65) Prior Publication Data
US 2022/0185813 A1 Jun. 16, 2022

Related U.S. Application Data

(60) Provisional application No. 62/814,076, filed on Mar. 5, 2019.

(51) Int. Cl.
*C07D 487/04* (2006.01)
*A61P 25/00* (2006.01)

(52) U.S. Cl.
CPC ............ *C07D 487/04* (2013.01); *A61P 25/00* (2018.01)

(58) Field of Classification Search
CPC .................................................. C07D 487/04
See application file for complete search history.

(56) References Cited

U.S. PATENT DOCUMENTS

| 2013/0336951 A1 | 12/2013 | Liu |
| 2015/0284411 A1 | 10/2015 | Apgar |
| 2018/0099940 A1 * | 4/2018 | Crew .................. A61K 31/501 |

FOREIGN PATENT DOCUMENTS

| WO | 2013102265 A1 | 7/2013 | |
| WO | WO-2014031515 A1 * | 2/2014 | ........... A61K 31/366 |
| WO | 2018080917 A1 | 5/2018 | |

OTHER PUBLICATIONS

Phillips et al., "Spina Bifida Management", 2017, 47, pp. 173-177Curr Probl Pediatr Adolesc Health Care, 47, pp. 173-177 (Year: 2017).*
Gulati et al., "Cerebral Palsy: An Overview", 2018, Indian J Pediatr, 85, pp. 1006-1016 (Year: 2018).*
Scheltens et al., "Alzheimer's disease", 2016, The Lancet, 388, pp. 505-517 (Year: 2016).*
De Strooper et al., "The Cellular Phase of Alzheimer's Disease", 2016, Cell, 164, pp. 603-615 (Year: 2016).*
European Search Report and Written Opinion for the European Patent Application No. EP20766043, mailed Oct. 20, 2022, 6 pages.
International Search Report and Written Opinion of the International Searching Authority mailed on Jun. 1, 2020 for International Application No. PCT/IB2020/051920, filed Mar. 5, 2020, pages.

* cited by examiner

*Primary Examiner* — Brenda L Coleman
*Assistant Examiner* — Madeline E Braun
(74) *Attorney, Agent, or Firm* — KDW Firm PLLC

(57) ABSTRACT

Provided are compounds of Formula (I) which have shown utility in modulating AMPA receptor signaling and thus preventing AMPA receptor-mediated toxicity, which may find use in the treatment of diseases in which AMPA receptor activation plays a role in neurodegeneration, including the treatment of multiple sclerosis and other diseases.

11 Claims, 1 Drawing Sheet

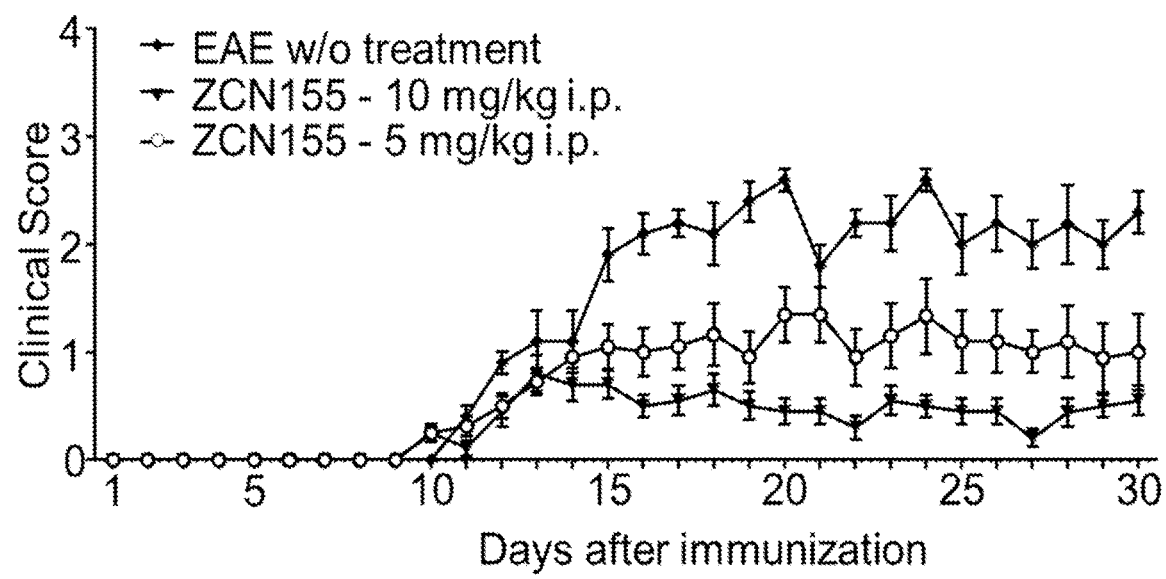

MODULATORS OF AMPA RECEPTOR SIGNALING

CROSS-REFERENCE TO RELATED APPLICATIONS

This application is a national stage entry, filed under 35 U.S.C. § 371, of International Application No. PCT/IB2020/051920, filed on Mar. 5, 2020, which claims the benefit of U.S. Pat. No. 62/814,076, filed on Mar. 5, 2019, the entire contents of which is hereby incorporated herein by reference in its entirety and for all purposes.

FIELD

The present disclosure relates to compounds of Formula (I), methods of making same, and their use in modulating AMPA receptor signaling, and in the treatment of human diseases and disorders related thereto.

BACKGROUND

Excessive glutamate, acting mainly through NMDARs and AMPARs, facilitates $Ca^{2+}$ influx, which can result in excitotoxicity under pathological conditions including ischemia, trauma, hypoglycemia and epileptic seizure. Glutamate receptor-mediated excitotoxicity is involved in the demyelination, loss of neurons/oligodendrocytes and axonal damage that are responsible for the neurological deficits in multiple sclerosis (MS). There is evidence that this neurotransmitter system can also modulate immune system function and that it may also be involved in the mechanisms of neuronal damage by inflammation. However, preventing glutamate-mediated excitotoxicity is difficult because glutamate receptors are essential for normal brain function.

A protein complex composed of the GluR2 subunit of the α-amino-3-hydroxy-5-methyl-4-isoxazolepropionic acid glutamate receptor (AMPAR) and glyceraldehyde-3-phosphate dehydrogenase (GAPDH) was shown to play a role in glutamate-mediated neurotoxicity and a peptide that disrupted the GluR2-GAPDH complex dramatically improved neurological outcomes in a mouse model of MS, the experimental autoimmune encephalomyelitis (EAE) model (Zhai et al., *Annals Clin. Transl. Neurology* 2015 2:388-400). Disrupting the GluR2-GAPDH complex prevented AMPAR-mediated excitotoxicity and improved neurological outcomes in the EAE model without immunosuppressant side-effects and without impairing AMPAR-mediated neurotransmission. The GluR2-GAPDH complex was also found to be significantly increased in post-mortem tissue from chronic MS patients.

US 20130336951 (Liu, Centre for Addiction and Mental Health) provides methods for modulating AMPA receptor-mediated excitotoxicity using an inhibitory peptide that modulates GAPDH association with GluR2 or p53. Additional compositions and methods for modulating this interaction and AMPA receptor-mediated excitotoxicity are needed.

SUMMARY

The present disclosure provides a series of 2-pyrrolopyrazole compounds of Formula (I) which modulate AMPA receptor signaling by inhibiting the association of the glutamate receptor AMPA type subunit 2 (glutamate receptor 2, or "GluR2") and glyceraldehyde 3-phosphate dehydrogenase ("GAPDH"). In some embodiments, the present disclosure provides 2-pyrrolopyrazole compounds of Formula (I) having improved biological potency, for example as inhibitors of the GluR2-GAPDH interaction, and/or as inhibitors of AMPA-mediated neurotoxicity. In some embodiments, the present disclosure also provides 2-pyrrolopyrazole compounds of Formula (I) having improved metabolic stability.

The present disclosure also provides methods of making and using the compounds of Formula (I). In some embodiments, the disclosure provides methods of treating a neurological disease or disorder, the method comprising administering to a subject in need a compound of Formula (I). In some embodiments, the neurological disease or disorder is one in which modulation of the interaction between GluR2 and glyceraldehyde-3-phosphate dehydrogenase is beneficial, or one in which modulation of AMPA receptor signaling is beneficial. In some embodiments, the neurological disease or disorder is characterized by excessive glutamate receptor-mediated excitotoxicity, including those characterized by GluR2/AMPAR neurotoxicity, including, but not limited to, amyotrophic lateral sclerosis (ALS), multiple sclerosis (MS), stroke, and epilepsy. In embodiments, the disclosure provides methods of inhibiting glutamate receptor-mediated excitotoxicity in a subject in need of such treatment, for example in a human subject having, or at risk for, stroke, epilepsy, or traumatic brain injury.

In some embodiments, the neurological disease or disorder is selected from amyotrophic lateral sclerosis, multiple sclerosis, epilepsy or stroke. In some embodiments, the neurological disease or disorder is multiple sclerosis (MS). In some embodiments, the disclosure provides methods of treating MS, including ameliorating one or more symptoms of MS or slowing the progression of MS in a subject in need of such treatment, the method comprising administering to a subject a compound of Formula (I). In some embodiments, the neurological disease or disorder is amyotrophic lateral sclerosis (ALS). In some embodiments, the disclosure provides methods of treating ALS, including ameliorating one or more symptoms of ALS or slowing the progression of ALS in a subject in need of such treatment, the method comprising administering to a subject a compound of Formula (I).

In one embodiment of the disclosure, there is included a compound of the Formula (I).

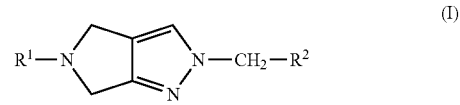

(I)

wherein,
$R^1$ is $(C_6-C_{10})$-aryl, or $(C_5-C_{10})$-heteroaryl, each of which is optionally substituted with one to three $R^4$ groups;
each $R^4$ is independently selected from the group consisting of halo, $-CF_3$, $-OCF_3$, $-CN$, $-NO_2$, $-R^a$, $-X^1-R^a$, $-OR^a$, $-X^1-OR^a$, $-SR^a$, $-X^1-SR^a$, $-NR^aR^b$, $-X^1-NR^aR^b$, $-NR^aR^c$, $-X^1-NR^aR^c$, $-C(=O)R^a$, $-X^1-C(=O)R^a$, $-C(=O)R^c$, $-X^1-C(=O)R^c$, $-C(=O)OR^a$, $-NR^aC(=O)R^b$, $-C(=O)NR^aR^b$, $-C(=O)NR^aR^c$, $-S(=O)_2NR^aR^b$, $-S(=O)_2NR^aR^c$, $-NR^aS(=O)_2R^b$, $-S(=O)_2R^a$ and $-S(=O)CF_3$;
each $R^a$ and $R^b$ is independently selected from the group consisting of H, $(C_1-C_6)$-alkyl, $(C_1-C_6)$-haloalkyl $(C_2-C_6)$-alkenyl, $(C_2-C_6)$-alkynyl, $(C_3-C_6)$-cycloalkyl, phenyl and benzyl, and each $R^c$ is independently selected from the group consisting of azetidino, pyrrolidino, piperidino, piperazino, morpholino, azepano, or diazepano, wherein the cyclic portion of $R^c$ is optionally further substituted with a halo, —OH, $(C_1-C_6)$-alkyl, or $(C_1-C_6)$-haloalkyl;

each $X^1$ is a $(C_1-C_6)$-alkylene;

$R^2$ is $(C_3-C_{10})$-cycloalkyl, $(C_3-C_{10})$-heterocycloalkyl, $(C_1-C_{10})$-alkyl, $(C_6-C_{10})$-aryl, or $(C_5-C_{10})$-heteroaryl, each of which is optionally substituted with one to three $R^3$;

each $R^3$ is independently selected from the group consisting of halo, —$CF_3$, —$OCF_3$, —CN, —$NO_2$, —$R^d$, —$X^2$-$R^d$, —X—$OR^d$, —$SR^d$, —$X^2$—$SR^d$, —$NR^dR^e$, —$X^2$—$NR^dR^e$, —$NR^dR^f$, —$X^2$—$NR^dR^f$, —C(=O)$R^d$, —$X^2$—C(=O)$R^d$, —C(=O)$R^f$, —$X^2$—C(=O)$R^f$, —C(=O)$OR^d$, —$NR^dC$(=O)$R^e$, —C(=O)$NR^dR^e$, —C(=O)$NR^dR^f$, —S(=O)$_2NR^dR^e$, S(=O)$_2NR^dR^f$, —$NR^dS$(=O)$_2R^e$, —S(=O)$_2R^d$ or —S(=O)$CF_3$;

each $R^d$ and $R^e$ are independently selected from the group consisting of H, $(C_1-C_6)$-alkyl, $(C_1-C_6)$-haloalkyl, $(C_2-C_6)$-alkenyl, $(C_2-C_6)$-alkynyl, $(C_3-C_6)$-cycloalkyl, phenyl and benzyl, and each $R^f$ is independently selected from the group consisting of azetidino, pyrrolidino, piperidino, piperazino, morpholino, azepano, and diazepano;

each $X^2$ is a $(C_1-C_6)$-alkylene;

and pharmaceutically acceptable salts, stereoisomers, and/or solvates thereof.

In one embodiment, the compounds of the Formula (I) are modulators of AMPA receptor signaling. In another embodiment and in one object of the disclosure, the compounds of the Formula (I) are useful for the treatment of diseases or conditions in which selective modulation of AMPA receptor signaling is beneficial. In another embodiment, the disease or condition is multiple sclerosis.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

BRIEF DESCRIPTION OF THE DRAWINGS

The FIGURE shows clinical scores of EAE mice treated with ZCN155, 5 mg/kg i.p. (open circles), 10 mg/kg i.p. (inverted triangles), or untreated (closed circles). The results show that administration ZCN155 from day 11~12 after immunization (1~2 days after the presence of the symptoms) greatly improves neurological function.

DETAILED DESCRIPTION

The present disclosure provides a series of 2-pyrrolopyrazole compounds of Formula (I) which modulate AMPA receptor signaling by inhibiting the association of the glutamate receptor AMPA type subunit 2 (glutamate receptor 2, or "GluR2") and glyceraldehyde 3-phosphate dehydrogenase ("GAPDH"). As discussed in more detail below, the present disclosure provides compounds of Formula (I) that are potent competitive inhibitors of the GluR2-GAPDH interaction, as well as potent inhibitors of AMPA-mediated neurotoxicity. In addition, the disclosure provides compounds having improved metabolic stability compared to a closely-related 1-pyrrolopyrazole reference compound.

Compounds that disrupt the GluR2-GAPDH complex provide a targeted approach to preventing and/or decreasing the excessive glutamate receptor-mediated excitotoxicity that underlies pathological conditions, while avoiding adverse effects such as immunosuppressant side-effects and the general impairment of AMPAR-mediated neurotransmission, which is essential for normal brain function. Thus, the compounds disclosed here represent a new class of therapeutic agents for the treatment of neurological diseases and disorders characterized by excessive glutamate receptor-mediated excitotoxicity, including those characterized by Glu R2/AMPAR neurotoxicity, including, but not limited to, ALS, MS, stroke, and epilepsy. In embodiments, the disclosure provides methods of inhibiting glutamate receptor-mediated excitotoxicity in a subject in need of such treatment, for example in a human subject having, or at risk for, stroke, epilepsy, or traumatic brain injury. Accordingly, the present disclosure also provides methods for treating neurological diseases and disorders characterized by excessive glutamate receptor-mediated excitotoxicity by administering a compound of Formula (I).

(I) Definitions

The term "$(C_1-C_p)$-alkyl" as used herein means straight and/or branched chain, saturated alkyl moieties containing from one to "p" carbon atoms and includes (depending on the identity of p) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable p is an integer representing the largest number of allowable carbon atoms in the referenced alkyl radical. Generally, "p" does not exceed 12 total carbon atoms.

The term "$(C_1-C_p)$-haloalkyl" as used herein refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc.

The term "$(C_2-C_p)$-alkenyl" as used herein means straight and/or branched chain, unsaturated alkyl moieties containing from one to "p" carbon atoms and includes at least one carbon-carbon double bond and includes (depending on the identity of p) ethenyl, 1-propenyl, isopropenyl, 1-butenyl, 2-butenyl, t-butenyl, 1-pentenyl, 2-methyl-1-pentenyl, 3-methyl-1-pentenyl, 4-methyl-1-pentenyl, 1-hexenyl, 2-hexenyl and the like, where the variable p is an integer representing the largest number of allowable carbon atoms in the referenced alkenyl radical. Generally, "p" does not exceed 12 total carbon atoms.

The term "$(C_2-C_p)$-alkynyl" as used herein means straight and/or branched chain, unsaturated alkyl moieties containing from one to "p" carbon atoms and includes at least one carbon-carbon triple bond (and optionally including double bonds) and includes (depending on the identity of p) ethynyl, 1-propynyl, isopropynyl, 1-butynyl, 2-butynyl, 1-pentynyl, 3-methyl-1-pentynyl, 4-methyl-1-pentynyl, 1-hexynyl, 2-hexynyl and the like, where the variable p is an integer representing the largest number of allowable carbon atoms in the referenced alkynyl radical. Generally, "p" does not exceed 12 total carbon atoms.

The term "$C_{3-p}$cycloalkyl" as used herein means a monocyclic, bicyclic or tricyclic saturated carboxylic group containing from three to "p'" carbon atoms and includes (depending on the identity of p) cyclopropyl, cyclobutyl, cyclopentyl, cyclohexyl and the like, where the variable p' is an integer representing the largest number of allowable carbon atoms in the referenced cycloalkyl radical. The term cycloalkyl also includes fully saturated and partially unsaturated derivatives.

The term "heteroaryl" as used herein refers to aromatic cyclic or polycyclic ring systems having five to twelve ring vertices at least one ring vertex is a heteroatom chosen from N, O and S. In embodiments, heteroaryls contain one to three heteroatoms selected form N, O and S. In embodiments, heteroaryls contain one to two heteroatoms selected form N, O and S. In embodiments, heteroaryls contain one heteroatoms selected form N, O and S. When the heteroaryl is a polycylic ring, at least one of the ring systems is an aromatic ring. Examples of heteroaryl groups include, without limitation, furyl, thienyl, pyridyl, pyrazinyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl and quinazolinyl, among others.

The term "heterocyclylalkyl" as used herein includes non-aromatic rings or ring systems having three to twelve ring vertices wherein at least one ring vertex is a heteroatom chosen from N, O and S. For example, the heterocyclyl groups include all of the fully saturated and partially unsaturated derivatives of the above-mentioned heteroaryl groups. Examples of heterocyclic groups include, without limitation, piperidinyl, tetrahydropyranyl, pyrrolidinyl, tetrahydrofuranyl, morpholinyl, thiomorpholinyl, piperidinyl, piperazinyl, thiazolidinyl, isothiazolidinyl, and imidazolidinyl.

The term "aryl" as used herein refers to cyclic groups that contain at least one aromatic ring, for example a single ring (e.g. phenyl) or multiple condensed rings (e.g. naphthyl). In an embodiment of the present disclosure, the aryl group contains 6, 9 or 10 atoms such as phenyl, naphthyl, indanyl, anthracenyl, 1,2-dihydronaphthyl, 1,2,3,4-tetrahydronaphthyl, fluorenyl, indanyl, indenyl and the like The suffix "ene" added on to any of the above groups means that the group is divalent, i.e. inserted between two other groups.

The term "halo" as used herein refers to a halogen atom and includes fluorine (F), chlorine (Cl), bromine (Br) and iodine (I).

The term "pharmaceutically acceptable salt" refers, for example, to a salt that retains the desired biological activity of a compound of the present disclosure and does not impart undesired toxicological effects thereto; and may refer to an acid addition salt or a base addition salt.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

In embodiments of the present disclosure, the compounds may have an asymmetric center. These compounds exist as enantiomers. Where compounds possess more than one asymmetric center, they may exist as diastereomers. It is to be understood that all such isomers and mixtures thereof in any proportion are encompassed within the scope of the present disclosure, and are known, generally, as stereoisomers. It is to be further understood that, while the stereochemistry of the compounds may be as shown in any given compound listed herein, such compounds may also contain certain amounts (e.g. less than 20%, suitably less than 10%, more suitably less than 5%) of compounds of the disclosure having alternate stereochemistry. For example, compounds of the disclosure that are shown without any stereochemical designations are understood to be racemic mixtures (i.e. contain an equal amount of each possible enantiomer or diastereomer). However, it is to be understood that all enantiomers and diastereomers are included within the scope of the present disclosure, including mixtures thereof in any proportion.

The term "effective amount" or "therapeutically effective amount" or "pharmaceutically effective amount" as used herein means an amount effective, at dosages and for periods of time necessary to achieve the desired result. For example in the context of treating a subject with a disease or condition in which modulation of AMPA receptor signaling would be beneficial, such as pain, an effective amount is an amount that, for example, provides some alleviation, amelioration, mitigation and/or decrease in the amount of pain experienced by a subject.

Effective amounts may vary according to factors such as the disease state, age, sex and/or weight of the subject. The amount of a given compound that will correspond to such an amount will vary depending upon various factors, such as the given drug or compound, the pharmaceutical Formulation, the route of administration, the type of condition, disease or disorder, the identity of the subject being treated, combination treatment, and the like, but can nevertheless be routinely determined by one skilled in the art.

As used herein, a "subject" refers to all members of the animal kingdom including mammals, and suitably refers to humans. A member of the animal kingdom includes, without limitation, a mammal (such as a human, primate, swine, sheep, cow, equine, horse, camel, canine, dog, feline, cat, tiger, leopard, civet, mink, stone marten, ferret, house pet, livestock, rabbit, mouse, rat, guinea pig or other rodent, seal, whale and the like), fish, amphibian, reptile, and bird (such as water fowl, migratory bird, quail, duck, goose, poultry, or chicken). In an embodiment of the present disclosure, the subject is in need of a compound or composition of the disclosure. In a preferred embodiment, the subject is a human subject.

The terms "treatment" or "treating" as used herein pertain generally to describe the management and care of a subject, including human and animal subjects (e.g., in veterinary applications), to achieve a therapeutic effect in relation to a disease or disorder in the subject, for example, to alleviate, ameliorate, or mitigate one or more symptoms or complications of the disease or disorder, to slow the progression of the disease or disorder, including a reduction in the rate of progression or a halt in the progression, and cure of the condition.

As used herein, the term "prodrug" refers to a substance that is prepared in an inactive form that is converted to an active form (i.e., drug) within the body or cells thereof by the action of, for example, endogenous enzymes or other chemicals and/or conditions. Prodrug derivatives of the compounds of Formula (I) or pharmaceutically acceptable salts or solvates thereof, can be prepared by methods known to those of ordinary skill in the art.

(II) Compounds of the Disclosure

The present disclosure relates to compounds of the Formula (I) which are selective modulators of AMPA receptor signaling by prevention of the interaction between GluR2 and GAPDH. In another embodiment and in one object of the disclosure, the compounds of the Formula (I) are useful for the treatment of diseases or conditions in which selective modulation of AMPA receptor signaling is beneficial. In another embodiment, the disease or condition is multiple sclerosis.

In one embodiment of the disclosure, there is included a compound of the Formula (I).

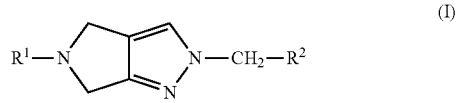

wherein,
$R^1$ is $(C_6-C_{10})$-aryl, or $(C_5-C_{10})$-heteroaryl, each of which is optionally substituted with one to three $R^4$ groups;
each $R^4$ is independently selected from the group consisting of halo, —$CF_3$, —$OCF_3$, —CN,
—$NO_2$, —$R^a$, —$X^1$—$R^a$, —$OR^a$, —$X^1$—$OR^a$, —$SR^a$,
—$X^1$—$SR^a$, —$NR^aR^b$, —$X^1$—$NR^aR^b$, —$NR^aR^c$,
—$X^1$—$NR^aR^c$, —C(=O)$R^a$, —$X^1$—C(=O)$R^a$,
—C(=O)$R^c$, —$X^1$—C(=O)$R^c$, —C(=O)$OR^a$,
—$NR^aC$(=O)$R^b$, —C(=O)$NR^aR^b$, —C(=O)
$NR^aR^c$, —S(=O)$_2NR^aR^b$, —S(=O)$_2NR^aR^c$,
—$NR^aS$(=O)$_2R^b$, —S(=O)$_2R^a$ and —S(=O)$CF_3$;
each $R^a$ and $R^b$ is independently selected from the group consisting of H, $(C_1-C_6)$-alkyl, $(C_1-C_6)$-haloalkyl $(C_2-C_6)$-alkenyl, $(C_2-C_6)$-alkynyl, $(C_3-C_6)$-cycloalkyl, phenyl and benzyl, and each $R^c$ is independently selected from the group consisting of azetidino, pyrrolidino, piperidino, piperazino, morpholino, azepano, or diazepano, wherein the cyclic portion of $R^c$ is optionally further substituted with a halo, —OH, $(C_1-C_6)$-alkyl, or $(C_1-C_6)$-haloalkyl;
each $X^1$ is a $(C_1-C_6)$-alkylene;
$R^2$ is $(C_3-C_{10})$-cycloalkyl, $(C_3-C_{10})$-heterocycloalkyl, $(C_1-C_{10})$-alkyl, $(C_6-C_{10})$-aryl, or $(C_5-C_{10})$-heteroaryl, each of which is optionally substituted with one to three $R^3$;
each $R^3$ is independently selected from the group consisting of halo, —$CF_3$, —$OCF_3$, —CN,
—$NO_2$, —$R^d$, —$X^2$—$R^d$, $OR^d$, —$X^2$—$OR^d$, —$SR^d$,
—$X^2$—$SR^d$, —$NR^dR^e$, —$X^2$—$NR^dR^e$, —$NR^dR^f$,
—$X^2$—$NR^dR^f$, —C(=O)$R^d$, —$X^2$—C(=O)$R^d$,
—C(=O)$R^f$, —$X^2$—C(=O)$R^f$, —C(=O)$OR^d$,
—$NR^dC$(=O)$R^e$, —C(=O)$NR^dR^e$, —C(=O)
$NR^dR^f$, —S(=O)$_2NR^dR^e$, S(=O)$_2NR^dR^f$, —$NR^dS$
(=O)$_2R^e$, —S(=O)$_2R^d$ or —S(=O)$CF_3$;
each $R^d$ and $R^e$ are independently selected from the group consisting of H, $(C_1-C_6)$-alkyl, $(C_1-C_6)$-haloalkyl, $(C_2-C_6)$-alkenyl, $(C_2-C_6)$-alkynyl, $(C_3-C_6)$-cycloalkyl, phenyl and benzyl, and each $R^f$ is independently selected from the group consisting of azetidino, pyrrolidino, piperidino, piperazino, morpholino, azepano, and diazepano;
each $X^2$ is a $(C_1-C_6)$-alkylene;
and pharmaceutically acceptable salts, stereoisomers, and/or solvates thereof.

In one embodiment of the disclosure, the compound of the Formula (I) has the Formula ($I_j$).

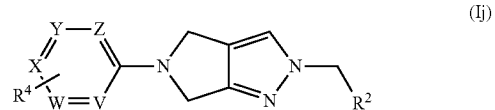

wherein
V, W, X, Y and Z are each independently selected from the group consisting of CH or N, wherein no more than three of V, W, X, Y, and Z can be N; and
$R^4$ and $R^2$ are as defined above.

In embodiments, $R^2$ is $(C_3-C_{10})$-cycloalkyl, $(C_6-C_{10})$-aryl, or $(C_5-C_{10})$-heteroaryl, each of which is optionally substituted with one to three $R^3$ In another embodiment of the disclosure, the compound of the Formula (I) has the Formula (Ik)

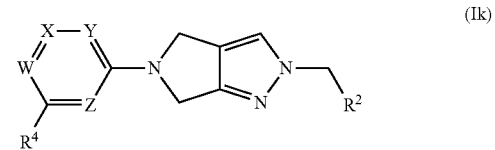

wherein W, X, Y, Z, $R^4$, and $R^2$ are as defined above.

In embodiments of Formula (Ij) and (Ik), $R^4$ is selected from the group consisting of —CN, —C(=O)$R^a$, —C(=O)
$R^c$, —C(=O)$OR^d$, —$NR^dC$(=O)$R^e$, —C(=O)$NR^dR^e$,
—C(=O)$NR^dR^f$, —S(=O)$_2NR^dR^e$, S(=O)$_2NR^dR^f$, and
—S(=O)$_2R^d$.

In embodiments of Formula (Ij) and (Ik), $R^2$ is selected from the group consisting of $(C_6-C_{10})$-aryl, $(C_5-C_{10})$-heteroaryl, $(C_3-C_{10})$-cycloalkyl, each of which is optionally substituted with from one to three $R^3$.

In another embodiment of the disclosure, the compound of the Formula (I) is selected from the group consisting of

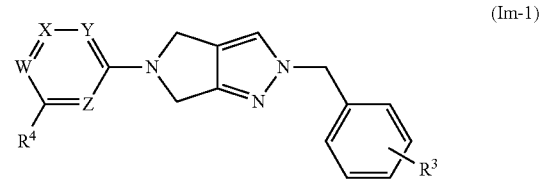

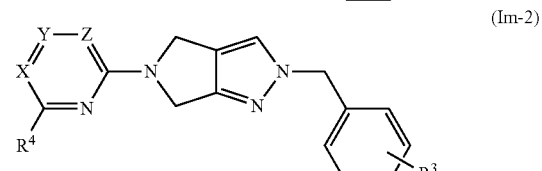

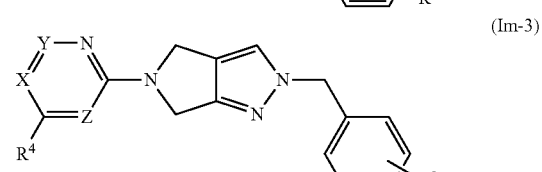

-continued

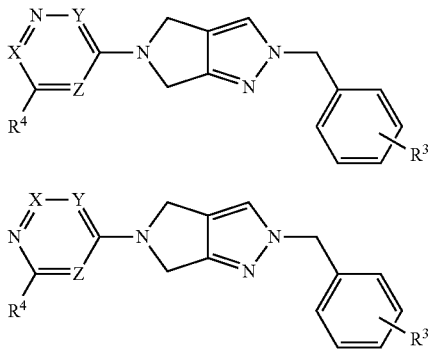
(Im-4)

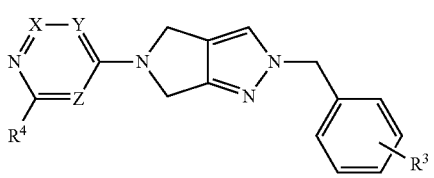
(Im-5)

wherein W, X, Y, Z, R⁴ and R³ are as defined above.

In another embodiment of the disclosure, the compound of the Formula (I) is selected from the group consisting of

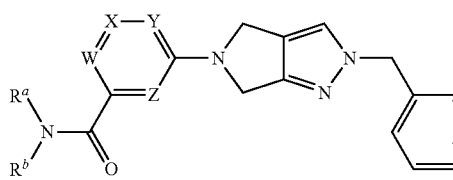
(In-1)

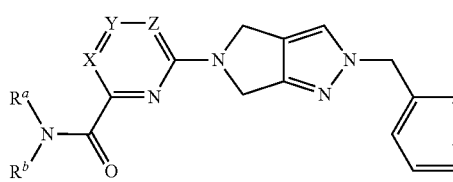
(In-2)

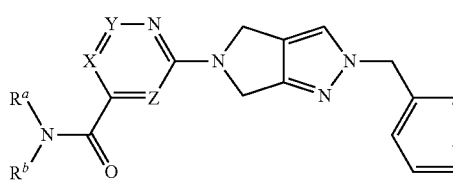
(In-3)

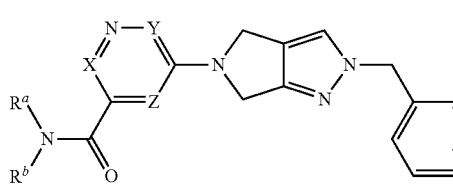
(In-4)

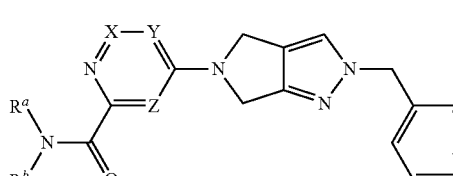
(In-5)

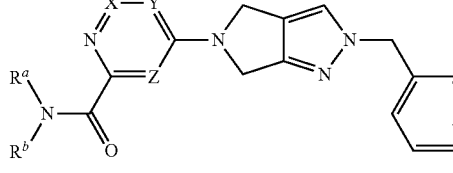

wherein W, X, Y, Z, R³, $R^a$, and $R^b$ are as defined above.

In embodiments, the —C(=O)NR$^a$R$^b$ group of Formulas (In-1) to (In-5) are replaced with a —C(=O)NR$^a$R$^c$ group or a C(=O)R$^c$ group.

In another embodiment of the disclosure, the compound of the Formula (I) has the Formula (If).

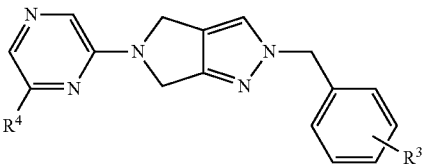
(If)

Wherein R⁴ and R³ are as defined above.

In embodiments, R⁴ of Formula (If) is independently selected from the group consisting of —CN, —NR$^a$R$^b$, —C(=O)R$^a$, —C(=O)R$^c$, —C(=O)OR$^a$, —NR$^a$C(=O)R$^b$, —C(=O)NR$^a$R$^b$,
—C(=O)NR$^a$R$^c$, —S(=O)$_2$NR$^a$R$^b$, —S(=O)$_2$NR$^a$R$^c$, —NR$^a$S(=O)$_2$R$^b$, —S(=O)$_2$R$^a$ and —S(=O)CF$_3$.

In another embodiment of the disclosure, the compound of the Formula (I) has the Formula (If-1).

(If-1)

wherein R³, $R^a$, and $R^b$ are as defined above.

In another embodiment of the disclosure, the compound of the Formula (I) has the Formula (If-2).

(If-2)

In embodiments, the —C(=O)NR$^a$R$^b$ group of Formula (If-1) or (If-2) is replaced with a —C(=O)NR$^a$R$^c$ group or a C(=O)R$^c$ group.

In embodiments, R$^a$ and R$^b$ of Formula (If-1) or (If-2) are independently selected from the group consisting of H, (C$_1$-C$_6$)-alkyl, and (C$_3$-C$_6$)-cycloalkyl, and R$^c$ is selected from the group consisting of piperidino, piperazino, and morpholino, wherein the cyclic portion of R$^c$ is optionally further substituted with a (C$_1$-C$_6$)-alkyl.

In another embodiment of the disclosure, the compound of the Formula (I) has the Formula (Io)

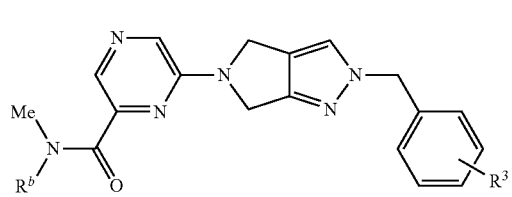
(Io)

where $R^b$ and $R^3$ are as defined above.

In another embodiment of the disclosure, the compound of the Formula (I) has the Formula (Io-1)

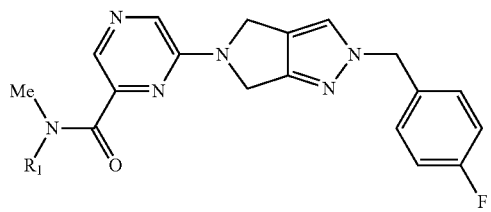
(Io-1)

In another embodiment of the disclosure, the compound of the Formula (I) has the Formula (Io-2)

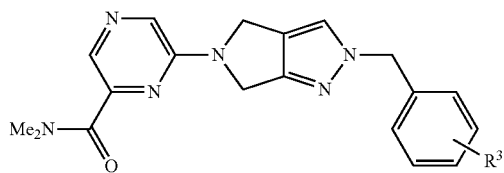
(Io-2)

In embodiments, $R^b$ of Formula (Io) and (Io-1) is replaced with $R^c$.

In embodiments, $R^b$ of Formula (Io) and (Io-1) is selected from the group consisting of $(C_1$-$C_6)$-alkyl, and $(C_3$-$C_6)$-cycloalkyl, In embodiments, $R^3$ of Formula (Io) and (Io-2) is selected from the group consisting of halo, —$CF_3$, —$OCF_3$, —CN, —$R^d$, and —$NR^dR^e$.

In another embodiment of the disclosure, the compound of the Formula (I) is

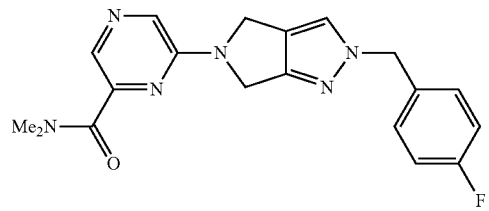 [SMILES: CN(C)C(=O)c1cncc(N2Cc3cn(Cc4ccc(F)cc4)nc3C2)n1]

In one embodiment, the compound of the Formula (I) has the Formula (Ip).

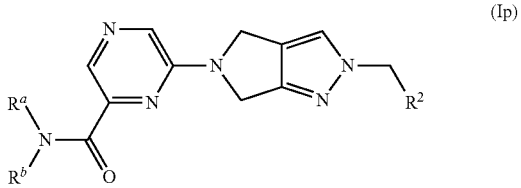
(Ip)

wherein $R^a$, $R^b$, and $R^2$ are as defined above.

In one embodiment, the compound of the Formula (I) is selected from the group consisting of

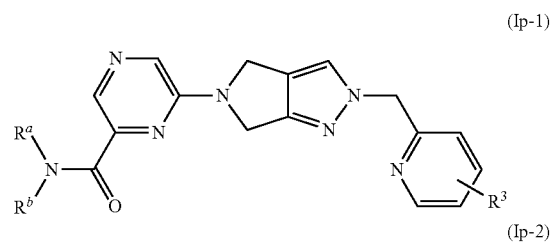
(Ip-1)

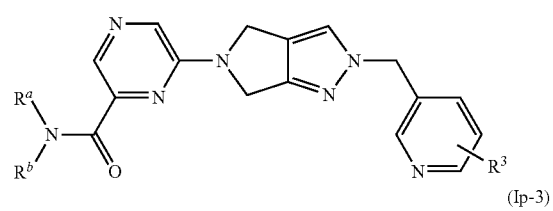
(Ip-2)

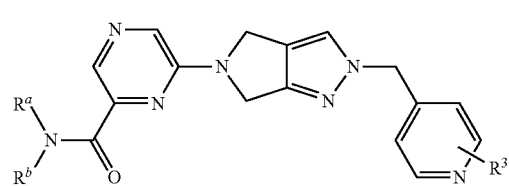
(Ip-3)

wherein $R^a$, $R^b$, and $R^3$ are as defined above.

In embodiments, the —C(=O)NR$^a$R$^b$ group of Formulas (Ip-1) to (Ip-3) is replaced with a —C(=O)NR$^a$R$^c$ group or a C(=O)R$^c$ group.

In one embodiment, the compound of the Formula (I) is selected from the group consisting of

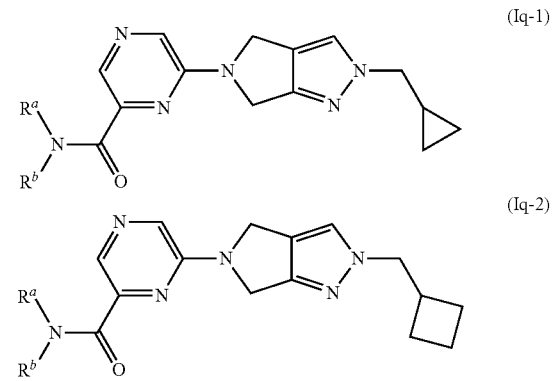
(Iq-1)

(Iq-2)

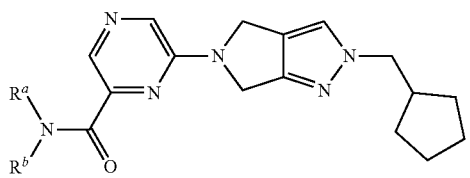
(Iq-3)

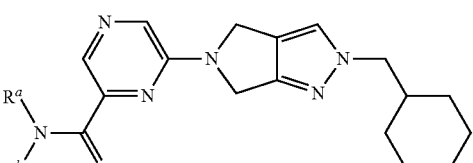
(Iq-4)

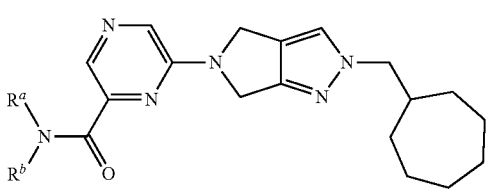
(Iq-5)

In embodiments, the cycloalkyl portion of (Iq-1) and (Iq-5) displayed on the right hand portion of the structures above are further substituted with an $R^3$ group.

In embodiments, the —C(=O)NR$^a$R$^b$ group of Formulas (Iq-1) to (I1-5) is replaced with a —C(=O)NR$^a$R$^c$ group or a C(=O)R$^c$ group.

In another embodiment of the disclosure, the compound of the Formula (I) has the Formula (Ig).

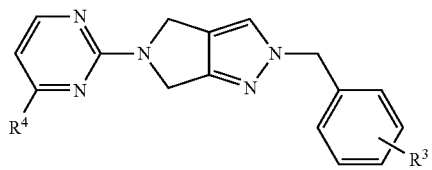
(Ig)

In embodiments, $R^4$ of Formula (Ig) is independently selected from the group consisting of —CN, —NR$^a$R$^b$, —C(=O)R$^a$, —C(=O)R$^c$, —C(=O)OR$^a$, —NR$^a$C(=O)R$^b$, —C(=O)NR$^a$R$^b$, —C(=O)NR$^a$R$^c$, —S(=O)$_2$NR$^a$R$^b$, —S(=O)$_2$NR$^a$R$^c$, —NR$^a$S(=O)$_2$R$^b$, —S(=O)$_2$R$^a$ and —S(=O)CF$_3$.

In embodiments, $R^a$ and $R^b$ of Formula (Ig) are independently selected from the group consisting of H, (C$_1$-C$_6$)-alkyl, and (C$_3$-C$_6$)-cycloalkyl, and $R^c$ is selected from the group consisting of piperidino, piperazino, and morpholino, wherein the cyclic portion of $R^c$ is optionally further substituted with a (C$_1$-C$_6$)-alkyl.

In another embodiment of the disclosure, the compound of the Formula (I) has the Formula (Ig-1).

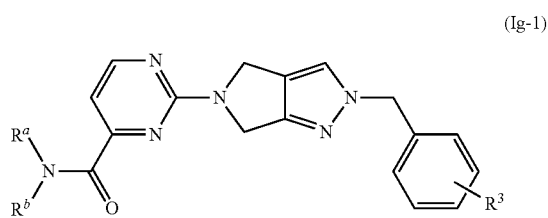
(Ig-1)

In another embodiment of the disclosure, the compound of the Formula (I) has the Formula (Ig-2).

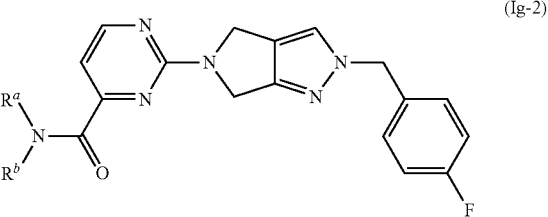
(Ig-2)

In embodiments, the —C(=O)NR$^a$R$^b$ group of Formula (Ig-1) or (Ig-2) is replaced with a —C(=O)NR$^a$R$^c$ group or a C(=O)R$^c$ group.

In embodiments, $R^a$ and $R^b$ of Formula (Ig-1) or (Ig-2) are independently selected from the group consisting of H, (C$_1$-C$_6$)-alkyl, and (C$_3$-C$_6$)-cycloalkyl, and $R^c$ is selected from the group consisting of piperidino, piperazino, and morpholino, wherein the cyclic portion of $R^c$ is optionally further substituted with a (C$_1$-C$_6$)-alkyl.

In another embodiment of the disclosure, the compound of the Formula (I) has the Formula (Ig-3).

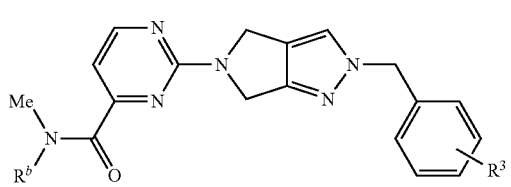
(Ig-3)

In another embodiment of the disclosure, the compound of the Formula (I) has the Formula (Ig-4).

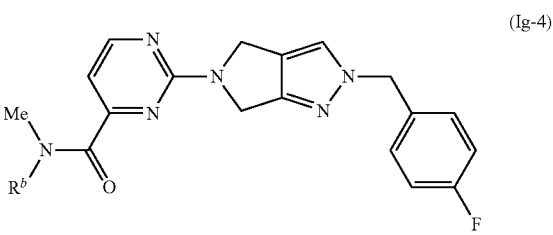
(Ig-4)

In another embodiment of the disclosure, the compound of the Formula (I) has the Formula (Ig-5).

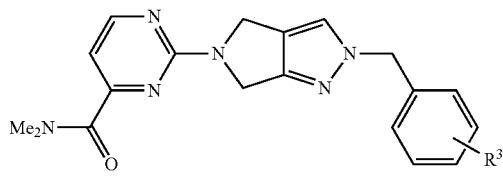

(Ig-5)

In embodiments, $R^b$ of Formula (Ig-3) to (Ig-5) is selected from the group consisting of $(C_1-C_6)$-alkyl, and $(C_3-C_6)$-cycloalkyl, In embodiments, $R^3$ of Formulas (Ig) to (Ig-5) is selected from the group consisting of halo, —$CF_3$, —$OCF_3$, —CN, —$R^d$, and —$NR^dR^e$.

In another embodiment of the disclosure, the compound of the Formula (I) has the structure

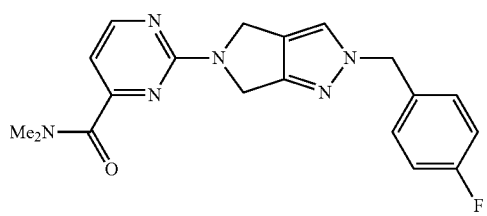 [SMILES: CN(C)C(=O)c1ccnc(N2Cc3cn(Cc4ccc(F)cc4)nc3C2)n1]

In embodiments, the phenyl group at position $R^2$ of Formula (I) in sub-formulae (Ig) to (Ig-5) is replaced with a pyridyl group. In embodiments, the pyridyl is attached at the 2-, 3- or 4-position.

In one embodiment, the compound of the Formula (I) has the Formula (Ib-1).

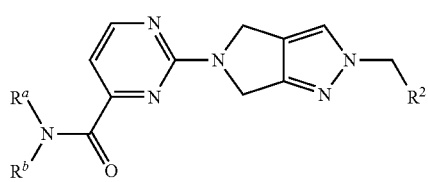

(Ib-1)

wherein $R^2$, $R^a$ and $R^b$ are as defined in Formula (I).

In one embodiment, the compound of the Formula (I) is selected from the group consisting of

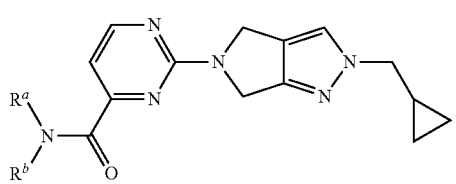

(Ir-1)

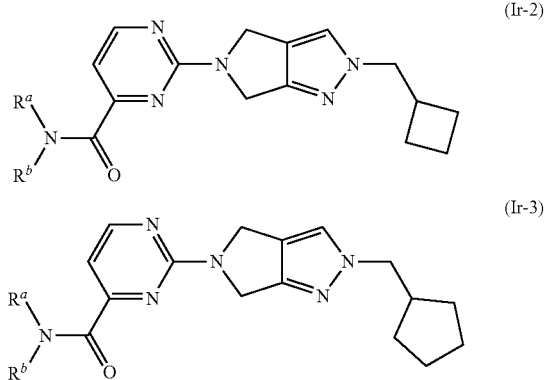

(Ir-2)

(Ir-3)

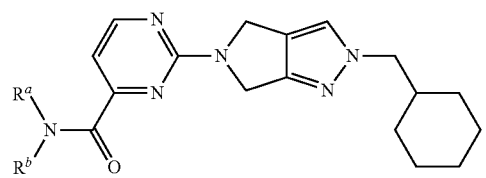

(Ir-4)

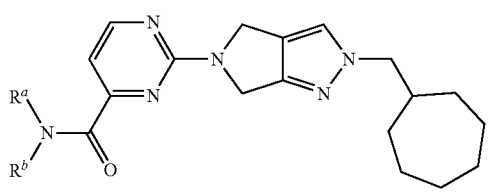

(Ir-5)

In embodiments, the cycloalkyl portion of (Ir-1) and (Ir-5) displayed on the right hand portion of the structures above are further substituted with an $R^3$ group.

In embodiments, the —C(=O)$NR^aR^b$ group of Formulas (Ir-1) to (Ir-5) is replaced with a —C(=O)$NR^aR^c$ group or a C(=O)$R^c$ group.

In another embodiment of the disclosure, the compound of the Formula (I) has the formula (Ie).

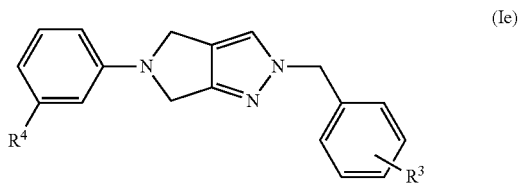

(Ie)

In embodiments, $R^4$ of Formula (Ie) is independently selected from the group consisting of —CN, —$NR^aR^b$, —C(=O)$R^a$, —C(=O)$R^c$, —C(=O)$OR^a$, —$NR^aC$(=O)$R^b$, —C(=O)$NR^aR^b$, —C(=O)$NR^aR^c$, —S(=O)$_2NR^aR^b$, —S(=O)$_2NR^aR^c$, —$NR^aS$(=O)$_2R^b$, —S(=O)$_2R^a$ and —S(=O)$CF_3$.

In another embodiment of the disclosure, the compound of the Formula (I) has the Formula (Ie-1).

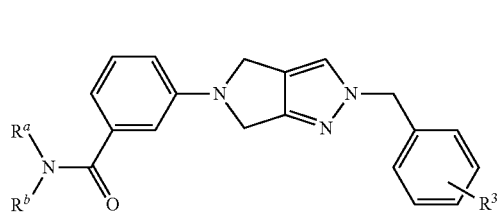

(Ie-1)

wherein $R^3$, $R^a$, and $R^b$ are as defined above.

In another embodiment of the disclosure, the compound of the Formula (I) has the Formula (Ie-2).

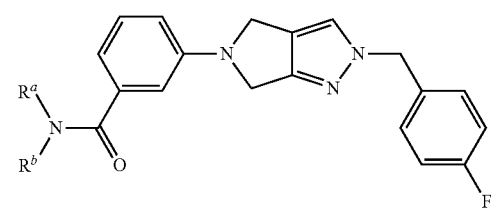

(Ie-2)

In embodiments, the —C(=O)NR$^a$R$^b$ group of Formula (Ie-1) or (Ie-2) is replaced with a —C(=O)NR$^a$R$^c$ group or a C(=O)R$^c$ group.

In embodiments, R$^a$ and R$^b$ of Formula (If-1) or (If-2) are independently selected from the group consisting of H, $(C_1\text{-}C_6)$-alkyl, and $(C_3\text{-}C_6)$-cycloalkyl, and R$^c$ is selected from the group consisting of piperidino, piperazino, and morpholino, wherein the cyclic portion of R$^c$ is optionally further substituted with a $(C_1\text{-}C_6)$-alkyl.

In another embodiment of the disclosure, the compound of the Formula (I) has the Formula (Ie-3).

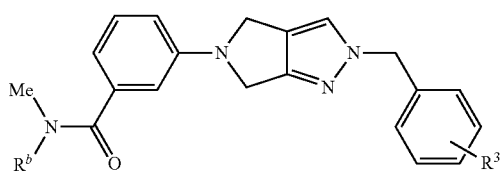

(Ie-3)

In another embodiment of the disclosure, the compound of the Formula (I) has the Formula (Ie-4).

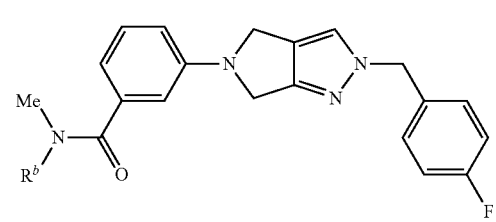

(Ie-4)

In another embodiment of the disclosure, the compound of the Formula (I) has the Formula (Ie-5).

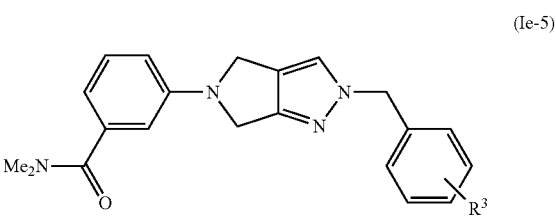

(Ie-5)

In embodiments, R$^b$ of Formula (Ie-3) to (Ie-5) is selected from the group consisting of $(C_1\text{-}C_6)$-alkyl, and $(C_3\text{-}C_6)$-cycloalkyl, In embodiments, R$^3$ of Formulas (Ie) to (Ie-5) is selected from the group consisting of halo, —CF$_3$, —OCF$_3$, —CN, —R$^d$, and —NR$^d$R$^e$.

In another embodiment of the disclosure, the compound of the Formula (I) has the structure.

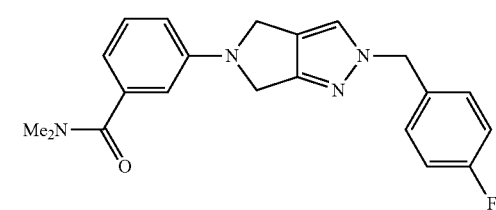 [SMILES: CN(C)C(=O)c1cccc(N2Cc3cn(Cc4ccc(F)cc4)nc3C2)c1]

In embodiments, the phenyl group at position R$^2$ of Formula (I) in sub-formulas (Ie) to (Ie-5) is replaced with a pyridyl group. In embodiments, the pyridyl is attached at the 2-, 3- or 4-position.

In one embodiment, the compound of the Formula (I) has the Formula (Is).

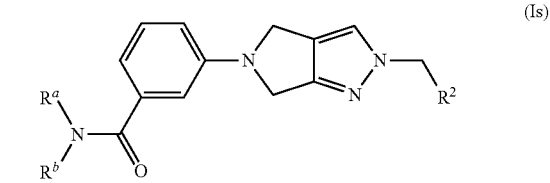

(Is)

wherein R$^a$, R$^b$ and R$^2$ are as defined in Formula I.

In one embodiment, the compound of the Formula (I) is selected from the group consisting of

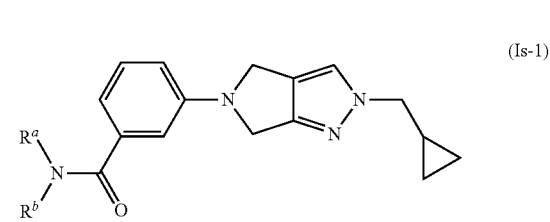

(Is-1)

-continued

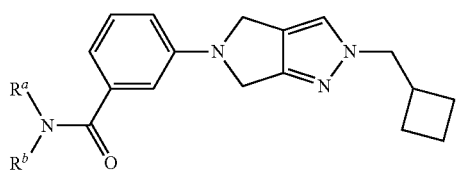
(Is-2)

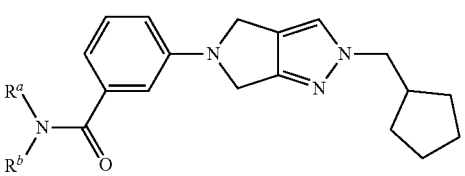
(Is-3)

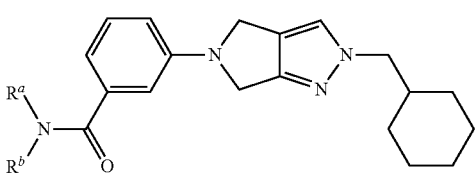
(Is-4)

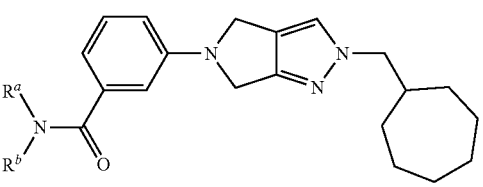
(Is-5)

In embodiments, the cycloalkyl portion of (Is-1) and (Is-5) displayed on the right hand portion of the structures above are further substituted with an $R^3$ group.

In embodiments, the —C(=O)NR$^a$R$^b$ group of Formulas (Is-1) to (Is-5) is replaced with a —C(=O)NR$^a$R$^c$ group or a C(=O)R$^c$ group.

In another embodiment of the disclosure, the compound of the Formula (I) has the Formula (It).

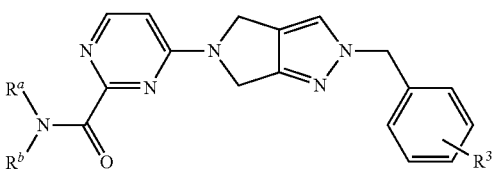
(It)

wherein $R^1$, $R^b$, and $R^3$ are as defined in Formula I.

In one embodiment, the compound of the Formula (I) has the Formula (Iu).

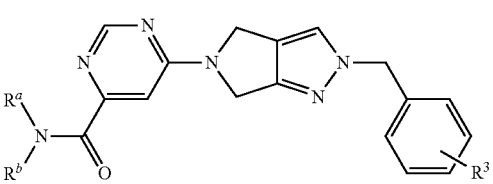
(Iu)

In embodiments, $R^a$ and $R^b$ of Formula (It) or (Iu) are independently selected from the group consisting of H, ($C_1$-$C_6$)-alkyl, and ($C_3$-$C_6$)-cycloalkyl, and $R^c$ is selected from the group consisting of piperidino, piperazino, and morpholino, wherein the cyclic portion of $R^c$ is optionally further substituted with a ($C_1$-$C_6$)-alkyl.

In embodiments, $R^3$ of Formula (It) or (Iu) is selected from the group consisting of halo, —CF$_3$, —OCF$_3$, —CN, —R$^d$, and —NR$^d$R$^e$.

In one embodiment, the compound is in a substantially purified form with an optical purity of at least 60% (i.e., 60% of the compound, on a molar basis, is the desired stereoisomer or enantiomer, and 40% is undesired stereoisomer(s) or enantiomer), e.g., at least 70%, e.g., at least 80%, e.g., at least 90%, e.g., at least 95%, e.g., at least 97%, e.g., at least 98%, e.g., at least 99%.

In another embodiment, the compounds of the Formula (I) may be prepared, purified, and/or handled as a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19. For example, if the compound of Formula (I) is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound of Formula (I) is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

In another embodiment, the compounds of the Formula (I) may be prepared, purified, and/or handled as a corresponding solvate of the compound. If the solvent is water, the solvate may be conveniently referred to as a hydrate, for example, a hemi-hydrate, a mono-hydrate, a di-hydrate, a tri-hydrate, etc. Typical procedures for making and identifying suitable hydrates and solvates are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999. Hydrates and solvates can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, DE), Avantium Technologies (Amsterdam) and Aptuit (Greenwich, CT). For the avoidance of doubt, it is understood that the phrase "pharmaceutically acceptable salts and solvates thereof" and the phrase "pharmaceutically acceptable salt or solvate thereof" embrace pharmaceutically acceptable solvates (e.g., hydrates) of the compounds, pharmaceutically acceptable salts of the compounds, as well as pharmaceutically acceptable solvates (e.g., hydrates) of pharmaceutically acceptable salts of the compounds.

In another embodiment, the compound of the Formula (I) may be prepared, purified, and/or handled as a compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Greene and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality. For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc). For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH—Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O•). For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide. For example, a thiol group may be protected as a thioether (—SR), for example, as: a benzyl thioether; an acetamidomethyl ether (—S—CH$_2$NHC(=O) CH$_3$).

In another embodiment, the compound of the Formula (I) may be prepared, purified, and/or handled in the form of a prodrug. Typically, the prodrug is inactive, or less active than the desired active compound, but may provide advantageous handling, administration, or metabolic properties. For example, active compounds which have a hydroxyl or carboxylic acid group may be converted to prodrugs which are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O) OH) in the parent compound, with, where appropriate, prior protection of any other reactive groups present in the parent compound, followed by deprotection if required.

(III) Compositions

The present disclosure also includes pharmaceutical compositions comprising a compound of the Formula (I), as defined above, or pharmaceutically acceptable salts, solvates, and prodrugs thereof, and a pharmaceutically acceptable carrier or diluent. The compounds are suitably formulated into pharmaceutical compositions for administration to subjects, preferably humans in a biologically compatible form suitable for administration in vivo.

The compositions containing the compounds of Formula (I) can be prepared by known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (2003-20th edition) and in The United States Pharmacopeia: The National Formulary (USP 24 NF19) published in 1999. On this basis, the compositions include, albeit not exclusively, solutions of the substances in association with one or more pharmaceutically acceptable vehicles or diluents, and contained in buffered solutions with a suitable pH and iso-osmotic with the physiological fluids.

In one embodiment, the 2-pyrrolopyrazole compounds of the Formula (I) may be administered alone. In another embodiment, the compounds of the Formula (I) may be administered in a pharmaceutical Formulation (e.g., composition, preparation, medicament) comprising at least one 2-pyrrolopyrazole compound of the Formula (I), as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilizers, solubilizes, surfactants (e.g., wetting agents), masking agents, coloring agents, flavoring agents, and sweetening agents. The formulation may further comprise other active agents, for example, other therapeutic agents.

Thus, the present invention further provides pharmaceutical compositions, as defined above, and methods of making a pharmaceutical composition comprising admixing at least one 2-pyrrolopyrazole compound of the Formula (I), as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

Suitable carriers, diluents, excipients, etc. can be found in standard pharmaceutical texts, for example, *Remington's Pharmaceutical Sciences,* 18th edition, Mack Publishing Company, Easton, Pa., 1990; and Handbook of *Pharmaceutical Excipients,* 5th edition, 2005. The Formulations may be prepared by any methods well known in the art of pharmacy. Such methods include the step of bringing into association the compound with a carrier which constitutes one or more accessory ingredients. In general, the Formulations are prepared by uniformly and intimately bringing into association the compound with carriers (e.g., liquid carriers, finely divided solid carrier, etc.), and then shaping the product, if necessary. The Formulation may be prepared to provide for rapid or slow release; immediate, delayed, timed, or sustained release; or a combination thereof.

In another embodiment, Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

In another embodiment, Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

In another embodiment, the compound of the Formula (I) may be dissolved in, suspended in, or admixed with one or more other pharmaceutically acceptable ingredients. The compound may be presented in a liposome or other microparticulate which is designed to target the compound, for example, to blood components or one or more organs.

In another embodiment, Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

In a further embodiment, Formulations suitable for buccal administration include mouthwashes, lozenges, pastilles, as well as patches, adhesive plasters, depots, and reservoirs. Lozenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

In another embodiment, Formulations suitable for sublingual administration include tablets, lozenges, pastilles, capsules, and pills.

In a further embodiment, Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, lozenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

In one embodiment, tablets may be made by conventional means, e.g., compression or molding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavors, flavor enhancing agents, and sweeteners. Molded tablets may be made by molding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound of the Formula (I) and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebulizer, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurized pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray Formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilizers, bacteriostats, suspending agents, thickening agents, and solutes which render the Formulation isotonic with the blood (or other relevant bodily fluid) of the intended recipient. Examples of excipients include, for example, water, alcohols, polyols, glycerol, vegetable oils, and the like. Examples of suitable isotonic carriers for use in such Formulations include Sodium Chloride Injection, Ringer's Solution, or Lactated Ringer's Injection. Typically, the concentration of the compound in the liquid is from about 1 ng/mL to about 10 µg/mL, for example, from about 10 ng/mL to about 1 µg/mL. The Formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In one embodiment, it will be appreciated by one of skill in the art that appropriate dosages of the compounds of the Formula (I), and compositions comprising the compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular 2-pyrrolopyrazole compound, the route of administration, the time of administration, the rate of excretion of the 2-pyrrolopyrazole compound, the duration of the treatment, other drugs, compounds, and/or materials used in combination, the severity of the condition, and the species, sex, age, weight, condition, general health, and prior medical history of the patient. The amount of 2-pyrrolopyrazole compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the Formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the 2-pyrrolopyrazole compound of the Formula (I) is in the range of about 50 µg to about 20 mg (more typically about 100 µg to about 10 mg) per kilogram body weight of the subject per day. Where the compound is a salt, an ester, an amide, a prodrug, or the like, the amount administered is calculated on the basis of the parent compound and so the actual weight to be used is increased proportionately In one embodiment, the compositions comprising a compound of the Formula (I) and another active agent may be administered simultaneously or sequentially, and may be administered in individually varying dose schedules and via different routes. For example, when administered sequentially, the compositions can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s). The compositions (i.e., the compound of the Formula (I), plus one or more other agents) may be formulated together in a single dosage form, or alternatively, the individual agents may be formulated separately and presented together in the form of a kit, optionally with instructions for their use.

The present disclosure also includes a kit comprising (a) an compound of the Formula (I) as described herein, or a composition comprising an compound as described herein, e.g., preferably provided in a suitable container and/or with suitable packaging; and (b) instructions for use, e.g., written instructions on how to administer the compound or composition.

In one embodiment, the kit further comprises one or more (e.g., 1, 2, 3, 4) additional therapeutic agents, as described herein.

The written instructions may also include a list of indications for which the active ingredient is a suitable treatment.

(IV) Processes for the Preparation of Compounds of the Formula (I)

Methods for the chemical synthesis of 2-pyrrolopyrazole compounds of the Formula (I) (as described herein) are described herein. These and/or other well-known methods may be modified and/or adapted in known ways in order to facilitate the synthesis of additional 2-pyrrolopyrazole compounds (as described herein).

In one embodiment a 2-substituted-1,4,5,6-tetrahydropyrrolo[3,4-c]pyrazole, can be prepared by the reaction of an appropriately-substituted hydrazine, e.g. prepared by reaction of a substituted benzyl chloride and hydrazine (see e.g., US2008/0255156), or by reductive amination of an appropriate aldehyde, with tert-butyl (34-3-[(dimethylamino)methylene]-4-oxopyrrolidine-1-carboxylate, prepared from reaction of commercially-available tert-butyl 3-oxopyrrolidine-1-carboxylate ("1-Boc-3-pyrroldinone") and N,N-dimethylformamide dimethylacetyl (DMF-DMA), in ethanol in a sealed tube (see e.g., WO2009/025784). The protecting group can then be removed under acidic conditions, e.g. using 4 M hydrochloric acid. An example of such a method is shown in Scheme 1.

Scheme 1

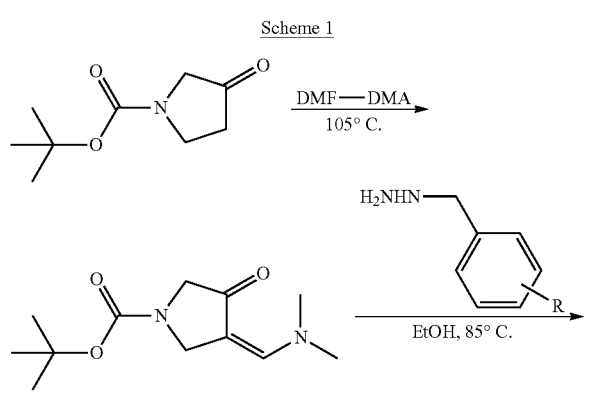

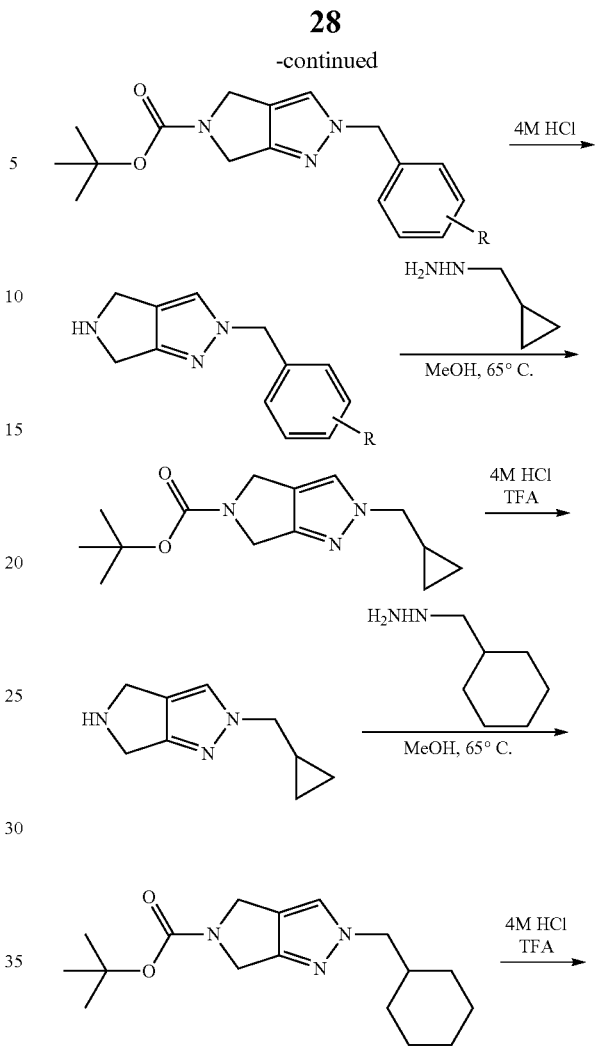

The 2-substituted-pyrrolopyrazole can then be reacted with the desired aryl or heteroaryl group, bearing a suitable leaving group, such as a halogen, in the presence of a suitable catalyst, e.g. Pd(OAc)$_2$, XPhos and Cs$_2$CO$_3$, to give the desired substitution on the pyrrole. An example of such a method is shown in Scheme 2.

Scheme 2

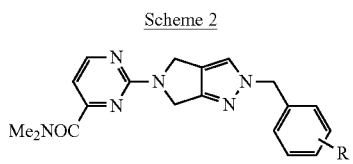

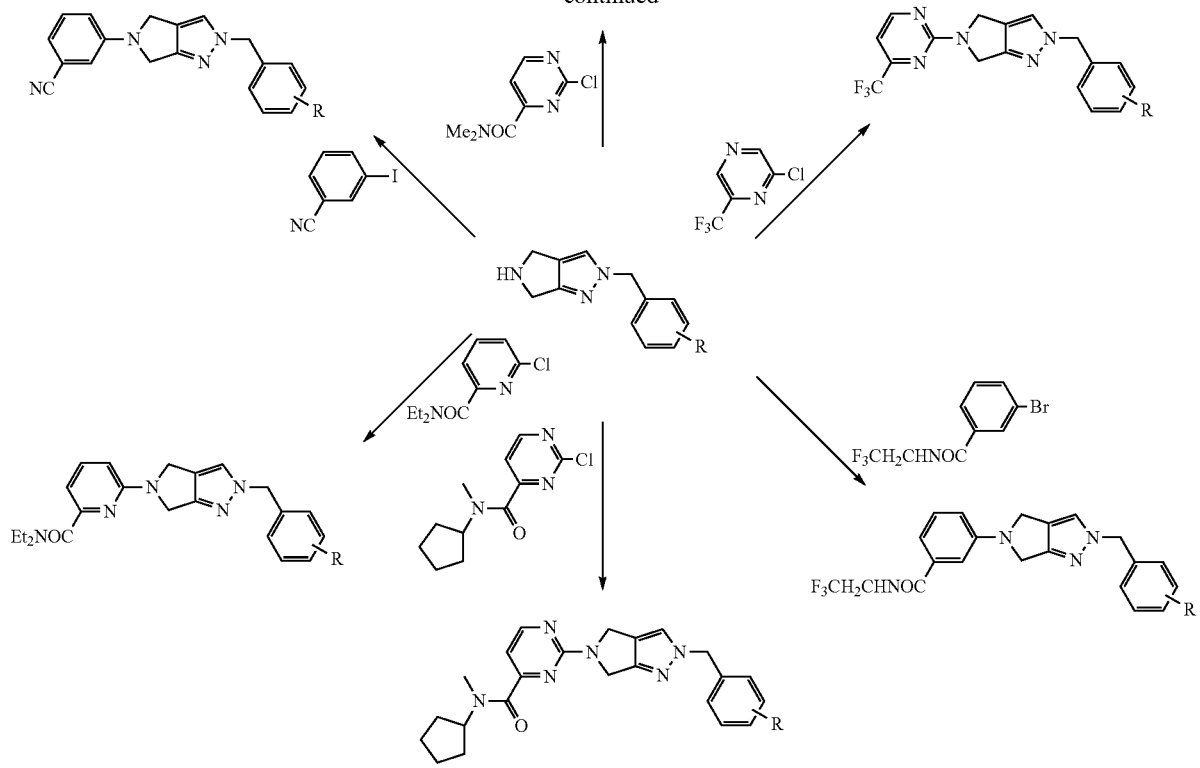

In another embodiment, the unsubstituted 1,4,5,6-tetrahydropyrrolo[3,4-c]pyrazole ("pyrrolopyrazole") skeleton can first be prepared, by reaction of tert-butyl (3Z)-3-[(dimethylamino)methylene]-4-oxopyrrolidine-1-carboxylate with hydrazine (see e.g., WO2011/146358) and then deprotected as described above. The pyrrolopyrazole can then be reacted on the pyrrole nitrogen with a suitable aryl or heteroaryl group as described above, then pyrazole can be deprotonated with a suitable base, e.g. NaH in THF, and reacted with a suitable benzyl bromide or benzyl chloride to give the desired product (as a mixture of regioisomers, which can be separated by high performance flash chromatography, see e.g., WO2009/025784). An example of such a method is shown in Scheme 3.

Scheme 3

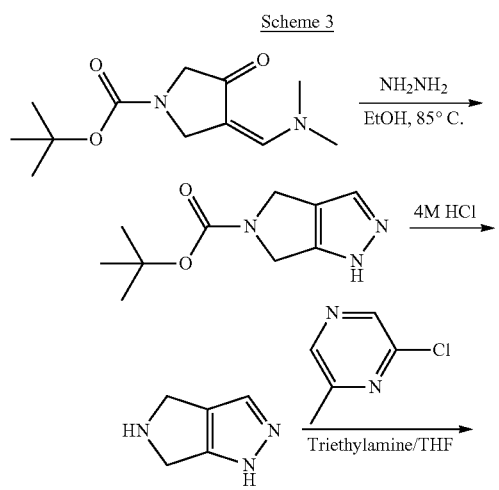

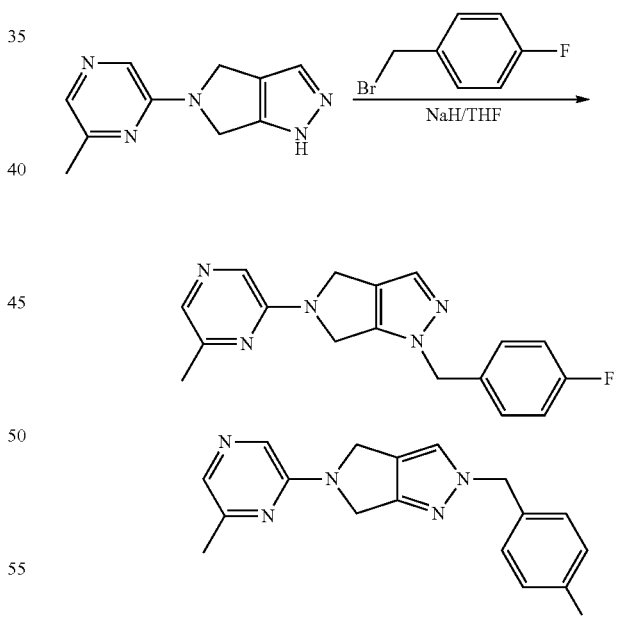

In another embodiment, the pyrrole-substituted 5-substituted-2,4,5,6-tetrahydropyrrolo[3,4-c]pyrazole skeleton can first be prepared, by reaction of tert-butyl (3Z)-3-[(dimethylamino)methylene]-4-oxopyrrolidine-1-carboxylate with hydrazine (see e.g., WO2011/146358) and then substituted on the pyrrazole as described above. An example of such a method is shown in Scheme 4.

Scheme 4

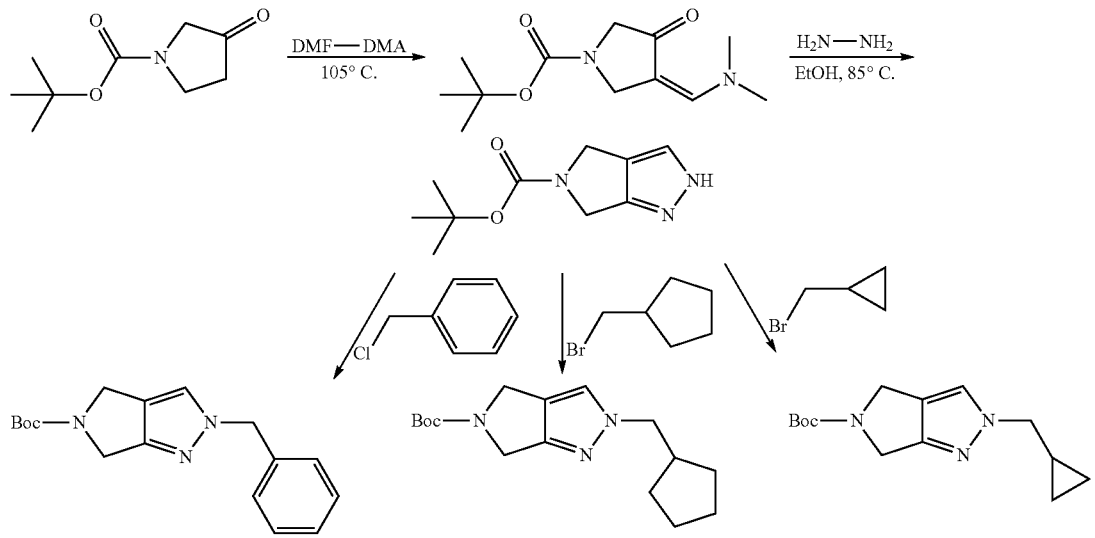

(V) Methods of Medical Treatment and Uses of the Compounds of the Formula (I)

In embodiments, the disclosure provides methods of modulating AMPA receptor signaling using the compounds of the Formula (I). In embodiments, the compounds of the Formula (I) modulate AMPA receptor signaling in vitro or in vivo. In embodiments, the compounds of the Formula (I) modulate AMPA receptor signaling by disrupting or reducing GluR2-GAPDH interaction. In embodiments, the compounds of Formula (I) inhibit AMPAR-mediated neurotoxicity, preferably without impairing AMPAR-mediated neurotransmission.

In embodiments, the disclosure provides methods of inhibiting the interaction between GluR2 and GAPDH, the methods comprising contacting a cell, in vitro or in vivo, preferably a neuron, with a compound of Formula (I).

In embodiments, the disclosure provides methods of inhibiting glutamate receptor mediated excitotoxicity without impairing AMPAR-mediated neurotransmission, the methods comprising contacting a cell, in vitro or in vivo, preferably a neuron, with a compound of Formula (I).

In embodiments, the disclosure provides methods of inhibiting glutamate receptor mediated excitotoxic calcium influx without impairing AMPAR-mediated neurotransmission, the methods comprising contacting a cell, in vitro or in vivo, preferably a neuron, with a compound of Formula (I).

In embodiments, the disclosure also provides methods for the treatment of a disease or condition in which modulation of AMPA receptor signaling is beneficial, such as to inhibit or reduce glutamate receptor mediated excitotoxicity, preferably without impairing AMPAR-mediated neurotransmission, the methods comprising administering to a patient in need thereof an effective amount of a compound of the Formula (I) as defined herein. In one embodiment, there is also included a method for the treatment of a disease or condition which is ameliorated by inhibiting glutamate receptor mediated excitotoxicity without impairing AMPAR-mediated neurotransmission, the method comprising administering to a patient in need thereof an effective amount of a compound of the Formula (I) as defined herein.

In another embodiment, there is also included a use of a compound of the Formula (I), optionally for the preparation of a medicament, wherein the compound or medicament is for treatment of a disease or condition in which modulation of AMPA receptor signaling to inhibit or reduce glutamate receptor mediated excitotoxicity is beneficial. In another embodiment, there is also included a use of a compound of the Formula (I), optionally for the preparation of a medicament, wherein the compound or medicament is for the treatment of a disease or condition which is ameliorated by inhibiting glutamate receptor mediated excitotoxicity without impairing AMPAR-mediated neurotransmission.

In embodiments, the disease or condition is one in which inappropriate AMPA receptor signaling is involved. In embodiments, the disease or condition is a neurological disease or disorder in which modulation of the interaction between GluR2 and glyceraldehyde-3-phosphate dehydrogenase is beneficial, or one in which modulation of AMPA receptor signaling to inhibit or reduce glutamate receptor mediated excitotoxicity is beneficial. In some embodiments, the neurological disease or disorder is characterized by excessive glutamate receptor-mediated excitotoxicity, including those characterized by GluR2/AMPAR neurotoxicity, including, but not limited to, neuroinflammation, amyotrophic lateral sclerosis (ALS), multiple sclerosis (MS), stroke, and epilepsy.

As discussed above, excessive glutamate, acting mainly through NMDARs and AMPARs, facilitates $Ca^{2+}$ influx, which can result in excitotoxicity under pathological conditions including ischemia, trauma, hypoglycemia and epileptic seizure. Glutamate receptor-mediated excitotoxicity is also involved in the demyelination, loss of neurons/oligodendrocytes and axonal damage that are responsible for the neurological deficits in multiple sclerosis (MS). The inhibition of calcium permeable AMPA receptors may be of benefit in treating MS. This is based on the observation that mice with Gria3 mutations that do not express functional GluR3 AMPA receptor subunits are resistant to demyelination and neurological sequelae in the EAE murine model of autoimmune encephalitis (EAE) which is the most common mouse model for MS. In contrast, mGluR4 knockout mice are more vulnerable to the EAE model, with more T-helper cells becoming the TH17 type that produce interleukin-17. Treatment with a selective mGluR4 enhancer appears to be protective against EAE through enhancement of regulatory Treg cells.

AMPA-mediated excitotoxity has also been implicated in other neurodegerative disorders, such as ALS (amyotrophic lateral sclerosis), in which motor neurons are primarily affected. Editing of the GluR2 mRNA is altered in spinal motor neurons from patients with ALS, leading to a higher proportion of Q/R site-unedited GluR-containing calcium permeable AMPA receptors.

Accordingly, the disclosure provides for the use of a compound of Formula (I), optionally for the preparation of a medicament, in treating a neurological disease or condition characterized by GluR2/AMPAR neurotoxicity.

In one embodiment, the disease or condition is multiple sclerosis or spasticity associated with multiple sclerosis.

In a further embodiment, the neurological disease or condition is neuroinflammation, a neurodegenerative disorder selected from Parkinson's disease, Alzheimer's disease, dementia, Huntington's disease, and amyotrophic lateral sclerosis (ALS).

In another embodiment, the condition is neuropathic pain, inflammatory pain, pain associated with multiple sclerosis, pain of undefined origin, pain associated with cancer or cancer chemotherapy, pain associated with diabetic neuropathy, or pain associated with surgery.

In another embodiment, the condition is an eating disorder such as cachexia or anorexia associated with cancer chemotherapy or cachexia or anorexia associated with HIV/AIDs.

In another embodiment, the inflammatory or autoimmune disease is rheumatoid arthritis, inflammatory bowel disease, psoriatic arthritis, chronic obstructive pulmonary disease, ankylosing spondylitis, an immune response leading to organ or graft rejection following transplant, or psoriasis.

In one embodiment, the psychiatric disorder is anxiety, including panic disorder, social anxiety disorder, and post-traumatic stress disorder. In embodiments, the psychiatric disorder is mania or schizophrenia.

In another embodiment of the disclosure, the compounds of the Formula (I) described herein may also be used as part of an in vitro assay, for example, in order to determine whether a candidate host is likely to benefit from treatment with the compound in question.

The 2-pyrrolopyrazole compound or pharmaceutical composition comprising the 2-pyrrolopyrazole compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray, drops or from an atomizer or dry powder delivery device); ocular (e.g., by eye drops); pulmonary (e.g., by inhalation or insufflation therapy using, e.g., an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

In one embodiment, the route of administration is oral (e.g., by ingestion).

In one embodiment, the route of administration is parenteral (e.g., by injection).

All references cited herein are incorporated by reference in their entirety.

EXAMPLES

The following examples are provided solely to illustrate the present disclosure and are not intended to limit the scope of the disclosure, as described herein.

Chemical Synthesis

Synthesis 1: tert-Butyl (Z)-3-((dimethylamino)methylene)-4-oxopyrrolidine-1-carboxylate (ZCN004)

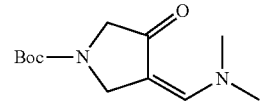

Using the method described by Biftu et al., (J. Med. Chem., 57, 3205-3212, 2014). to a solution of N-Boc-3-pyrrolidinone (11 g, 59.4 mmol), N,N-dimethylformamide dimethyl acetal (21.2 g, 178.2 mmol, 23.7 mL) in THF (20 mL) was stirred at 70° C. for 16 h. The reaction was cooled down to 23° C. and the solvent was evaporated under reduced pressure. The residue was triturated with hexane, filtered, washed with hexane and dried under reduced pressure. The resulting enamine ZCN004 as a yellow-orange powder (11.7 g, 82%), which was used for the next synthetic step without further purification. $^1$H NMR (400 MHz, CDCl$_3$) δ 7.32 (s, 1H), 4.59 (s, 2H), 3.82 (s, 2H), 3.11 (s, 6H), 1.49 (s, 9H). m/z (ESI) (relative intensity) 241.1 [M+H]$^+$ (100).

Synthesis 2: tert-Butyl 4,6-dihydropyrrolo[3,4-c]pyrazole-5(1H)-carboxylate (ZCN005)

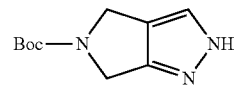

Using a modified method described by Chung et al., (Org. Process Res. Dev. 2015, 19 (11), 1760-1768) to a solution of enamine ZCAN004 (3.1 g, 12.9 mmol) in EtOH (10 mL) was added hydrazine hydrochloride (1.33 g, 19.4 mmol) at 23° C. The resulting suspension solution was stirred at 23° C. for 2 h before it was heated to 50° C. for 40 h. After which, the solvent was removed under reduced pressure and the residue was diluted with H$_2$O (20 mL). The aqueous phase was extracted with EtOAc (3×10 mL) and CH$_2$Cl$_2$ (3×10 mL). The combined organic layers were dried over Na$_2$SO$_4$ and concentrated in vacuo to afford compound ZCN005 (2.42 g, 90%) as an orange oil. ZCN005 was used for the next step without further purification. m/z (ESI) (relative intensity) 210.1 [M+H]$^+$ (100).

Synthesis 3: tert-butyl 2-(4-fluorobenzyl)-2,6-dihydropyrrolo[3,4-c]pyrazole-5(4H)-carboxylate (ZCN006b)

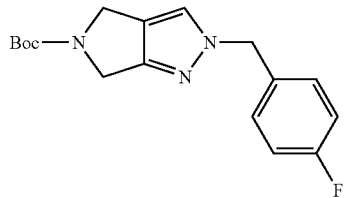 [SMILES: CC(C)(C)OC(=O)N1Cc2cn(Cc3ccc(F)cc3)nc2C1]

To a solution of compound ZCN005 (1.30 g, 6.2 mmol) in THF (5 mL) was added NaH (370 mg, 9.3 mmol, 60% in mineral oil) at 0° C. After stirring at 0° C. for 30 min, 1-(chloromethyl)-4-fluorobenzene (1.207 g, 1 mL, 8.35 mmol) was added. The resulting reaction mixture was stirred at 23° C. for 30 min and then heated to 50° C. for 24 h before it was quenched with a saturated solution of NH$_4$Cl (10 mL) at 0° C. and diluted with EtOAc (50 mL). The layers were separated, and the organic layer was extracted with H$_2$O (2×10 mL) and CH$_2$Cl$_2$ (2×10 mL). The combined organic layers were dried over Na$_2$SO$_4$ and concentrated in vacuo. The residue was purified by flash column chromatography (silica gel, hexanes:EtOAc 3:1→1:1) to give compounds ZCAN006a (946 mg, 48%) as an off-white amorphous solid and the desired regioisomer ZCN006b (784 mg, 40%) as a pale yellow oil. R$_f$ 0.32 (hexanes:EtOAc 1:1). TLC plate developed with KMnO$_4$ stain. ZCN006b: $^1$H NMR (400 MHz, CDCl$_3$) δ 7.23-7.18 (m, 2H), 7.15 (s, 0.5H), 7.12 (s, 0.5H), 7.01 (t, J=8.6 Hz, 2H), 5.24 (s, 2H), 4.49 (s, 1H), 4.43 (s, 2H), 4.40 (s, 1H), 1.50 (s, 9H); $^{19}$F NMR (376 MHz, CDCl$_3$) δ −114.03 (m, 0.5F), −114.07 (m, 0.5F). [N.B. rotamers present at 298 K]. m/z (ESI) (relative intensity) 318.2 [M+H]$^+$ (100).

Synthesis 4: 2-(4-fluorobenzyl)-2,4,5,6-tetrahydropyrrolo[3,4-c]pyrrazole (ZCN007b)

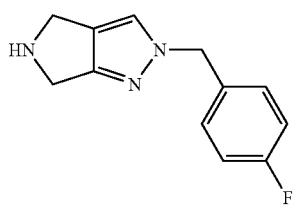 [SMILES: Fc1ccc(Cn2cc3c(n2)CNC3)cc1]

Method A: compound ZCN006b (714 mg, 2.25 mmol) was dissolved in 1,4-dioxane (8 mL) and 4N HCl (3 mL) was added at 0° C. After 5 h of stirring at 23° C., the solvent was removed under reduced pressure and the residue was triturated with Et$_2$O. Purification by flash column chromatography (silica gel, CH$_2$Cl$_2$:MeOH:NH$_4$OH$_{aq}$. 9.5:0.5:0.2 v/v) gave pyrrolopyrazole ZCN007b (486 mg, quantitative yield) as a pale yellow powder. R$_f$ 0.26 (CH$_2$Cl$_2$:MeOH: NH$_4$OH$_{aq}$. 9.5:0.5:0.2 v/v). TLC plate developed with KMnO$_4$ stain. $^1$H NMR (400 MHz, CDCl$_3$) δ 7.22 (dd, J=8.6, 5.5 Hz, 2H,), 7.08 (s, 1H), 7.04 (t, J=8.6 Hz, 2H), 5.24 (s, 2H), 4.04 (s, 2H), 4.02 (s, 2H), 2.78 (s, 1H); $^{13}$C NMR (100 MHz, CDCl$_3$) δ 162.4 (d, J$_{C-F}$=246.6 Hz), 160.4, 138.8 (d, J$_{C-F}$=3.3 Hz), 129.3 (d, J$_{C-F}$=8.2 Hz, 2×C), 124.3, 122.2, 115.7 (d, J$_{C-F}$=21.6 Hz, 2×C), 55.5, 44.9, 44.7; $^{19}$F (376 MHz, CDCl$_3$) δ −114.3. m/z (ESI) (relative intensity) 218.1 [M+H]$^+$ (100).

Synthesis 5: 6-(2-(4-Fluorobenzyl)-2,6-dihydropyrrolo[3,4-c]pyrazol-5(4H)-yl)-N,N-dimethylpyrazine-2-carboxamide (ZCN155)

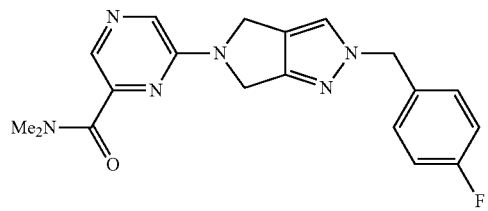

Method B: to a solution of pyrrolopyrazole ZCN007b (100 mg, 0.46 mmol) in 1,4-dioxane (3 mL) was added 6-chloro-N,N-dimethylpyrazine-2-carboxamide (94 mg, 0.51 mmol), Pd(OAc)$_2$ (5.2 mg, 0.023 mmol), XPhos (22 mg, 0.046 mmol) and Cs$_2$CO$_3$ (300 mg, 0.92 mmol) at 23° C. The resulting mixture was evacuated under vacuum and backfilled with nitrogen for 3 times prior to heat to 65° C. for 6 h. After which time, the reaction mixture was quenched with a saturated solution of NH$_4$Cl (10 mL) and diluted with EtOAc (20 mL). The layers were separated, and the organic layer was extracted with H$_2$O (3×10 mL). The combined organic layers were dried over Na$_2$SO$_4$ and concentrated in vacuo. The residue was purified by flash column chromatography (silica gel, hexanes:EtOAc 1:1→1:2) to give ZCN155 (120 mg, 71%) as an orange solid. $^1$H NMR (400 MHz, CDCl$_3$) δ 8.15 (s, 1H), 7.98 (s, 1H), 7.27-7.20 (m, 3H), 7.04 (t, J=8.6 Hz, 2H), 5.29 (s, 2H), 4.64 (s, 2H), 4.60 (s, 2H), 3.14 (s, 3H), 3.11 (s, 3H); $^{13}$C NMR (101 MHz, CDCl$_3$) δ 167.5, 162.5 (d, J$_{C-F}$=247.5 Hz), 154.5, 151.2, 147.1, 132.4 (d, J$_{C-F}$=3.4 Hz), 131.5, 130.4, 129.4 (d, J$_{C-F}$=9.2 Hz, 2×C), 123.0, 119.2, 115.8 (d, J$_{C-F}$=21.9 Hz, 2×C), 55.7, 46.1, 46.0, 38.9, 35.7; $^{19}$F NMR (376 MHz, CDCl$_3$) δ −113.86 (m, 1F). m/z (ESI) (relative intensity) 367.1 [M+H]$^+$ (100).

Synthesis 6: N-Cyclohexyl-2-(2-(4-fluorobenzyl)-2,6-dihydropyrrolo[3,4-c]pyrazol-5(4H)-yl)pyrimidine-4-carboxamide (ZCN209)

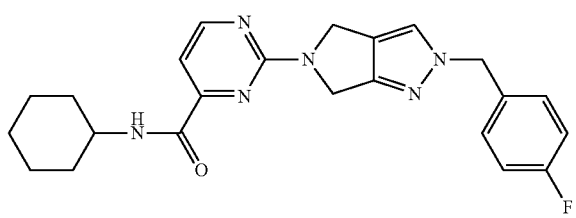 [SMILES: O=C(NC1CCCCC1)c1ccnc(N2Cc3cn(Cc4ccc(F)cc4)nc3C2)n1]

Using a method analogous to Method B, pyrrolopyrazole ZCN007b (40 mg, 0.18 mmol), 2-chloro-N-cyclohexylpyrimidine-4-carboxamide (49 mg, 0.20 mmol), Pd(OAc)$_2$ (2 mg, 8.9 μmol), XPhos (8.8 mg, 18.5 μmol) and Cs$_2$CO$_3$ (121 mg, 0.37 mmol) were used. Purification by flash column chromatography (silica gel, silica gel, hexanes:EtOAc 1:1) gave ZCN209 (64 mg, 83%) as a pale yellow oil. $^1$H NMR (400 MHz, CDCl$_3$) δ 8.58 (d, J=4.7 Hz, 1H), 7.88 (brs, 1H), 7.37 (d, J=4.8 Hz, 1H), 7.28-7.19 (m, 3H), 7.07 (t, J=8.7 Hz, 2H), 5.31 (s, 2H), 4.74 (s, 2H), 4.71 (s, 2H), 4.05-3.90 (m, 1H), 2.04-1.92 (m, 2H), 1.82-1.59 (m, 3H), 1.54-1.41 (m, 2H), 1.40-1.22 (m, 3H); $^{13}$C NMR (101 MHz, CDCl$_3$) δ 162.6 (d, $J_{C-F}$=247.2 Hz), 162.4, 160.2, 159.5, 157.3, 154.8, 132.5 (d, $J_{C-F}$=3.1 Hz), 129.7 (d, $J_{C-F}$=7.7 Hz, 2×C), 123.0, 119.5, 115.8 (d, $J_{C-F}$=21.7 Hz, 2×C), 106.8, 55.6, 47.9, 46.5, 46.1, 32.8 (2×C), 25.6, 24.6 (2×C); $^{19}$F NMR (376 MHz, CDCl$_3$) δ −113.88 (m, 1F). m/z (ESI) (relative intensity) 421.2 [M+H]$^+$ (100).

Synthesis 7: 2-(2-(4-Fluorobenzyl)-2,6-dihydropyrrolo[3,4-c]pyrazol-5(4H)-yl)-N,N-dimethylpyrimidine-4-carboxamide (ZCN210)

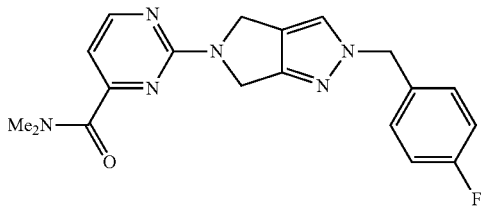

Using a method analogous to Method B, pyrrolopyrazole ZCN007b (42 mg, 0.19 mmol), 2-chloro-N,N-dimethylpyrimidine-4-carboxamide (40 mg, 0.22 mmol), Pd(OAc)$_2$ (2.2 mg, 9.8 μmol), XPhos (9.2 mg, 19.3 μmol) and Cs$_2$CO$_3$ (126 mg, 0.39 mmol) were used. Purification by flash column chromatography (silica gel, silica gel, hexanes:EtOAc 1:1→1:2) gave ZCN210 (48 mg, 68%) as a pale yellow oil. $^1$H NMR (400 MHz, CDCl$_3$) δ 8.46 (d, J=4.8 Hz, 1H), 7.25-7.18 (m, 4H), 7.03 (t, J=8.6 Hz, 2H), 5.27 (s, 2H), 4.71 (s, 1H), 4.67 (s, 1H), 4.65 (s, 2H), 3.11 (s, 3H), 3.09 (s, 3H); $^{13}$C NMR (101 MHz, CDCl$_3$) δ 167.7, 162.6 (d, $J_{C-F}$=246.1 Hz), 162.4, 160.2, 159.5, 154.8, 132.5 (d, $J_{C-F}$=2.8 Hz), 129.7 (d, $J_{C-F}$=9.4 Hz, 2×C), 123.0, 119.5, 115.8 (d, $J_{C-F}$=21.3 Hz, 2×C), 107.8, 55.7, 46.5, 46.2, 38.7, 35.4; $^{19}$F NMR (376 MHz, CDCl$_3$) δ −114.0 (m, 1F). m/z (ESI) (relative intensity) 367.2 [M+H]$^+$ (100).]

Synthesis 8: (2-(2-(4-Fluorobenzyl)-2,6-dihydropyrrolo[3,4-c]pyrazol-5(4H)-yl)pyrimidin-4-yl)(morpholino)methanone (ZCN211)

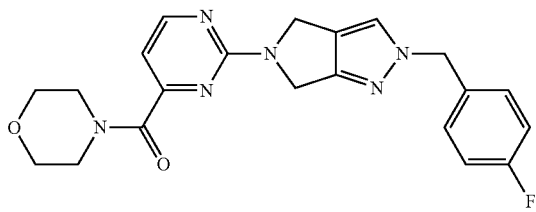

Using a method analogous to Method B, pyrrolopyrazole ZCN007b (54 mg, 0.25 mmol), (2-chloropyrimidin-4-yl)(morpholino)methanone (62 mg, 0.27 mmol), Pd(OAc)$_2$ (2.8 mg, 12.5 μmol), XPhos (12 mg, 25.2 μmol) and Cs$_2$CO$_3$ (162 mg, 0.50 mmol) were used. Purification by flash column chromatography (silica gel, silica gel, hexanes: EtOAc 1:1→1:2) gave ZCN211 (74 mg, 73%) as a pale yellow solid. $^1$H NMR (400 MHz, CDCl$_3$) δ 8.47 (d, J=5.2 Hz, 1H), 7.27-7.18 (m, 4H), 7.03 (t, J=8.4 Hz, 2H), 5.28 (s, 2H), 4.73 (s, 2H), 4.69 (s, 2H), 3.78 (s, 4H), 3.70 (dd, J=8.9, 4.1 Hz, 2H), 3.62 (dd, J=8.9, 4.1 Hz, 2H); $^{13}$C NMR (101 MHz, CDCl$_3$) δ 166.2, 162.5 (d, $J_{C-F}$=246.7 Hz), 161.3, 160.8, 159.4, 154.8, 132.6 (d, $J_{C-F}$=3.1 Hz), 129.8 (d, $J_{C-F}$=9.2 Hz, 2×C), 123.1, 119.4, 115.9 (d, $J_{C-F}$=22.1 Hz, 2×C), 108.3, 66.8, 66.2, 55.8, 47.5, 46.4, 46.0, 42.9; $^{19}$F NMR (376 MHz, CDCl$_3$) δ −114.2 (s, 1F). m/z (ESI) (relative intensity) 409.2 [M+H]$^+$ (100).

Synthesis 9: Methyl 2-(2-(4-fluorobenzyl)-2,6-dihydropyrrolo[3,4-c]pyrazol-5(4H)-yl)pyrimidine-4-carboxylate (ZCN008)

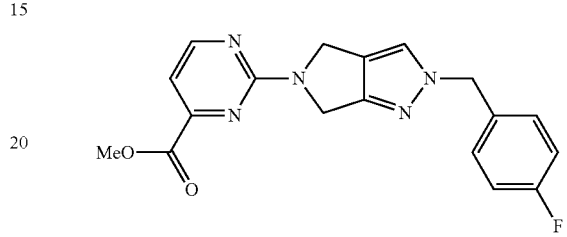

Using a method analogous to Method B, pyrrolopyrazole ZCN007b (100 mg, 0.46 mmol), methyl 2-chloropyrimidine-4-carboxylate (88 mg, 0.51 mmol), Pd(OAc)$_2$ (5.2 mg, 0.023 mmol), XPhos (22 mg, 0.046 mmol) and Cs$_2$CO$_3$ (300 mg, 0.92 mmol) were used. Purification by flash column chromatography (silica gel, silica gel, hexanes:EtOAc 1:1) gave ZCN008 (144 mg, 89%) as a pale yellow solid. $^1$H NMR (400 MHz, CDCl$_3$) δ 8.58 (d, J=4.8 Hz, 1H), 7.28-7.24 (m, 2H), 7.23-7.19 (m, 2H), 7.074 (t, J=8.5 Hz, 2H), 5.31 (s, 2H), 4.86-4.62 (m, 4H), 3.99 (s, 3H); $^{13}$C NMR (101 MHz, CDCl$_3$) δ 165.5, 162.2 (d, $J_{C-F}$=247.3 Hz), 162.2, 160.1, 159.4, 154.8, 132.4 (d, $J_{C-F}$=3.3 Hz), 129.6 (d, $J_{C-F}$=8.8 Hz, 2×C), 123.0, 119.4, 115.8 (d, $J_{C-F}$=22.0 Hz, 2×C), 109.1, 55.6, 53.0, 46.7, 46.2; $^{19}$F NMR (376 MHz, CDCl$_3$) δ −113.96 (m, 1F). m/z (ESI) (relative intensity) 354.1 [M+H]$^+$ (100).

Synthesis 10: 2-(2-(4-Fluorobenzyl)-2,6-dihydropyrrolo[3,4-c]pyrazol-5(4H)-yl)pyrimidine-4-carboxylic acid (ZCN009)

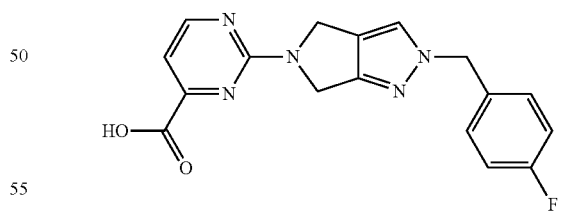

Method C: to a solution of ZCN008 (118 mg, 0.33 mmol) in THF (4 mL) was added a 20% aqueous solution of KOH (1 mL) at 23° C. The mixture was stirred at 70° C. for 4 h before it was quenched with a saturated solution of NH$_4$Cl (10 mL) and diluted with EtOAc (20 mL). The layers were separated, and the organic layer was extracted with H$_2$O (2×10 mL). The combined organic layers were dried over Na$_2$SO$_4$ and concentrated in vacuo to give the corresponding carboxylic acid ZCN009 as a white solid, which was used without further purification.

Synthesis 11: (2-(2-(4-Fluorobenzyl)-2,6-dihydropyrrolo[3,4-c]pyrazol-5(4H)-yl)pyrimidin-4-yl)(4-methylpiperazin-1-yl)methanone (ZCN212)

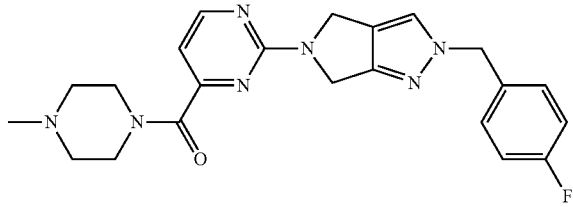 [SMILES: CN1CCN(C(=O)c2ccnc(N3Cc4cn(Cc5ccc(F)cc5)nc4C3)n2)CC1]

Method D: to a solution of carboxylic acid ZCN009 (42 mg, 0.124 mmol) in DMF (2 mL) was added 1-methylpiperazine (13.6 mg, 15 µL, 0.136 mmol), HATU (57 mg, 0.15 mmol) and DIPEA (42 mg, 55 µL, 0.325 mmol) at 23° C. The resulting mixture was stirred at 23° C. for 16 h before it was quenched with a saturated solution of $NH_4Cl$ (10 mL) and diluted with EtOAc (20 mL). The layers were separated, and the organic layer was extracted with $H_2O$ (2×5 mL). The combined organic layers were dried over $Na_2SO_4$ and concentrated in vacuo. Purification by flash column chromatography (silica gel, silica gel, EtOAc 100%) gave compound ZCN212 (31 mg, 59%) as a pale yellow solid. $^1$H NMR (400 MHz, $CDCl_3$) δ 8.49 (d, J=4.4 Hz, 1H), 8.03 (s, 1H), 7.28-7.21 (m, 3H), 7.05 (t, J=8.7 Hz, 2H), 5.29 (s, 2H), 4.78-4.55 (m, 4H), 3.86 (s, 2H), 3.72-3.64 (m, 2H), 2.71-2.52 (m, 4H), 2.44 (s, 3H); $^{13}$C NMR (101 MHz, $CDCl_3$) δ 167.8, 162.8 (d, $J_{C-F}$=244.2 Hz), 161.4, 160.7, 159.6, 154.7, 131.9 (d, $J_{C-F}$=3.4 Hz), 128.5 (d, $J_{C-F}$=8.8 Hz, 2×C), 123.1, 119.4, 115.8 (d, $J_{C-F}$=23.2 Hz, 2×C), 108.4, 55.4, 54.7, 54.3, 46.4, 45.7 (2×C), 45.6, 41.3; $^{19}$F NMR (376 MHz, $CDCl_3$) δ −113.98 (m, 1F). m/z (ESI) (relative intensity) 422.2 $[M+H]^+$ (100).

Synthesis 12: N-Cyclopentyl-2-(2-(4-fluorobenzyl)-2,6-dihydropyrrolo[3,4-c]pyrazol-5(4H)-yl)pyrimidine-4-carboxamide (ZCN213)

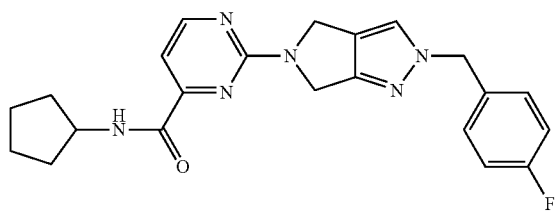

Using a method analogous to Method D, carboxylic acid ZCN009 (45 mg, 0.133 mmol), cyclopentanamine (13 mg, 15 µL, 0.153 mmol), HATU (61 mg, 0.160 mmol) and DIPEA (46 mg, 60 µL, 0.352 mmol) were used. Purification by flash column chromatography (silica gel, silica gel, hexane:EtOAc 1:1→1:2) gave compound ZCN213 (42 mg, 78%) as a pale yellow oil. $^1$H NMR (400 MHz, $CDCl_3$) δ $^1$H NMR (400 MHz, $CDCl_3$) δ 8.53 (d, J=4.6 Hz, 1H), 7.82 (brs, 1H), 7.37 (d, J=4.6 Hz, 1H), 7.28-7.21 (m, 3H), 7.06 (t, J=8.6 Hz, 2H), 5.32 (s, 2H), 4.74 (s, 2H), 4.71 (s, 2H), 4.28-4.13 (quint, J=7.2 Hz, 1H), 1.78-1.55 (m, 3H), 1.52-1.40 (m, 2H), 1.38-1.22 (m, 3H); $^{19}$F NMR (376 MHz, $CDCl_3$) δ −113.88 (m, 1F). m/z (ESI) (relative intensity) 407.2 $[M+H]^+$ (100).

Synthesis 13: Methyl 6-(2-(4-fluorobenzyl)-2,6-dihydropyrrolo[3,4-c]pyrazol-5(4H)-yl)pyrazine-2-carboxylate (ZCN010)

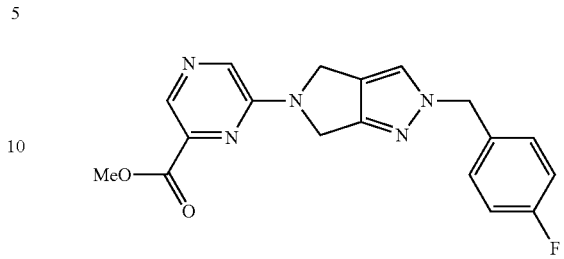

Using a method analogous to Method B, pyrrolopyrazole ZCN007b (120 mg, 0.55 mmol), methyl 6-chloropyrazine-2-carboxylate (106 mg, 0.61 mmol), $Pd(OAc)_2$ (6.3 mg, 0.028 mmol), XPhos (26.5 mg, 0.056 mmol) and $Cs_2CO_3$ (360 mg, 1.10 mmol) were used. Purification by flash column chromatography (silica gel, silica gel, hexanes:EtOAc 1:1) gave ZCN010 (160 mg, 82%) as a pale yellow solid. $^1$H NMR (400 MHz, $CDCl_3$) δ 8.59 (s, 1H), 8.14 (s, 1H), 7.29-7.22 (m, 3H), 7.07 (t, J=8.6 Hz, 2H), 5.32 (s, 2H), 4.72 (s, 2H), 4.70 (s, 2H), 4.00 (s, 3H); $^{13}$C NMR (101 MHz, $CDCl_3$) δ 165.5, 162.5 (d, $J_{C-F}$=245.5 Hz), 154.4, 152.3, 140.8, 132.3 (d, $J_{C-F}$=3.8 Hz), 131.5, 130.4, 129.5 (d, $J_{C-F}$=8.2 Hz, 2×C), 122.9, 119.2, 115.9 (d, $J_{C-F}$=23.4 Hz, 2×C), 55.7, 52.7, 46.3, 46.1; $^{19}$F NMR (376 MHz, $CDCl_3$) δ −113.80 (m, 1F). m/z (ESI) (relative intensity) 354.1 $[M+H]^+$ (100).

Synthesis 14: 6-(2-(4-Fluorobenzyl)-2,6-dihydropyrrolo[3,4-c]pyrazol-5(4H)-yl)pyrazine-2-carboxylic acid (ZCN011)

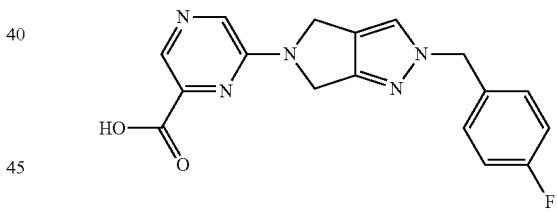

Using a method analogous to Method C, ZCN010 (103 mg, 0.29 mmol) was used to afford carboxylic acid ZCN011 as a white solid, which was used without further purification.

Synthesis 15: N-Cyclohexyl-6-(2-(4-fluorobenzyl)-2,6-dihydropyrrolo[3,4-c]pyrazol-5(4H)-yl)pyrazine-2-carboxamide (ZCN214)

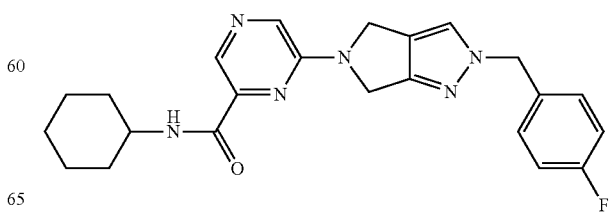

Using a method analogous to Method D, carboxylic acid ZCN011 (58 mg, 0.17 mmol), cyclohexylamine (19 mg, 22 μL, 0.192 mmol), HATU (78 mg, 0.205 mmol) and DIPEA (57 mg, 75 A, 0.441 mmol) were used. Purification by flash column chromatography (silica gel, silica gel, hexane:EtOAc 1:1→1:2) gave compound ZCN214 (50 mg, 70%) as a pale yellow oil. $^1$H NMR (400 MHz, CDCl$_3$) δ 8.14 (s, 1H), 7.96 (s, 1H), 7.84 (brs, 1H), 7.28-7.19 (m, 3H), 7.03 (t, J=8.8 Hz, 2H), 5.28 (s, 2H), 4.68 (s, 2H), 4.64 (s, 2H), 4.08-3.94 (m, 1H), 2.06-1.94 (m, 2H), 1.83-1.57 (m, 3H), 1.56-1.40 (m, 2H), 1.40-1.20 (m, 3H); $^{13}$C NMR (101 MHz, CDCl$_3$) δ 167.2, 162.6 (d, $J_{C-F}$=246.6 Hz), 154.5, 151.2, 147.1, 132.3 (d, $J_{C-F}$=3.2 Hz), 131.5, 130.4, 129.3 (d, $J_{C-F}$=9.4 Hz, 2×C), 123.0, 119.2, 115.9 (d, $J_{C-F}$=22.4 Hz, 2×C), 55.6, 48.1, 46.3, 46.0, 32.6 (2×C), 25.7, 24.3 (2×C); $^{19}$F NMR (376 MHz, CDCl$_3$) δ -113.84 (m, 1F). m/z (ESI) (relative intensity) 421.2 [M+H]$^+$ (100).

Synthesis 16: N-Cyclopentyl-3-(2-(4-fluorobenzyl)-2,6-dihydropyrrolo[3,4-c]pyrazol-5(4H)-yl)benzamide (ZCN215)

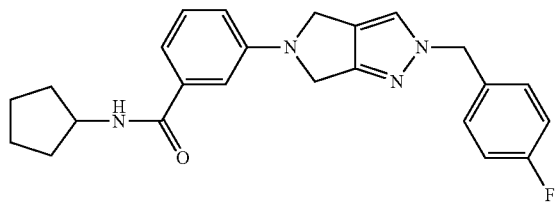 [SMILES: O=C(NC1CCCC1)c1cccc(N2Cc3cn(Cc4ccc(F)cc4)nc3C2)c1]

Using a method analogous to Method B, pyrrolopyrazole ZCN007b (50 mg, 0.23 mmol), 3-bromo-N-cyclopentylbenzamide (68 mg, 0.25 mmol), Pd(OAc)$_2$ (2.6 mg, 11.6 μmol), XPhos (11 mg, 23.1 μmol) and Cs$_2$CO$_3$ (150 mg, 0.46 mmol) were used. Purification by flash column chromatography (silica gel, silica gel, hexanes:EtOAc 1:1) gave compound ZCN215 (80 mg, 86%) as a pale yellow oil. $^1$H NMR (400 MHz, CDCl$_3$) δ 7.35-7.20 (m, 4H), 7.13 (t, J=2.4 Hz, 1H), 7.06 (t, J=8.6 Hz, 2H), 6.95 (d, J=8.1 Hz, 1H), 6.74 (dd, J=8.1, 2.4 Hz, 1H), 6.10 (br. d, J=7.2 Hz, 1H, NH), 5.30 (s, 2H), 4.49 (s, 2H), 4.46 (s, 2H), 4.42 (quint, J=7.2 Hz, 1H), 2.21-2.02 (m, 2H), 1.83-1.62 (m, 4H), 1.58-1.44 (m, 2H); $^{13}$C NMR (101 MHz, CDCl$_3$) δ 167.9, 162.5 (d, $J_{C-F}$=246.7 Hz), 155.4, 147.8, 136.2, 132.5 (d, $J_{C-F}$=3.3 Hz), 129.4 (d, $J_{C-F}$=8.3 Hz, 2×C), 129.3, 122.7, 119.9, 115.8 (d, $J_{C-F}$=22.6 Hz, 2×C), 113.9, 113.4, 110.4, 55.6, 51.7, 47.0, 46.8, 33.3 (2×C), 32.8 (2×C); $^{19}$F NMR (376 MHz, CDCl$_3$) δ -113.99 (m, 1F). m/z (ESI) (relative intensity) 405.2 [M+H]$^+$ (100).

Synthesis 17: N-Cyclohexyl-3-(2-(4-fluorobenzyl)-2,6-dihydropyrrolo[3,4-c]pyrazol-5(4H)-yl)benzamide (ZCN216)

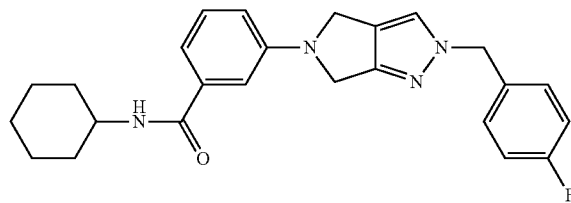

Using a method analogous to Method B, pyrrolopyrazole ZCN007b (30 mg, 0.14 mmol), 3-bromo-N-cyclohexylbenzamide (68 mg, 0.146 mmol), Pd(OAc)$_2$ (1.6 mg, 7.13 μmol), XPhos (6.6 mg, 13.8 μmol) and Cs$_2$CO$_3$ (90 mg, 0.276 mmol) were used. Purification by flash column chromatography (silica gel, silica gel, hexanes:EtOAc 1:1) gave compound ZCAN216 (51 mg, 88%) as a pale yellow oil. $^1$H NMR (400 MHz, CDCl$_3$) δ 7.37-7.18 (m, 4H), 7.13 (t, J=2.2 Hz, 1H), 7.07 (t, J=8.8 Hz, 2H), 6.97 (d, J=7.4 Hz, 1H), 6.74 (dd, J=8.6, 2.2 Hz, 1H), 6.01 (br. d, J=8.1 Hz, 1H, NH). 5.31 (s, 2H), 4.50 (s, 2H), 4.47 (s, 2H), 4.07-3.93 (m, 1H), 2.12-1.96 (m, 2H), 1.83-1.73 (m, 3H), 1.54-1.38 (m, 2H), 1.34-1.18 (m, 3H); $^{13}$C NMR (101 MHz, CDCl$_3$) δ 167.3, 162.5 (d, $J_{C-F}$=247.2 Hz), 155.4, 147.8, 136.4, 132.5 (d, $J_{C-F}$=3.6 Hz), 129.4 (d, $J_{C-F}$=7.9 Hz, 2×C), 129.3, 122.7, 120.0, 115.8 (d, $J_{C-F}$=21.5 Hz, 2×C), 113.9, 113.4, 110.4, 55.7, 48.7, 47.1, 46.9, 33.3 (2×C), 25.7, 24.9 (2×C); $^{19}$F NMR (376 MHz, CDCl$_3$) δ -114.00 (m, 1F). m/z (ESI) (relative intensity) 419.2 [M+H]$^+$ (100).

Synthesis 18: 3-(2-(4-Fluorobenzyl)-2,6-dihydropyrrolo[3,4-c]pyrazol-5(4H)-yl)-N,N-dimethylbenzamide (ZCN217)

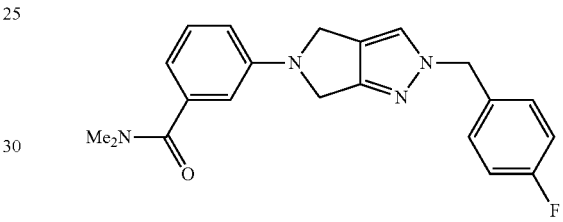

Using a method analogous to Method B, pyrrolopyrazole ZCN007b (30 mg, 0.14 mmol), 3-bromo-N,N-dimethylbenzamide (38 mg, 0.167 mmol), Pd(OAc)$_2$ (1.6 mg, 7.13 μmol), XPhos (6.6 mg, 13.8 μmol) and Cs$_2$CO$_3$ (90 mg, 0.276 mmol) were used. Purification by flash column chromatography (silica gel, silica gel, hexanes:EtOAc 1:1) gave compound ZCN217 (41 mg, 81%) as a pale yellow solid. $^1$H NMR (400 MHz, CDCl$_3$) δ 7.39-7.19 (m, 4H), 7.06 (t, J=8.8 Hz, 2H), 6.73 (dt, J=7.6, 1.1 Hz, 1H), 6.67 (d, J=1.1 Hz, 1H), 6.65 (dd, J=7.6, 1.1 Hz, 1H), 5.30 (s, 2H), 4.46 (s, 2H), 4.42 (s, 2H), 3.13 (s, 3H), 3.02 (s, 3H); $^{13}$C NMR (101 MHz, CDCl$_3$) δ 172.3, 162.5 (d, $J_{C-F}$=247.1 Hz), 155.4, 147.6, 137.5, 132.5 (d, $J_{C-F}$=3.2 Hz), 129.4 (d, $J_{C-F}$=8.2 Hz, 2×C), 129.2, 122.7, 119.9, 115.8 (d, $J_{C-F}$=22.1 Hz, 2×C), 114.5, 112.2, 109.7, 55.6, 47.0, 46.7, 39.6, 33.3; $^{19}$F NMR (376 MHz, CDCl$_3$) δ -114.01 (m, 1F). m/z (ESI) (relative intensity) 365.2 [M+H]$^+$ (100).

Synthesis 19: (3-(2-(4-Fluorobenzyl)-2,6-dihydropyrrolo[3,4-c]pyrazol-5(4H)-yl)phenyl)(4-methylpiperazin-1-yl)methanone (ZCN218)

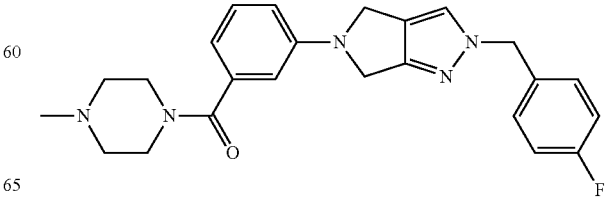

Using a method analogous to Method B, pyrrolopyrazole ZCN007b (30 mg, 0.14 mmol), (3-bromophenyl)(4-methylpiperazin-1-yl)methanone (47 mg, 0.166 mmol), Pd(OAc)$_2$ (1.6 mg, 7.13 μmol), XPhos (6.6 mg, 13.8 μmol) and Cs$_2$CO$_3$ (90 mg, 0.276 mmol) were used. Purification by flash column chromatography (silica gel, silica gel, hexanes:EtOAc 1:1→0:1) gave compound ZCN218 (36 mg, 62%) as a pale yellow solid. $^1$H NMR (400 MHz, CDCl$_3$) δ 7.40 (s, 1H), 7.33-7.19 (m, 3H), 7.04 (d, J=8.7 Hz, 2H), 6.70 (d, J=7.7 Hz, 1H), 6.68-6.62 (m, 2H), 5.28 (s, 2H), 4.45 (s, 2H), 4.40 (s, 2H), 3.88-3.71 (m, 2H), 3.56-3.34 (m, 2H), 2.54-2.43 (m, 2H), 2.41-2.28 (m+s, 5H); $^{13}$C NMR (101 MHz, CDCl$_3$) δ 170.9, 162.5 (d, J$_{C-F}$=246.0 Hz), 155.3, 147.6, 137.0, 132.5 (d, J$_{C-F}$=3.2 Hz), 129.4 (d, J$_{C-F}$=7.9 Hz, 2×C), 129.3, 122.7, 119.8, 115.7 (d, J$_{C-F}$=21.6 Hz, 2×C), 114.3, 112.4, 109.7, 55.6, 55.4, 54.7, 47.6, 47.0, 46.8, 46.0, 42.0; $^{19}$F NMR (376 MHz, CDCl$_3$) δ −113.99 (m, 1F). m/z (ESI) (relative intensity) 420.2 [M+H]$^+$ (100). [N.B. conformational isomers present at 298K, only the major conformer reported].

Synthesis 20: 3-(2-(4-Fluorobenzyl)-2,6-dihydropyrrolo[3,4-c]pyrazol-5(4H)-yl)-N-(2,2,2-trifluoroethyl)benzamide (ZCN219)

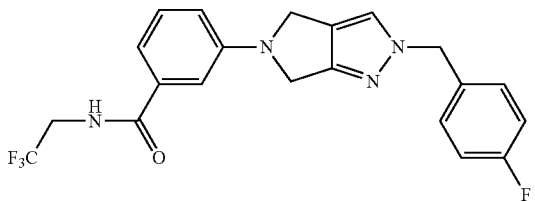 [SMILES: O=C(NCC(F)(F)F)c1cccc(N2Cc3cn(Cc4ccc(F)cc4)nc3C2)c1]

Using a method analogous to Method B, pyrrolopyrazole ZCN007b (30 mg, 0.14 mmol), 3-bromo-N-(2,2,2-trifluoroethyl)benzamide (47 mg, 0.167 mmol), Pd(OAc)$_2$ (1.6 mg, 7.13 μmol), XPhos (6.6 mg, 13.8 μmol) and Cs$_2$CO$_3$ (90 mg, 0.276 mmol) were used. Purification by flash column chromatography (silica gel, silica gel, hexanes:EtOAc 1:1→1:2) gave compound ZCN219 (51 mg, 89%) as a white solid. $^1$H NMR (400 MHz, CDCl$_3$) δ 7.34 (t, J=7.0 Hz, 1H), 7.29-7.18 (m, 3H), 7.13 (s, 1H), 7.11-6.98 (m, 3H), 6.79 (d, J=8.8 Hz, 1H), 6.49 (br. t, J=6.8 Hz, 1H, NH), 5.31 (s, 2H), 4.50 (s, 2H), 4.47 (s, 2H), 4.22-4.09 (m, 2H); $^{13}$C NMR (101 MHz, CDCl$_3$) δ 170.9, 162.5 (d, J$_{C-F}$=246.0 Hz), 155.3, 147.6, 137.0, 132.5 (d, J$_{C-F}$=3.2 Hz), 129.6, 129.4 (d, J$_{C-F}$=8.6 Hz, 2×C), 125.9 (q, J$_{C-F}$=277.3 Hz), 122.7, 119.8, 115.8 (d, J$_{C-F}$=21.3 Hz, 2×C), 114.9, 113.6, 110.4, 55.6, 47.0, 46.8, 40.8 (q, J$_{C-F}$=27.5 Hz); $^{19}$F NMR (376 MHz, CDCl$_3$) δ −72.27 (t, J=9.0 Hz, 3F), −113.93 (m, 1F). m/z (ESI) (relative intensity) 419.1 [M+H]$^+$ (100).

Synthesis 21: tert-Butyl 4-(3-(2-(4-fluorobenzyl)-2,6-dihydropyrrolo[3,4-c]pyrazol-5(4H)-yl)benzoyl)piperazine-1-carboxylate (ZCN012)

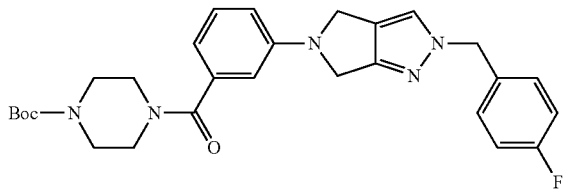 [SMILES: CC(C)(C)OC(=O)N1CCN(C(=O)c2cccc(N3Cc4cn(Cc5ccc(F)cc5)nc4C3)c2)CC1]

Using a method analogous to Method B, pyrrolopyrazole ZCN007b (30 mg, 0.14 mmol), tert-butyl 4-(3-bromobenzoyl)piperazine-1-carboxylate (61 mg, 0.165 mmol), Pd(OAc)$_2$ (1.6 mg, 7.13 μmol), XPhos (6.6 mg, 13.8 μmol) and Cs$_2$CO$_3$ (90 mg, 0.276 mmol) were used. Purification by flash column chromatography (silica gel, silica gel, hexanes:EtOAc 1:1→1:2) gave compound ZC012 (54 mg, 77%) as a pale yellow solid. $^1$H NMR (400 MHz, CDCl$_3$) δ 7.30 (d, J=7.9 Hz, 1H), 7.28-7.19 (m, 3H), 7.05 (d, J=8.8 Hz, 2H), 6.73-6.61 (m, 3H), 5.23 (s, 2H), 4.45 (s, 2H), 4.41 (s, 2H), 3.88-3.64 (m, 2H), 3.61-3.31 (m, 6H), 1.48 (s, 9H); $^{13}$C NMR (101 MHz, CDCl$_3$) δ 171.2, 162.4 (d, J$_{C-F}$=248.9 Hz), 155.3, 154.6, 147.7, 136.6, 132.5 (d, J$_{C-F}$=3.3 Hz), 129.5, 129.4 (d, J$_{C-F}$=8.4 Hz, 2×C), 122.7, 119.8, 115.8 (d, J$_{C-F}$=21.5 Hz, 2×C), 114.2, 112.6, 109.6, 80.3, 55.6, 47.5, 47.0, 46.8, 44.0, 43.3, 41.9, 28.4 (3×C); $^{19}$F NMR (376 MHz, CDCl$_3$) δ −72.27 (t, J=9.0 Hz, 3F), −113.96 (m, 1F). m/z (ESI) (relative intensity) 506.3 [M+H]$^+$ (100).

Synthesis 22: (3-(2-(4-Fluorobenzyl)-2,6-dihydropyrrolo[3,4-c]pyrazol-5(4H)-yl)phenyl)(piperazin-1-yl)methanone hydrochloride (ZCN220)

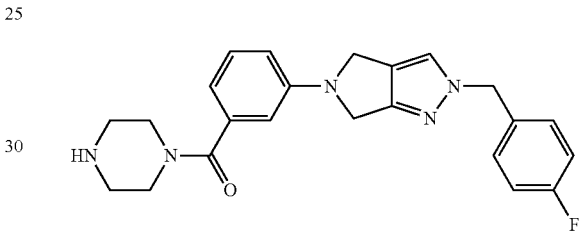

EtOH (5 mL) was cooled to 0° C. followed by adding acetyl chloride (1 mL) dropwise. The resulting solution was stirred at 0° C. for 20 min before a solution of compound ZCN012 (38 mg, 0.075 mmol) in EtOH (1 mL) was added. After stirring at 23° C. for 6 h, the solvent was removed under reduced pressure to give compound ZCN220 (30 mg, 90%) as a white solid. $^1$H NMR (400 MHz, MeOD-d$_4$) δ 7.61 (s, 1H), 7.41-7.25 (m, 3H), 7.09 (t, J=8.6 Hz, 2H), 6.83 (d, J=8.1 Hz, 1H), 6.78 (d, J=7.1 Hz, 1H), 6.75 (s, 1H), 5.36 (s, 2H), 4.46 (s, 4H), 3.67-3.58 (m, 6H), 3.36-3.28 (m, 2H); $^{13}$C NMR (101 MHz, MeOD-d$_4$) δ 170.1, 161.1 (d, J$_{C-F}$=245.9 Hz), 152.2, 145.5, 133.7, 130.8 (d, J$_{C-F}$=2.8 Hz), 128.1, 128.0 (d, J$_{C-F}$=8.9 Hz, 2×C), 123.9, 118.7, 113.9, 113.6 (d, J$_{C-F}$=21.8 Hz, 2×C), 112.5, 108.9, 56.8, 54.4 (3×C, 46.1 (2×C), 42.3; $^{19}$F NMR (376 MHz, MeOD-d$_4$) δ −116.00 (m, 1F). m/z (ESI) (relative intensity) 406.2 [M+H]$^+$ (100).

Synthesis 23: 3-(2-(4-Fluorobenzyl)-2,6-dihydropyrrolo[3,4-c]pyrazol-5(4H)-yl)-N-(2-methoxyethyl)benzamide (ZCN221)

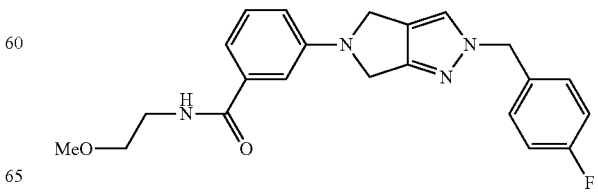

Using a method analogous to Method B, pyrrolopyrazole ZCN007b (30 mg, 0.14 mmol), 3-bromo-N-(2-methoxyethyl)benzamide (43 mg, 0.167 mmol), Pd(OAc)$_2$ (1.6 mg, 7.13 µmol), XPhos (6.6 mg, 13.8 µmol) and Cs$_2$CO$_3$ (90 mg, 0.276 mmol) were used. Purification by flash column chromatography (silica gel, silica gel, hexanes:EtOAc 1:1→1:2) gave compound ZCN221 (49 mg, 90%) as a white solid. $^1$H NMR (400 MHz, CDCl$_3$) δ 7.32 (t, J=7.8 Hz, 1H), 7.27-7.19 (m, 3H), 7.13 (d, J=2.2 Hz, 1H), 7.06 (t, J=8.6 Hz, 2H), 7.00 (d, J=8.6 Hz, 1H), 6.75 (dd, J=8.2, 2.2 Hz, 1H), 6.56 (br. t, J=5.6 Hz, 1H, NH), 5.31 (s, 2H), 4.50 (s, 2H), 4.46 (s, 2H), 3.68 (t, J=5.6 Hz, 2H), 3.59 (t, J=5.6 Hz, 2H), 3.41 (s, 3H); $^{13}$C NMR (101 MHz, CDCl$_3$) δ 168.2, 162.5 (d, J$_{C-F}$=248.5 Hz), 155.4, 147.8, 135.7, 132.5 (d, J$_{C-F}$=3.1 Hz), 129.43 (d, J$_{C-F}$=7.7 Hz, 2×C), 129.41, 122.7, 119.9, 115.8 (d, J$_{C-F}$=21.9 Hz, 2×C), 114.2, 113.8, 110.3, 71.3, 58.8, 55.6, 47.0, 46.8, 39.7; $^{19}$F NMR (376 MHz, CDCl$_3$) δ −72.27 (t, J=9.0 Hz, 3F), −113.99 (m, 1F). m/z (ESI) (relative intensity) 395.2 [M+H]$^+$ (100).

Synthesis 24: N-Cyclopentyl-2-(2-(4-fluorobenzyl)-2,6-dihydropyrrolo[3,4-c]pyrazol-5(4H)-yl)-N-methylpyrimidine-4-carboxamide (ZCN226)

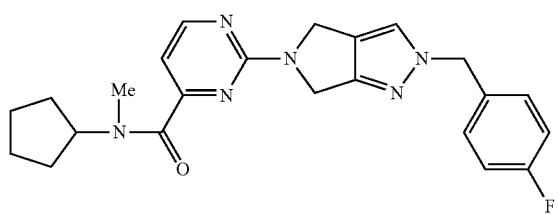

Using a method analogous to Method B, pyrrolopyrazole ZCN007b (32 mg, 0.147 mmol), 2-chloro-N-cyclopentyl-N-methylpyrimidine-4-carboxamide (42 mg, 0.175 mmol), Pd(OAc)$_2$ (1.7 mg, 7.57 µmol), XPhos (7.0 mg, 14.7 µmol) and Cs$_2$CO$_3$ (144 mg, 0.442 mmol) were used. Purification by flash column chromatography (silica gel, silica gel, hexanes:EtOAc 1:1→1:2) gave compound ZCN226 (49 mg, 79%) as an orange solid. m/z (ESI) (relative intensity) 421.2 [M+H]$^+$ (100). $^1$H NMR (400 MHz, CDCl$_3$) δ $^1$H NMR (400 MHz, CDCl$_3$) δ 8.46 (d, J=5.0 Hz, 1H), 7.27-7.18 (m, 4H), 7.04 (t, J=8.5 Hz, 2H), 5.29 (s, 2H), 4.77-4.56 (m, 4H), 3.98 (quintet, J=7.8 Hz, 1H), 2.97 (s, 3H), 1.86-1.58 (m, 3H), 1.57-1.41 (m, 2H), 1.39-1.22 (m, 3H); $^{19}$F NMR (376 MHz, CDCl$_3$) δ −113.98 (m, 1F). m/z (ESI) (relative intensity) 421.2 [M+H]$^+$ (100). [N.B. conformational isomers present at 298K, only the major conformer reported].

Synthesis 25: N-Cyclopentyl-6-(2-(4-fluorobenzyl)-2,6-dihydropyrrolo[3,4-c]pyrazol-5(4H)-yl)-N-methylpyrazine-2-carboxamide (ZCN228)

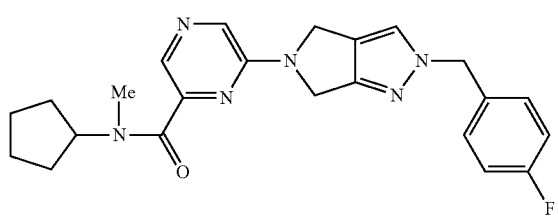 [SMILES: CN(C(=O)c1cncc(N2Cc3cn(Cc4ccc(F)cc4)nc3C2)n1)C1CCCC1]

Using a method analogous to Method B, pyrrolopyrazole ZCN007b (55 mg, 0.253 mmol), 6-chloro-N-cyclopentyl-N-methylpyrazine-2-carboxamide (73 mg, 0.305 mmol), Pd(OAc)$_2$ (2.8 mg, 12.5 µmol), XPhos (12.1 mg, 25.4 µmol) and Cs$_2$CO$_3$ (248 mg, 0.761 mmol) were used. Purification by flash column chromatography (silica gel, silica gel, hexanes:EtOAc 1:1→1:2) gave compound ZCN228 (88 mg, 83%) as an orange solid. m/z (ESI) (relative intensity) 421.2 [M+H]$^+$ (100). $^1$H NMR (400 MHz, MeOD-d$_4$) δ 8.09 (s, 1H), 7.95 (s, 1H), 7.60 (s, 1H), 7.35-7.25 (m, 2H), 7.07 (t, J=8.8 Hz, 2H), 5.33 (s, 2H), 4.68-4.59 (m, 4H), 4.31 (quintet, J=8.1 Hz, 1H), 3.00 (s, 3H), 2.08-1.92 (m, 2H), 1.88-1.59 (m, 2H), 1.57-1.41 (m, 2H), 1.40-1.18 (m, 2H); $^{19}$F NMR (376 MHz, MeOD-d$_4$) δ −113.80 (m, 1F). m/z (ESI) (relative intensity) 421.2 [M+H]$^+$ (100). [N.B. conformational isomers present at 298K, only the major conformer reported].

Synthesis 26: N-Cyclohexyl-2-(2-(4-fluorobenzyl)-2,6-dihydropyrrolo[3,4-c]pyrazol-5(4H)-yl)-N-methylpyrimidine-4-carboxamide (ZCN230)

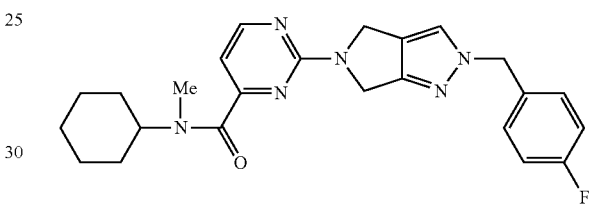

Using a method analogous to Method B, pyrrolopyrazole ZCN007b (35 mg, 0.161 mmol), 2-chloro-N-cyclohexyl-N-methylpyrimidine-4-carboxamide (49 mg, 0.193 mmol), Pd(OAc)$_2$ (1.8 mg, 8.0 µmol), XPhos (7.7 mg, 16.2 µmol) and Cs$_2$CO$_3$ (158 mg, 0.485 mmol) were used. Purification by flash column chromatography (silica gel, silica gel, hexanes:EtOAc 1:1→1:2) gave compound ZCN230 (58 mg, 83%) as a pale yellow solid. m/z (ESI) (relative intensity) 435.2 [M+H]$^+$ (100). $^1$H NMR (400 MHz, CDCl$_3$) δ 8.48 (d, J=5.2 Hz), 7.27-7.18 (m, 4H), 7.05 (t, J=8.7 Hz, 2H), 5.29 (s, 1H), 4.78-4.51 (m, 4H), 3.72-3.51 (m, 1H), 2.98 (s, 3H), 1.93-1.71 (m, 4H), 1.63-1.37 (m, 3H), 1.29-1.05 (m, 3H); $^{19}$F NMR (376 MHz, CDCl$_3$) δ −113.96 (s, 1F). m/z (ESI) (relative intensity) 435.2 [M+H]$^+$ (100). [N.B. conformational isomers present at 298K, only the major conformer reported].

Synthesis 27: N,N-Diethyl-6-(2-(4-fluorobenzyl)-2,6-dihydropyrrolo[3,4-c]pyrazol-5(4H)-yl)pyrazine-2-carboxamide (ZCN231)

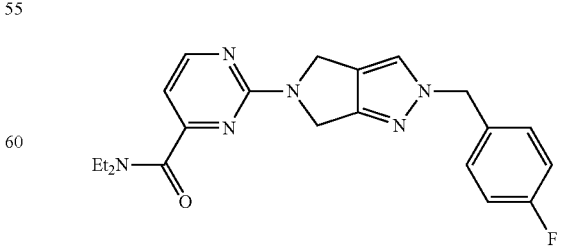

Using a method analogous to Method B, pyrrolopyrazole ZCN007b (52 mg, 0.24 mmol), 6-chloro-N,N-diethylpyrazine-2-carboxamide (62 mg, 0.29 mmol), Pd(OAc)₂ (2.7 mg, 12.0 μmol), XPhos (11.5 mg, 24.1 μmol) and Cs₂CO₃ (235 mg, 0.721 mmol) were used. Purification by flash column chromatography (silica gel, silica gel, hexanes:EtOAc 1:1→1:2) gave compound ZCN231 (81 mg, 86%) as a pale yellow solid. m/z (ESI) (relative intensity) 395.2 [M+H]⁺ (100). ¹H NMR (400 MHz, CDCl₃) δ 8.16 (s, 1H), 7.99 (s, 1H), 7.28-7.21 (m, 3H), 7.06 (t, J=8.6 Hz, 2H), 5.30 (s, 2H), 4.66 (s, 2H), 4.62 (s, 2H), 3.57 (q, J=7.1 Hz, 2H), 3.41 (q, J=7.1 Hz, 2H), 1.31-1.23 (m, 6H); ¹⁹F NMR (376 MHz, CDCl₃) δ −113.82 (s, 1F). m/z (ESI) (relative intensity) 395.2 [M+H]⁺ (100). [N.B. conformational isomers present at 298K, only the major conformer reported].

Synthesis 28: tert-butyl 2-(4-Methoxybenzyl)-2,6-dihydropyrrolo[3,4-c]pyrazole-5(4H)-carboxylate (ZCN018b)

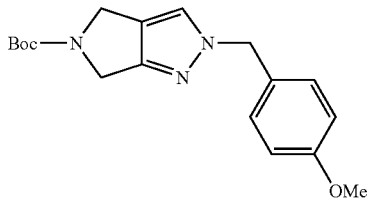 [SMILES: COc1ccc(Cn2cc3c(n2)CN(C(=O)OC(C)(C)C)C3)cc1]

To a solution of ZCN005 (280 mg, 1.34 mmol) in THF (3 mL) was added NaH (80 mg, 1.98 mmol, 60% in mineral oil) at 0° C. After stirring at 0° C. for 30 min, 1-(chloromethyl)-4-methoxybenzene (266 mg, 230 μL, 1.70 mmol) was added. The resulting reaction mixture was stirred at 23° C. for 30 min and then heated to 50° C. for 24 h before it was quenched with a saturated solution of NH₄Cl (10 mL) at 0° C. and diluted with EtOAc (50 mL). The layers were separated, and the organic layer was extracted with H₂O (2×10 mL) and CH₂Cl₂ (2×10 mL). The combined organic layers were dried over Na₂SO₄ and concentrated in vacuo. The residue was purified by flash column chromatography (silica gel, hexanes:EtOAc 3:1→1:1) to give compounds ZCN018a (194 mg, 44%) as an off-white amorphous solid and ZCN018b (163 mg, 37%) as a pale yellow oil. $R_f$=0.5 (Et₂O:hexanes 3:1×2). ¹H NMR (400 MHz, CDCl₃) δ 7.20 (d, J=7.4 Hz, 2H), 7.12 (s, 0.5H), 7.09 (s, 0.5H), 6.89 (d, J=8.6 Hz, 2H), 5.22 (s, 2H), 4.59-4.27 (m, 4H), 3.80 (s, 3H), 1.51 (s, 9H). m/z (ESI) (relative intensity) 330.2 [M+H]⁺ (100).

Synthesis 29: 2-(4-Methoxybenzyl)-2,4,5,6-tetrahydropyrrolo[3,4-c]pyrazole (ZCN019b)

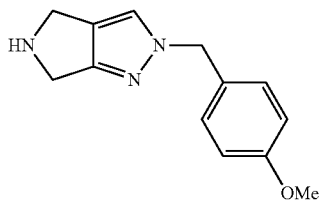 [SMILES: COc1ccc(Cn2cc3c(n2)CNC3)cc1]

Using a method analogous to Method A, ZCAN018b (152 mg, 0.46 mmol) and 4N HCl in 1,4-dioxane (2 mL) were used. Purification by flash column chromatography (silica gel, CH₂Cl₂:MeOH:NH₄OH_{aq}. 9.5:0.5:0.2 v/v) gave pyrrolopyrazole ZCAN019b (100 mg, 94%) as a pale yellow oil. m/z (ESI) (relative intensity) 230.1 [M+H]⁺ (100).

Synthesis 30: 6-(2-(4-Methoxybenzyl)-2,6-dihydropyrrolo[3,4-c]pyrazol-5(4H)-yl)-N,N-dimethylpyrazine-2-carboxamide (ZCN232)

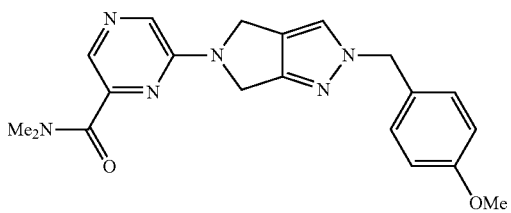 [SMILES: COc1ccc(Cn2cc3c(n2)CN(c2cncc(C(=O)N(C)C)n2)C3)cc1]

Using a method analogous to Method B, pyrrolopyrazole ZCAN019b (34 mg, 0.15 mmol), 6-chloro-N,N-dimethylpyrazine-2-carboxamide (30 mg, 0.16 mmol), Pd(OAc)₂ (1.7 mg, 7.6 μmol), XPhos (7.1 mg, 14.9 μmol) and Cs₂CO₃ (97 mg, 0.3 mmol) were used. Purification by flash column chromatography (silica gel, silica gel, hexanes:EtOAc 1:1→1:2) gave ZCAN232 (43 mg, 77%) as a pale yellow solid. ¹H NMR (400 MHz, CDCl₃) δ 8.17 (s, 1H), 7.99 (s, 1H), 7.25 (s, 1H), 7.22 (d, J=7.2 Hz, 2H), 6.91 (d, J=7.2 Hz, 2H), 5.27 (s, 2H), 4.65 (s, 2H), 4.61 (s, 2H), 3.82 (s, 3H), 3.16 (s, 3H), 3.13 (s, 3H); ¹³C NMR (101 MHz, CDCl₃) δ 167.6, 159.6, 154.2, 151.2, 147.1, 131.5, 130.4, 129.3 (2×C), 128.5, 122.7, 118.9, 114.3 (2×C), 56.0, 55.3, 46.2, 46.1, 38.9, 35.7. m/z (ESI) (relative intensity) 379.2 [M+H]⁺ (100).

Synthesis 31: 3-(2-(4-Methoxybenzyl)-2,6-dihydropyrrolo[3,4-c]pyrazol-5(4H)-yl)-N,N-dimethylbenzamide (ZCN233)

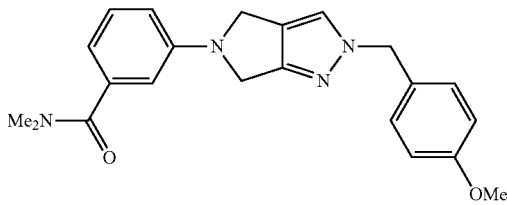 [SMILES: COc1ccc(Cn2cc3c(n2)CN(c2cccc(C(=O)N(C)C)c2)C3)cc1]

Using a method analogous to Method B, pyrrolopyrazole ZCAN019b (30 mg, 0.131 mmol), 3-bromo-N,N-dimethylbenzamide (33 mg, 0.145 mmol), Pd(OAc)₂ (1.5 mg, 6.7 μmol), XPhos (6.2 mg, 13.0 μmol) and Cs₂CO₃ (85 mg, 0.26 mmol) were used. Purification by flash column chromatography (silica gel, silica gel, hexanes:EtOAc 1:1→1:2) gave ZCAN233 (41 mg, 83%) as a pale yellow solid. ¹H NMR (400 MHz, CDCl₃) δ 7.28 (s, 1H), 7.25 (d, J=8.7 Hz, 2H), 7.19 (s, 1H), 6.91 (d, J=8.7 Hz, 2H), 6.73 (d, J=7.5 Hz, 1H), 6.69-6.63 (m, 2H), 5.27 (s, 2H), 4.47 (s, 2H), 4.41 (s, 2H), 3.82 (s, 3H), 3.14 (s, 3H), 3.02 (s, 3H); ¹³C NMR (101 MHz, CDCl₃) δ 172.3, 159.5, 155.1, 147.6, 137.5, 129.24 (2×C), 129.20, 128.7, 122.4, 119.7, 114.4, 114.3 (2×C), 112.2, 109.7, 55.9, 55.3, 47.0, 46.8, 39.6, 35.3. m/z (ESI) (relative intensity) 377.2 [M+H]⁺ (100).

Synthesis 32: tert-butyl 2-(4-Methylbenzyl)-2,6-dihydropyrrolo[3,4-c]pyrazole-5(4H)-carboxylate (ZCN020b)

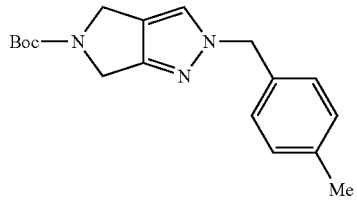 [SMILES: Cc1ccc(Cn2cc3c(n2)CN(C(=O)OC(C)(C)C)C3)cc1]

To a solution of ZCN005 (280 mg, 1.34 mmol) in THF (3 mL) was added NaH (80 mg, 1.98 mmol, 60% in mineral oil) at 0° C. After stirring at 0° C. for 30 min, 1-(chloromethyl)-4-methylbenzene (236 mg, 222 µL, 1.68 mmol) was added. The resulting reaction mixture was stirred at 23° C. for 30 min and then heated to 50° C. for 24 h before it was quenched with a saturated solution of NH$_4$Cl (10 mL) at 0° C. and diluted with EtOAc (50 mL). The layers were separated, and the organic layer was extracted with H$_2$O (2×10 mL) and CH$_2$Cl$_2$ (2×10 mL). The combined organic layers were dried over Na$_2$SO$_4$ and concentrated in vacuo. The residue was purified by flash column chromatography (silica gel, hexanes:EtOAc 3:1→1:1) to give compounds ZCN020a (171 mg, 41%) as an off-white amorphous solid and ZCN020b (144 mg, 34%) as a pale yellow oil. R$_f$=0.5 (EA:hexanes 1:2×2). $^1$H NMR (400 MHz, CDCl$_3$) δ 7.17-7.12 (m, 5H), 5.23 (s, 1H), 4.54-4.36 (m, 4H), 2.34 (s, 3H), 1.51 (s, 9H). m/z (ESI) (relative intensity) 314.2 [M+H]$^+$ (100).

Synthesis 33: 2-(4-Methylbenzyl)-2,4,5,6-tetrahydropyrrolo[3,4-c]pyrazole (ZCN021b)

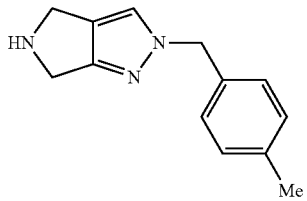 [SMILES: Cc1ccc(Cn2cc3c(n2)CNC3)cc1]

Using a method analogous to Method A, ZCN020b (122 mg, 0.39 mmol) and 4 N HCl in 1,4-dioxane (2 mL) were used. Purification by flash column chromatography (silica gel, CH$_2$Cl$_2$:MeOH:NH$_4$OH$_{aq}$. 9.5:0.5:0.2 v/v) gave pyrrolopyrazole ZCN021b (100 mg, 94%) as a pale yellow oil. m/z (ESI) (relative intensity) 214.1 [M+H]$^+$ (100).

Synthesis 34: N,N-Dimethyl-6-(2-(4-methylbenzyl)-2,6-dihydropyrrolo[3,4-c]pyrazol-5(4H)-yl)pyrazine-2-carboxamide (ZCN234)

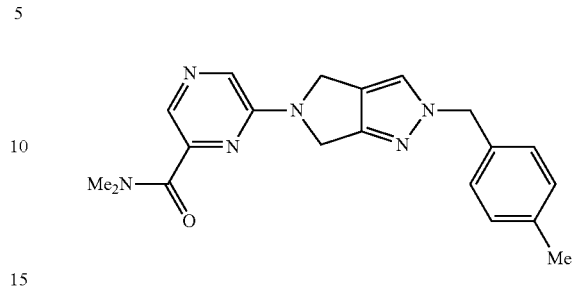

Using a method analogous to Method B, pyrrolopyrazole ZCN020b (36 mg, 0.17 mmol), 6-chloro-N,N-dimethylpyrazine-2-carboxamide (35 mg, 0.19 mmol), Pd(OAc)$_2$ (2.0 mg, 8.9 µmol), XPhos (8.0 mg, 16.7 µmol) and Cs$_2$CO$_3$ (110 mg, 0.34 mmol) were used. Purification by flash column chromatography (silica gel, silica gel, hexanes:EtOAc 1:1→1:2) gave compound ZCAN234 (38 mg, 63%) as a pale yellow solid. $^1$H NMR (400 MHz, CDCl$_3$) δ 8.15 (s, 1H), 7.98 (s, 1H), 7.23 (s, 1H), 7.20-7.09 (m, 4H), 5.29 (s, 2H), 4.64 (s, 2H), 4.60 (s, 2H), 3.15 (s, 3H), 3.12 (s, 3H), 2.34 (s, 3H); $^{13}$C NMR (101 MHz, CDCl$_3$) δ 167.5, 154.2, 151.2, 147.1, 138.0, 133.5, 131.5, 130.4, 129.6 (2×C), 127.8 (2×C), 122.9, 119.0, 56.3, 46.2, 46.1, 38.9, 35.7, 21.1. m/z (ESI) (relative intensity) 363.2 [M+H]$^+$ (100).

Synthesis 35: N,N-Dimethyl-3-(2-(4-methylbenzyl)-2,6-dihydropyrrolo[3,4-c]pyrazol-5(4H)-yl)benzamide (ZCN235)

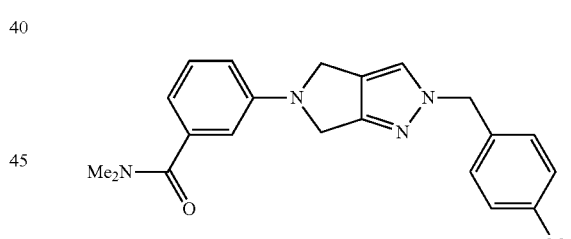

Using a method analogous to Method B, pyrrolopyrazole ZCN020b (45 mg, 0.21 mmol), 3-bromo-N,N-dimethylbenzamide (53 mg, 0.23 mmol), Pd(OAc)$_2$ (2.4 mg, 10.6 µmol), XPhos (10 mg, 20.9 µmol) and Cs$_2$CO$_3$ (138 mg, 0.42 mmol) were used. Purification by flash column chromatography (silica gel, silica gel, hexanes:EtOAc 1:1→1:2) gave compound ZCAN235 (58 mg, 76%) as a pale yellow solid. $^1$H NMR (400 MHz, CDCl$_3$) δ 7.32-7.25 (m, 1H), 7.21-7.12 (m, 6H), 6.74-6.70 (m, 1H), 6.69-6.60 (m, 2H), 5.28 (s, 2H), 4.46 (s, 2H), 4.40 (s, 2H), 3.13 (s, 3H), 3.02 (s, 3H), 2.35 (s, 3H); $^{13}$C NMR (101 MHz, CDCl$_3$) δ 172.4, 155.1, 147.6, 137.9, 137.5, 133.6, 129.6 (2×C), 129.2, 127.8 (2×C), 122.6, 119.7, 114.4, 112.2, 109.7, 56.2, 47.0, 46.8, 39.6, 35.3, 21.1. m/z (ESI) (relative intensity) 361.2 [M+H]$^+$ (100).

Synthesis 36: tert-butyl 2-(3-Fluorobenzyl)-2,6-dihydropyrrolo[3,4-c]pyrazole-5(4H)-carboxylate (ZCN022b)

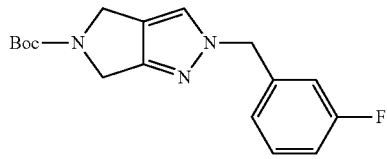 [SMILES: CC(C)(C)OC(=O)N1Cc2cn(Cc3cccc(F)c3)nc2C1]

To a solution of ZCN005 (360 mg, 1.72 mmol) in THF (6 mL) was added NaH (103 mg, 2.58 mmol, 60% in mineral oil) at 0° C. After stirring at 0° C. for 30 min, 1-(chloromethyl)-3-fluorobenzene (310 mg, 260 μL, 2.15 mmol) was added. The resulting reaction mixture was stirred at 23° C. for 30 min and then heated to 50° C. for 24 h before it was quenched with a saturated solution of $NH_4Cl$ (10 mL) at 0° C. and diluted with EtOAc (50 mL). The layers were separated, and the organic layer was extracted with $H_2O$ (2×10 mL) and $CH_2Cl_2$ (2×10 mL). The combined organic layers were dried over $Na_2SO_4$ and concentrated in vacuo. The residue was purified by flash column chromatography (silica gel, hexanes:EtOAc 3:1→1:1) to give compounds ZCN022a (256 mg, 47%) as an off-white amorphous solid and ZCN022b (169 mg, 31%) as a pale yellow oil. $R_f$=0.5 (EA:hexanes 1:2×2). $^1$H NMR (400 MHz, $CDCl_3$) δ 7.35-7.27 (m, 1H), 7.20-7.13 (m, 1H), 7.04-6.95 (m, 2H), 6.89 (d, J=9.4 Hz, 1H), 5.28 (s, 2H), 4.51 (s, 1H), 4.45 (s, 2H), 4.42 (s, 1H), 1.51 (s, 9H); $^{19}$F NMR (376 MHz, $CDCl_3$) δ −112.28 (m, 1F). m/z (ESI) (relative intensity) 318.2 [M+H]$^+$ (100).

Synthesis 37: 2-(3-Fluorobenzyl)-2,4,5,6-tetrahydropyrrolo[3,4-c]pyrazole (ZCN023b)

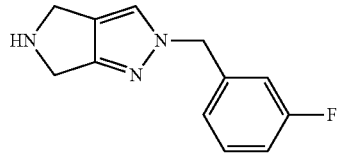 [SMILES: Fc1cccc(Cn2cc3c(n2)CNC3)c1]

Using a method analogous to Method A, ZCN022b (120 mg, 0.38 mmol) and 4N HCl in 1,4-dioxane (2 mL) were used. Purification by flash column chromatography (silica gel, $CH_2Cl_2$:MeOH:$NH_4OH_{aq.}$ 9.5:0.5:0.2 v/v) gave pyrrolopyrazole ZCN023b (76 mg, 93%) as a pale yellow oil. m/z (ESI) (relative intensity) 218.1 [M+H]$^+$ (100).

Synthesis 38: 6-(2-(3-Fluorobenzyl)-2,6-dihydropyrrolo[3,4-c]pyrazol-5(4H)-yl)-N,N-dimethylpyrazine-2-carboxamide (ZCN236)

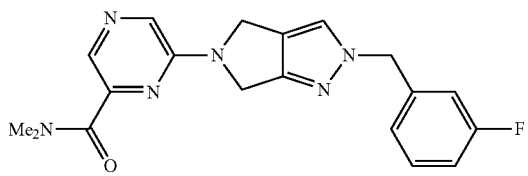 [SMILES: CN(C)C(=O)c1cncc(N2Cc3cn(Cc4cccc(F)c4)nc3C2)n1]

Using a method analogous to Method B, pyrrolopyrazole ZCN023b (62 mg, 0.258 mmol), 6-chloro-N,N-dimethylpyrazine-2-carboxamide (58 mg, 0.312 mmol), Pd(OAc)$_2$ (3.2 mg, 14.3 μmol), XPhos (13.6 mg, 28.5 μmol) and $Cs_2CO_3$ (186 mg, 0.57 mmol) were used. Purification by flash column chromatography (silica gel, silica gel, hexanes: EtOAc 1:1→1:2) gave compound ZCAN236 (49 mg, 47%) as a pale yellow solid. $^1$H NMR (400 MHz, $CDCl_3$) δ 8.16 (s, 1H), 7.99 (s, 1H), 7.37-7.30 (m, 2H), 7.29-7.26 (m, 1H), 7.06-6.97 (m, 1H), 6.92 (dd, J=8.4, 1.9 Hz, 1H), 5.33 (s, 2H), 4.66 (s, 2H), 4.63 (s, 2H), 3.15 (s, 3H), 3.13 (s, 3H); $^{13}$C NMR (101 MHz, $CDCl_3$) δ 167.5, 163.2 (d, J=247.1 Hz), 154.7, 151.2, 147.1, 139.7 (d, J=7.2 Hz), 139.1 (d, J=7.2 Hz), 131.6, 130.4, 123.2, 123.3 (d, J=3.0 Hz), 119.3, 115.1 (d, J=21.1 Hz), 114.5 (d, J=22.1 Hz), 55.8, 46.1, 46.0, 38.9, 35.7; $^{19}$F NMR (376 MHz, $CDCl_3$) δ −112.18 (m, 1F). m/z (ESI) (relative intensity) 367.2 [M+H]$^+$ (100).

Synthesis 39: 3-(2-(3-Fluorobenzyl)-2,6-dihydropyrrolo[3,4-c]pyrazol-5(4H)-yl)-N,N-dimethylbenzamide (ZCAN237)

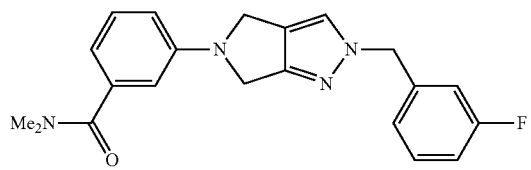 [SMILES: CN(C)C(=O)c1cccc(N2Cc3cn(Cc4cccc(F)c4)nc3C2)c1]

Using a method analogous to Method B, pyrrolopyrazole ZCN023b (55 mg, 0.253 mmol), 3-bromo-N,N-dimethylbenzamide (64 mg, 0.281 mmol), Pd(OAc)$_2$ (3.0 mg, 13.4 μmol), XPhos (12.0 mg, 25.2 μmol) and $Cs_2CO_3$ (165 mg, 0.51 mmol) were used. Purification by flash column chromatography (silica gel, silica gel, hexanes:EtOAc 1:1→1:2) gave compound ZCAN237 (66 mg, 72%) as a pale yellow solid. $^1$H NMR (400 MHz, $CDCl_3$) δ 7.36-7.22 (m, 3H), 7.07-6.96 (m, 2H), 6.92 (dt, J=8.1, 4.1 Hz, 1H), 6.73 (d, J=7.5 Hz, 1H), 6.65 (dd, J=8.6, 1.6 Hz, 2H), 5.31 (s, 2H), 4.46 (s, 2H), 4.42 (s, 2H), 3.12 (s, 3H), 3.01 (s, 3H); $^{13}$C NMR (101 MHz, $CDCl_3$) δ 172.3, 163.0 (d, J=247.0 Hz), 155.6, 147.6, 139.3 (d, J=7.1 Hz), 137.5, 130.5 (d, J=6.0 Hz), 130.30 (d, J=8.2 Hz), 129.2, 123.03 (d, J=3.0 Hz), 122.96, 120.0, 115.0 (d, J=21.1 Hz), 114.47, 114.46 (d, J=22.1 Hz), 112.2, 109.7, 55. 7, 47.0, 46.7, 39.6, 35.3; $^{19}$F NMR (376 MHz, $CDCl_3$) δ −112.27 (m, 1F). m/z (ESI) (relative intensity) 365.2 [M+H]$^+$ (100).

Synthesis 40: tert-butyl 2-(Cyclohexylmethyl)-2,6-dihydropyrrolo[3,4-c]pyrazole-5(4H)-carboxylate (ZCN024b)

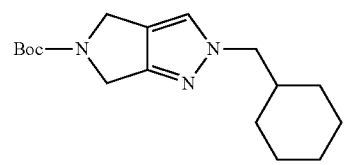 [SMILES: CC(C)(C)OC(=O)N1Cc2cn(CC3CCCCC3)nc2C1]

To a solution of ZCN005 (380 mg, 1.82 mmol) in THF (10 mL) was added NaH (145 mg, 3.63 mmol, 60% in mineral oil) at 0° C. After stirring at 0° C. for 30 min, (bromomethyl)

cyclohexane (482 mg, 380 µL, 2.72 mmol) was added. The resulting reaction mixture was stirred at 23° C. for 30 min and then heated to 50° C. for 24 h before it was quenched with a saturated solution of NH₄Cl (10 mL) at 0° C. and diluted with EtOAc (50 mL). The layers were separated, and the organic layer was extracted with H₂O (2×10 mL) and CH₂Cl₂ (2×10 mL). The combined organic layers were dried over Na₂SO₄ and concentrated in vacuo. The residue was purified by flash column chromatography (silica gel, hexanes:EtOAc 3:1→1:1) to give compounds ZCN024a (230 mg, 41%) as an off-white amorphous solid and ZCN024b (225 mg, 41%) as a pale yellow oil. $R_f$=0.5 (EA:hexanes 1:2×2). ¹H NMR (400 MHz, CDCl₃) δ 7.04 (s, 0.52H), 7.01 (s, 0.48H), 4.43 (s, 1H), 4.37 (d, J=3.6 Hz, 2H), 4.35 (s, 1H), 3.84 (d, J=7.1 Hz, 2H), 1.87-1.73 (m, 1H), 1.70-1.51 (m, 5H), 1.45 (d, J=1.3 Hz, 9H), 1.24-1.04 (m, 3H), 0.96-0.79 (m, 2H). [N.B. conformational isomers present at 298K]. m/z (ESI) (relative intensity) 306.2 [M+H]⁺ (100).

Synthesis 41: 2-(Cyclohexylmethyl)-2,4,5,6-tetrahydropyrrolo[3,4-c]pyrazole (ZCN025b)

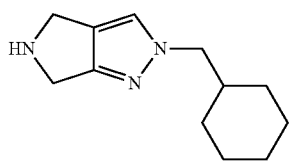 [SMILES: c1c2c(nn1CC1CCCCC1)CNC2]

Using a method analogous to Method A, compound ZCN024b (150 mg, 0.49 mmol) and 4N HCl in 1,4-dioxane (2 mL) were used. Purification by flash column chromatography (silica gel, CH₂Cl₂:MeOH:NH₄OH$_{aq}$. 9.5:0.5:0.2 v/v) gave pyrrolopyrazole ZCN025b (91 mg, 90%) as a pale yellow oil. m/z (ESI) (relative intensity) 206.2 [M+H]⁺ (100).

Synthesis 42: 6-(2-(Cyclohexylmethyl)-2,6-dihydropyrrolo[3,4-c]pyrazol-5(4H)-yl)-N,N-dimethylpyrazine-2-carboxamide (ZCN238)

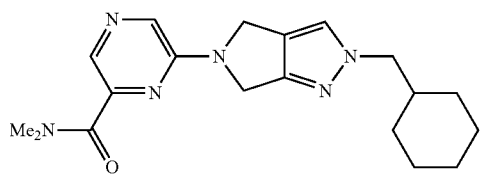 [SMILES: CN(C)C(=O)c1cncc(N2Cc3cn(CC4CCCCC4)nc3C2)n1]

Using a method analogous to Method B, pyrrolopyrazole ZCN025b (40 mg, 0.195 mmol), 6-chloro-N,N-dimethylpyrazine-2-carboxamide (40 mg, 0.216 mmol), Pd(OAc)₂ (2.2 mg, 9.8 µmol), XPhos (9.3 mg, 19.5 µmol) and Cs₂CO₃ (127 mg, 0.39 mmol) were used. Purification by flash column chromatography (silica gel, silica gel, hexanes: EtOAc 1:1→1:2) gave compound ZCAN238 (31 mg, 45%) as a pale yellow solid. ¹H NMR (400 MHz, CDCl₃) δ 8.16 (s, 1H), 7.98 (d, J=4.7 Hz, 1H), 7.18 (s, 1H), 4.64 (s, 2H), 4.62 (s, 2H), 3.96 (d, J=7.2 Hz, 2H), 3.15 (s, 3H), 3.13 (s, 3H), 1.97-1.82 (m, 1H), 1.81-1.55 (m, 5H), 1.36-1.11 (m, 3H), 1.03-0.95 (m, 2H); ¹³C NMR (101 MHz, CDCl₃) δ 167.6, 153.8, 151.2, 147.1, 131.5, 130.4, 123.3, 118.0, 59.1, 46.2, 46.1, 39.0, 38.9, 35.8, 30.7 (2×C), 26.3, 25.7 (2×C). m/z (ESI) (relative intensity) 355.2 [M+H]⁺ (100).

Synthesis 43: 3-(2-(Cyclohexylmethyl)-2,6-dihydropyrrolo[3,4-c]pyrazol-5(4H)-yl)-N,N-dimethylbenzamide (ZCN239)

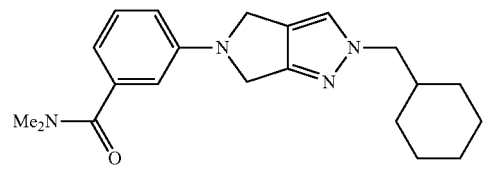

Using a method analogous to Method B, pyrrolopyrazole ZCN025b (65 mg, 0.317 mmol), 3-bromo-N,N-dimethylbenzamide (79 mg, 0.346 mmol), Pd(OAc)₂ (3.6 mg, 16.0 µmol), XPhos (15.1 mg, 31.7 µmol) and Cs₂CO₃ (206 mg, 0.63 mmol) were used. Purification by flash column chromatography (silica gel, silica gel, hexanes:EtOAc 1:1→1:2) gave compound ZCAN239 (67 mg, 60%) as a pale yellow solid. ¹H NMR (400 MHz, CDCl₃) δ 7.32-7.23 (m, 1H), 7.15 (s, 1H), 6.71 (d, J=7.5 Hz, 1H), 6.65 (s+d, J=6.9 Hz, 2H), 4.44 (s, 2H), 4.41 (s, 2H), 3.94 (d, J=7.1 Hz, 2H), 3.12 (s, 3H), 3.01 (s, 3H), 1.89 (ddd, J=10.9, 7.2, 3.4 Hz, 1H), 1.77-1.58 (m, 5H), 1.33-1.14 (m, 3H), 1.05-0.90 (m, 2H); ¹³C NMR (101 MHz, CDCl₃) δ 172.4, 154.7, 147.7, 137.5, 129.2, 123.0, 118.7, 114.3, 112.2, 109.7, 59.0, 47.0, 46.8, 39.6, 39.1, 35.2, 30.7 (2×C), 26.3, 25.7 (2×C). m/z (ESI) (relative intensity) 353.2 [M+H]⁺ (100).

Synthesis 44: 3-(2-(4-Fluorobenzyl)-2,6-dihydropyrrolo[3,4-c]pyrazol-5(4H)-yl)benzonitrile (ZCN240)

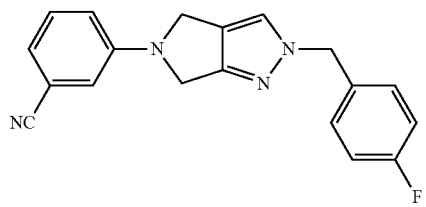 [SMILES: N#Cc1cccc(N2Cc3cn(Cc4ccc(F)cc4)nc3C2)c1]

Using a method analogous to Method B, pyrrolopyrazole ZCN007b (66 mg, 0.304 mmol), 3-bromobenzonitrile (69 mg, 0.379 mmol), Pd(OAc)₂ (3.4 mg, 15.1 µmol), XPhos (14.5 mg, 30.4 µmol) and Cs₂CO₃ (200 mg, 0.614 mmol) were used. Purification by flash column chromatography (silica gel, silica gel, hexanes:EtOAc 1:1→1:2) gave compound ZCAN240 (62 mg, 64%) as a white solid. ¹H NMR (400 MHz, CDCl₃) δ 7.37-7.31 (m, 1H), 7.30-7.22 (m, 3H), 7.10-7.03 (m, 2H), 7.00 (d, J=7.7 Hz, 1H), 6.84-6.78 (m, 2H), 5.31 (s, 2H), 4.44 (s, 2H), 4.41 (s, 2H); ¹³C NMR (101 MHz, CDCl₃) δ 162.6 (d, $J_{C-F}$=247.0 Hz), 154.8, 147.5, 132.4 (d, $J_{C-F}$=3.2 Hz), 130.1, 129.5 (d, $J_{C-F}$=8.3 Hz, 2×C), 122.8, 119.7, 119.5, 119.4, 115.8 (d, $J_{C-F}$=21.7 Hz, 2×C), 115.50, 114.0, 113.1, 55.7, 47.0, 46.8; ¹⁹F NMR (376 MHz, CDCl₃) δ −113.82 (m, 1F). m/z (ESI) (relative intensity) 319.1 [M+H]⁺ (100).

Synthesis 45: 2-(2-(4-Fluorobenzyl)-2,6-dihydropyrrolo[3,4-c]pyrazol-5(4H)-yl)pyrimidine-4-carbonitrile (ZCN241)

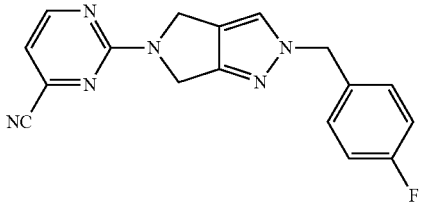 [SMILES: N#Cc1ccnc(N2Cc3cn(Cc4ccc(F)cc4)nc3C2)n1]

Using a method analogous to Method B, pyrrolopyrazole ZCN007b (70 mg, 0.322 mmol), 2-chloropyrimidine-4-carbonitrile (69 mg, 0.401 mmol), Pd(OAc)$_2$ (3.6 mg, 16.0 µmol), XPhos (15.4 mg, 32.3 µmol) and Cs$_2$CO$_3$ (210 mg, 0.644 mmol) were used. Purification by flash column chromatography (silica gel, silica gel, hexanes:EtOAc 1:1→1:2) gave compound ZCAN241 (72 mg, 70%) as a white solid. $^1$H NMR (400 MHz, CDCl$_3$) δ 8.55 (d, J=4.7 Hz, 1H), 7.29-7.21 (m, 3H), 7.16-7.00 (m, 2H), 6.86 (d, J=4.7 Hz, 1H), 5.31 (s, 2H), 4.72 (d, J=7.9 Hz, 2H), 4.67 (d, J=4.2 Hz, 2H); $^{13}$C NMR (101 MHz, CDCl$_3$) δ 162.2 (d, J$_{C-F}$=247.3 Hz), 160.1, 159.4, 154.8, 132.4 (d, J$_{C-F}$=3.3 Hz), 129.6 (d, J$_{C-F}$=8.8 Hz, 2×C), 123.0, 119.4, 115.8 (d, J$_{C-F}$=22.0 Hz, 2×C), 112.3, 109.5, 55.7, 46.7, 46.4; $^{19}$F NMR (376 MHz, CDCl$_3$) δ −113.83 (m, 1F). m/z (ESI) (relative intensity) 321.1 [M+H]$^+$ (100).

Synthesis 46: (3-(2-(4-Fluorobenzyl)-2,6-dihydropyrrolo[3,4-c]pyrazol-5(4H)-yl)phenyl)(piperidin-1-yl)methanone (ZCN242)

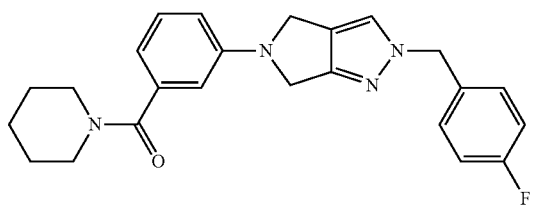 [SMILES: O=C(c1cccc(N2Cc3cn(Cc4ccc(F)cc4)nc3C2)c1)N1CCCCC1]

Using a method analogous to Method B, pyrrolopyrazole ZCN007b (70 mg, 0.322 mmol), 1-(3-bromobenzoyl)piperidine (108 mg, 0.403 mmol), Pd(OAc)$_2$ (3.6 mg, 16.0 µmol), XPhos (15.4 mg, 32.3 µmol) and Cs$_2$CO$_3$ (210 mg, 0.644 mmol) were used. Purification by flash column chromatography (silica gel, silica gel, hexanes:EtOAc 1:1→1:2) gave compound ZCAN242 (87 mg, 67%) as a pale yellow solid. $^1$H NMR (400 MHz, CDCl$_3$) δ 7.37-7.17 (m, 4H), 7.05 (t, J=8.6 Hz, 2H), 6.71 (d, J=7.4 Hz, 1H), 6.68-6.57 (m, 2H), 5.28 (s, 2H), 4.45 (s, 2H), 4.41 (s, 2H), 3.83-3.62 (m, 2H), 3.47-3.28 (m, 2H), 1.78-1.60 (m, 4H), 1.58-1.47 (m, 2H); $^{13}$C NMR (101 MHz, CDCl$_3$) δ 170.9, 162.5 (d, J=246.8 Hz), 155.4, 147.6, 137.7, 132.6 (d, J=3.2 Hz), 129.4 (d, J=8.2 Hz, 2×C), 129.3, 122.7 119.9 115.7 (d, J=21.6 Hz, 2×C), 114.2, 112.1, 109.5, 55.6, 48.8, 47.0, 46.8, 43.0, 26.6, 25.7, 24.7; $^{19}$F NMR (376 MHz, CDCl$_3$) δ −114.01 (m, 1F). m/z (ESI) (relative intensity) 405.2 [M+H]$^+$ (100).

Synthesis 47: (3-(2-(4-Fluorobenzyl)-2,6-dihydropyrrolo[3,4-c]pyrazol-5(4H)-yl)phenyl)(pyrrolidin-1-yl)methanone (ZCN243)

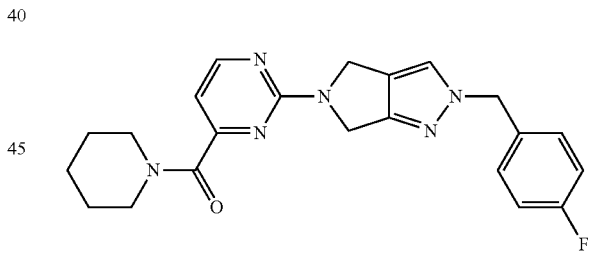

Using a method analogous to Method B, pyrrolopyrazole ZCN007b (85 mg, 0.391 mmol), (3-bromophenyl)(pyrrolidin-1-yl)methanone (105 mg, 0.413 mmol), Pd(OAc)$_2$ (4.4 mg, 19.6 µmol), XPhos (18.7 mg, 39.2 µmol) and Cs$_2$CO$_3$ (255 mg, 0.783 mmol) were used. Purification by flash column chromatography (silica gel, silica gel, hexanes:EtOAc 1:1→1:2) gave compound ZCAN243 (98 mg, 64%) as a pale yellow solid. $^1$H NMR (400 MHz, CDCl$_3$) δ 7.33-7.18 (m, 4H), 7.08-6.99 (m, 2H), 6.82 (d, J=7.6 Hz, 1H), 6.77 (d, J=2.1 Hz, 1H), 6.66 (dd, J=8.2, 2.1 Hz, 1H), 5.29 (s, 2H), 4.46 (s, 2H), 4.42 (s, 2H), 3.66 (t, J=6.7 Hz, 2H), 3.46 (t, J=6.7 Hz, 2H), 2.06-1.93 (m, 2H), 1.91-1.80 (m, 2H); $^{13}$C NMR (101 MHz, CDCl$_3$) δ 170.4, 162.5 (d, J=246.8 Hz), 155.4, 147.5, 138.4, 132.6 (d, J=3.3 Hz), 129.4 (d, J=8.2 Hz, 2×C), 129.1, 122.7, 119.9, 115.8 (d, J=21.7 Hz, 2×C), 114.6, 112.5, 109.9, 55.6, 49.6, 47.0, 46.8, 46.1, 26.4, 24.5; $^{19}$F NMR (376 MHz, CDCl$_3$) δ −114.01 (m, 1F). m/z (ESI) (relative intensity) 391.2 [M+H]$^+$ (100).

Synthesis 48: (2-(2-(4-Fluorobenzyl)-2,6-dihydropyrrolo[3,4-c]pyrazol-5(4H)-yl)pyrimidin-4-yl)(piperidin-1-yl)methanone (ZCN244)

Using a method analogous to Method B, pyrrolopyrazole ZCN007b (77 mg, 0.354 mmol), (2-chloropyrimidin-4-yl)(piperidin-1-yl)methanone (100 mg, 0.443 mmol), Pd(OAc)$_2$ (4.0 mg, 17.8 µmol), XPhos (17.0 mg, 35.7 µmol) and Cs$_2$CO$_3$ (231 mg, 0.709 mmol) were used. Purification by flash column chromatography (silica gel, silica gel, hexanes:EtOAc 1:1→1:2) gave compound ZCAN244 (76 mg, 53%) as a pale yellow solid. $^1$H NMR (400 MHz, CDCl$_3$) δ 8.46 (d, J=4.8 Hz, 1H), 7.28-7.16 (m, 3H), 7.12-6.95 (m, 2H), 6.82-6.62 (m, 1H), 5.29 (s, 2H), 4.82-4.44 (m, 4H), 3.71 (d, J=5.2 Hz, 2H), 3.52-3.32 (m, 2H), 1.80-1.54 (m, 6H); $^{13}$C NMR (101 MHz, CDCl$_3$) δ 166.2, 162.51 (d, J=246.8 Hz), 162.49, 159.6, 159.1, 155.0, 132.5 (d, J=3.2 Hz), 129.4 (d, J=8.2 Hz, 2×C), 122.9, 119.7, 115.8 (d, J=21.6 Hz, 2×C), 107.8, 55.6, 48.1, 46.5, 46.1, 43.0, 26.5, 25.6, 24.6; $^{19}$F NMR (376 MHz, CDCl$_3$) δ −113.99 (m, 1F). m/z (ESI) (relative intensity) 407.2 [M+H]$^+$ (100).

Synthesis 49: 6-(2-(4-Fluorobenzyl)-2,6-dihydropyrrolo[3,4-c]pyrazol-5(4H)-yl)pyrazine-2-carbonitrile (ZCN245)

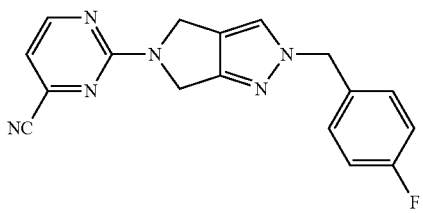

Using a method analogous to Method B, pyrrolopyrazole ZCN007b (80 mg, 0.368 mmol), 6-chloropyrazine-2-carbonitrile (64 mg, 0.459 mmol), Pd(OAc)$_2$ (4.0 mg, 17.8 µmol), XPhos (17.6 mg, 36.9 µmol) and Cs$_2$CO$_3$ (240 mg, 0.734 mmol) were used. Purification by flash column chromatography (silica gel, silica gel, hexanes:EtOAc 1:1→1:2) gave compound ZCAN245 (86 mg, 73%) as a pale yellow solid. $^1$H NMR (400 MHz, CDCl$_3$) δ 8.18 (s, 1H), 8.15 (s, 1H), 7.29-7.24 (m, 3H), 7.11-7.04 (m, 2H), 5.32 (s, 2H), 4.67 (s, 2H), 4.65 (s, 2H); $^{13}$C NMR (101 MHz, CDCl$_3$) δ 162.6 (d, J=247.2 Hz), 153.9, 152.1, 135.5, 133.8, 132.2 (d, J=3.2 Hz), 129.5 (d, J=8.2 Hz, 2×C), 127.9, 123.1, 118.7, 116.4, 115.9 (d, J=21.7 Hz, 2×C), 55.8, 46.31, 46.27; $^{19}$F NMR (376 MHz, CDCl$_3$) δ −113.64 (m, 1F). m/z (ESI) (relative intensity) 321.1 [M+H]$^+$ (100).

Synthesis 50: 4-(2-(4-Fluorobenzyl)-2,6-dihydropyrrolo[3,4-c]pyrazol-5(4H)-yl)-N,N-dimethylbenzamide (ZCN246)

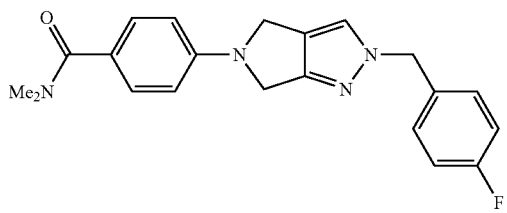 [SMILES: CN(C)C(=O)c1ccc(N2Cc3cn(Cc4ccc(F)cc4)nc3C2)cc1]

Using a method analogous to Method B, pyrrolopyrazole ZCN007b (40 mg, 0.184 mmol), 4-bromo-N,N-dimethylbenzamide (46 mg, 0.202 mmol), Pd(OAc)$_2$ (2.0 mg, 8.9 µmol), XPhos (8.8 mg, 18.5 µmol) and Cs$_2$CO$_3$ (120 mg, 0.368 mmol) were used. Purification by flash column chromatography (silica gel, silica gel, hexanes:EtOAc 1:1→1:2) gave compound ZCAN246 (49 mg, 73%) as a pale yellow solid. $^1$H NMR (400 MHz, CDCl$_3$) δ 7.47-7.42 (m, 2H), 7.28-7.21 (m, 3H), 7.12-6.99 (m, 2H), 6.65-6.57 (m, 2H), 5.31 (s, 2H), 4.49 (s, 2H), 4.45 (s, 2H), 3.10 (s, 6H); $^{13}$C NMR (101 MHz, CDCl$_3$) δ 172.2, 162.5 (d, J=246.9 Hz), 155.3, 148.6, 132.5 (d, J=3.3 Hz), 129.6, 129.4 (d, J=8.2 Hz, 2×C), 123.2, 122.7, 119.8, 115.8 (d, J=21.7 Hz, 2×C), 55.6, 47.0, 46.8, 39.9, 35.4; $^{19}$F NMR (376 MHz, CDCl$_3$) δ −113.99 (m, 1F). m/z (ESI) (relative intensity) 365.2 [M+H]$^+$ (100).

Synthesis 51: tert-butyl 2-(Cyclopropylmethyl)-2,6-dihydropyrrolo[3,4-c]pyrazole-5(4H)-carboxylate (ZCN026b)

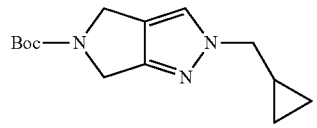 [SMILES: CC(C)(C)OC(=O)N1Cc2cn(CC3CC3)nc2C1]

To a solution of compound ZCN005 (180 mg, 0.86 mmol) in MeCN (5 mL) in a sealable tube was added (bromomethyl)cyclopropane (230 mg, 167 µL, 1.72 mmol) and Cs$_2$CO$_3$ (702 mg, 3.63 mmol). The sealed tube was heated to 70° C. for 24 h before it was quenched with a saturated solution of NH$_4$Cl (10 mL) and diluted with EtOAc (50 mL). The layers were separated, and the organic layer was extracted with H$_2$O (2×10 mL) and CH$_2$Cl$_2$ (2×10 mL). The combined organic layers were dried over Na$_2$SO$_4$ and concentrated in vacuo. The residue was purified by flash column chromatography (silica gel, hexanes:EtOAc 3:1→1:1) to give ZCN026b (141 mg, 62%; a mixture of regioisomers) as a pale yellow oil. A portion of regioisomers mixture (25 mg) was loaded on a plate TLC, which was developed under hexanes:EtOAc=1:1 for 3 times to afford compounds ZCN026a (12 mg) and ZCN026b (8 mg). R$_f$=0.5 (EA: hexanes 1:1×3). $^1$H NMR (400 MHz, CDCl$_3$) δ 7.24 (s, 0.56H), 7.20 (s, 0.44H), 4.49 (s, 1H), 4.46-4.39 (m, 3H), 3.96 (d, J=7.0 Hz, 2H), 1.50 (s, 9H), 1.31-1.21 (m, 1H), 0.69-0.59 (m, 2H), 0.41-0.30 (m, 2H).). [N.B. conformational isomers present at 298K]. m/z (ESI) (relative intensity) 264.2 [M+H]$^+$ (100).

Synthesis 52: 2-(Cyclopropylmethyl)-2,4,5,6-tetrahydropyrrolo[3,4-c]pyrazole (ZCN027b)

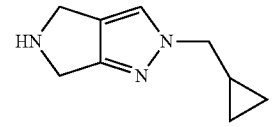 [SMILES: c1c2c(nn1CC1CC1)CNC2]

Using a method analogous to Method A, compound ZCN026b (116 mg, 0.44 mmol, a mixture of regioisomers) and 4N HCl in 1,4-dioxane (2 mL) were used. Purification by flash column chromatography (silica gel, CH$_2$Cl$_2$:MeOH: NH$_4$OH$_{aq}$. 9.5:0.5:0.2 v/v) gave pyrrolopyrazole ZCN027b (71 mg, quant. yield) as a pale yellow oil. m/z (ESI) (relative intensity) 164.1 [M+H]$^+$ (100).

Synthesis 53: 3-(2-(Cyclopropylmethyl)-2,6-dihydropyrrolo[3,4-c]pyrazol-5(4H)-yl)-N,N-dimethylbenzamide (ZCN247)

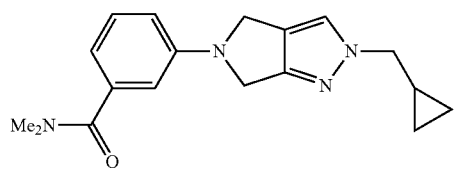 [SMILES: CN(C)C(=O)c1cccc(N2Cc3cn(CC4CC4)nc3C2)c1]

Using a method analogous to Method B, pyrrolopyrazole ZCN027b (70 mg, 0.429 mmol, a mixture of regioisomers), 4-bromo-N,N-dimethylbenzamide (108 mg, 0.473 mmol), Pd(OAc)$_2$ (4.8 mg, 21.4 μmol), XPhos (20.0 mg, 42.0 μmol) and Cs$_2$CO$_3$ (280 mg, 0.868 mmol) were used. Purification by flash column chromatography (silica gel, silica gel, hexanes:EtOAc 1:1→1:2) gave compound ZCAN247 (68 mg, 51%) as a pale yellow solid. $^1$H NMR (400 MHz, CDCl$_3$) δ 7.35-7.24 (m, 2H), 6.79-6.69 (m, 1H), 6.67-6.60 (m, 2H), 4.55-4.39 (m, 4H), 4.00 (dd, J=7.0, 4.4 Hz, 2H), 3.12 (s, 3H), 3.01 (s, 3H), 1.34-1.22 (m, 1H), 0.71-0.61 (m, 2H), 0.42-0.36 (m, 2H). m/z (ESI) (relative intensity) 311.2 [M+H]$^+$ (100).

Biological Studies

In Vivo Studies—Experimental Autoimmune Encephalomyelitis (EAE) Model for Multiple Sclerosis Induction of chronic relapsing EAE and neurological assessment. Female C57BL/6 mice (8-12 weeks of age) were purchased from Charles River Laboratories. Mice were injected subcutaneously (s.c.) in the back with 200 μL of recombinant MOG35-55 (200 μg, Biomatik Corporation, Cambridge, ON, Canada), which was emulsified in complete Freund's adjuvant (Sigma, Oakville, ON, Canada) and supplemented with 4 mg/mL Mycobacterium tuberculosis (strain H37R$^a$, BD Biosciences, Missisauga, ON, Canada) in four different sites (50 μL per site). Two hundred nanograms of pertussis toxin (List Biological Laboratories, Inc., Campbell, CA, USA) was injected intraperitoneally (i.p.) on days 0 and 2 after immunization. Mice were assessed daily for clinical signs of disease starting on the day of immunization. Clinical scoring was performed according to the following criteria: 0, asymptomatic; 0.5, distal paresis of the tail; 1, complete tail paralysis; 1.5, paresis of the tail and mild hind limb paresis; 2, unilateral severe hind limb paresis; 2.5, bilateral severe hind limb paresis; 3, complete bilateral hind limb paralysis; 3.5 complete bilateral hind limb paralysis paresis of one front limb; 4, complete paralysis (tetraplegia). All animal procedures used were in accordance with the approved Centre for Addiction and Mental Health animal research ethics committee protocol.

The FIGURE shows clinical scores of EAE mice treated with ZCN155 (synthesis 5; i.p. injection). Mice were split into three groups: No treatment group (n=6) and ZCN155 (Formula II; 5 or 10 mg/kg) i.p. injection administration group (n=6). EAE clinical symptom was scored daily. On Day 11~12, 1~2 days after the clinical symptoms started, ZCN155 was administrated by i.p. injection daily. The differences of the mean clinical score (means±s.e.m) is significantly lower in the ZCN155 group comparing with the no treatment group (two-way ANOVA, at least P<0.05). FIGURES and statistical analysis were done using Graphpad Prism 6.01. The results from the above EAE assay indicate that i.p. administration ZCN155 from day 11~12 after immunization (1~2 days after the presence of the symptoms) greatly improves neurological function.

In Vitro Studies—AMPA Mediated Cell-Death Assay

The ability of compounds to inhibit AMPA-mediated neurotoxicity was determined using the CellTox™ Green Cytotoxicity Assay (G8743) kit from Promega. In this assay, GAPDH and GluR2 are expressed in HEK-293 cells. AMPA (500 μM) was added to induce an AMPAR-mediated cell death signalling cascade. This is initiated by the GAPDH-GluR2 complex formation followed by the nuclear translocation of the complex, where it activates the p53-mediated cell death pathway. The presence of a compound which can block dimerization of GAPDH and GluR2 will prevent the nuclear translocation and the cell death and, thus this assay is an effective measure of the ability of a compound to prevent AMPA-mediated neurotoxicity and thus show therapeutic benefit in the treatment of MS.

The assay was performed as per the manufacture's instruction. Briefly, 293 cells stably expressing GluR1 and GluR2VENUS were transfected with pcDNA-RluC-GAPDH. AMPA (500 μM) were added to induce the cell death. CTZ (100 μM) was added to prevent AMPAR desensitization. Candidate molecules were added before the AMPA treatment to test its protective effect. Untreated cells and AMPA treated group were used as negative and positive control respectively. CellTox™ Green Reagent (~5×) was then added to achieve a final concentration of 1× and cells were incubated at room temperature for 15 minutes (shielded from ambient light). The fluorescence intensity at 485-500 nmEx/520-530 nmEm was then measured and calculated as the percentage value of the positive control. The concentration at which 50% of cell death was prevented (IC$_{50}$) was determined for each compound.

Biological Study 1

The potency was measured using the cell death assay described above. The results are summarized in Table 1.

TABLE 1

Inhibition of AMPA-mediated neurotoxicity

| Compound | Structure | Potency (nM) |
|---|---|---|
| REF | 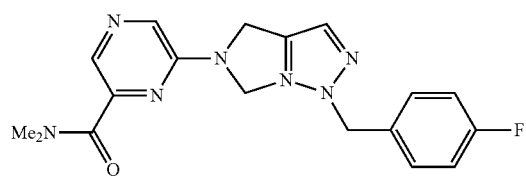 | 200 |

TABLE 1-continued

Inhibition of AMPA-mediated neurotoxicity

| Compound | Structure | Potency (nM) |
| --- | --- | --- |
| 155 | 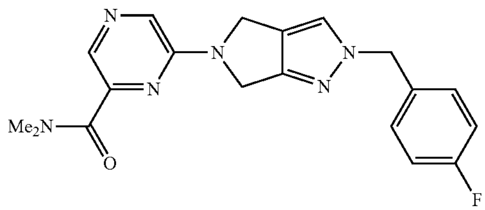 [SMILES: CN(C)C(=O)c1cncc(N2Cc3cn(Cc4ccc(F)cc4)nc3C2)n1] | 35 |
| 209 | 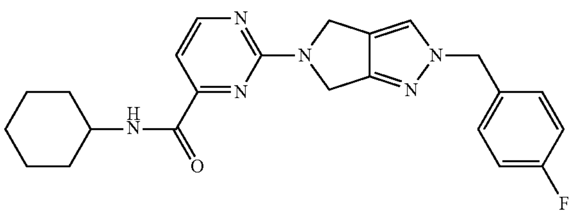 [SMILES: O=C(NC1CCCCC1)c1ccnc(N2Cc3cn(Cc4ccc(F)cc4)nc3C2)n1] | 66 |
| 210 | 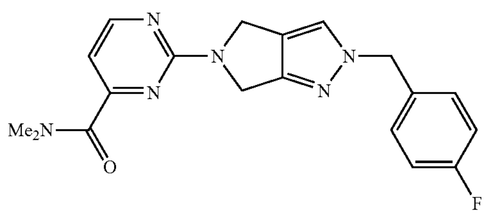 [SMILES: CN(C)C(=O)c1ccnc(N2Cc3cn(Cc4ccc(F)cc4)nc3C2)n1] | 82 |
| 211 | 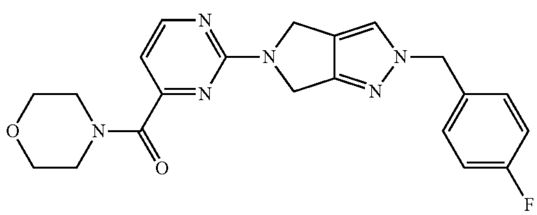 [SMILES: O=C(c1ccnc(N2Cc3cn(Cc4ccc(F)cc4)nc3C2)n1)N1CCOCC1] | 44 |
| 212 | 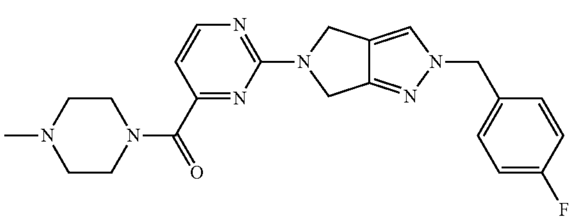 [SMILES: CN1CCN(C(=O)c2ccnc(N3Cc4cn(Cc5ccc(F)cc5)nc4C3)n2)CC1] | 20 |
| 213 | 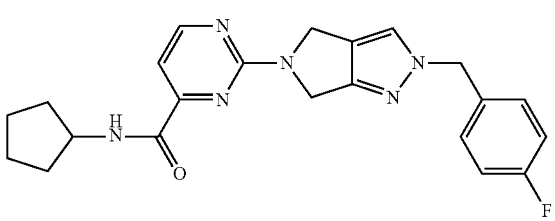 [SMILES: O=C(NC1CCCC1)c1ccnc(N2Cc3cn(Cc4ccc(F)cc4)nc3C2)n1] | 24 |
| 214 | 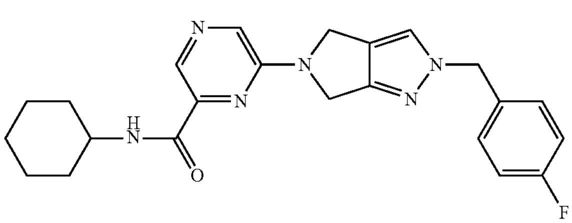 | 46 |

TABLE 1-continued

Inhibition of AMPA-mediated neurotoxicity

| Compound | Structure | Potency (nM) |
|---|---|---|
| 215 | (structure) | 3.5 |
| 216 | (structure) | 57 |
| 217 | (structure) | 6.7 |
| 218 | (structure) | 33 |
| 219 | (structure) | 28 |
| 220 | (structure) | 15 |
| 226 | (structure) | 42 |

TABLE 1-continued

Inhibition of AMPA-mediated neurotoxicity

| Compound | Structure | Potency (nM) |
| --- | --- | --- |
| 228 | 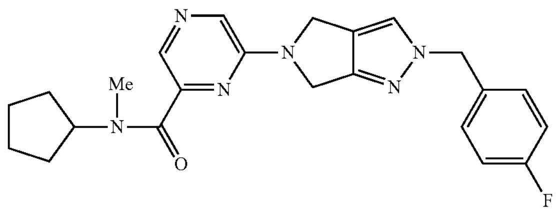 | 42 |
| 230 | 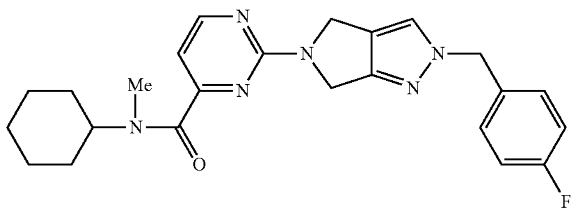 [SMILES: CN(C(=O)c1ccnc(N2Cc3cn(Cc4ccc(F)cc4)nc3C2)n1)C1CCCCC1] | 87 |
| 231 | 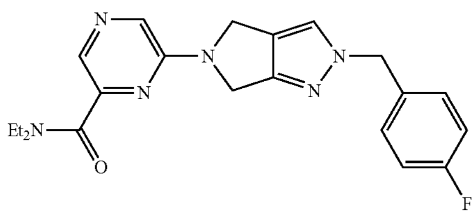 | 250 |
| 232 | 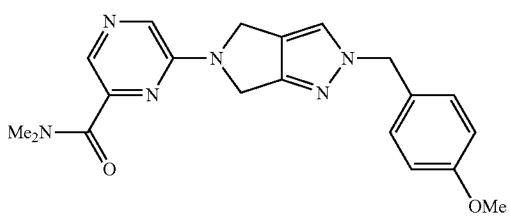 [SMILES: COc1ccc(Cn2cc3c(n2)CN(c2cncc(C(=O)N(C)C)n2)C3)cc1] | 54 |
| 233 | 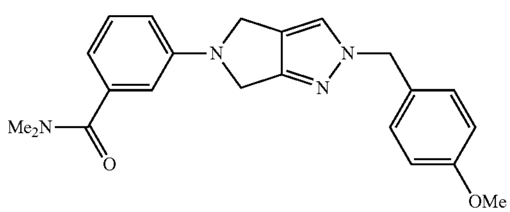 [SMILES: COc1ccc(Cn2cc3c(n2)CN(c2cccc(C(=O)N(C)C)c2)C3)cc1] | 62 |
| 234 | 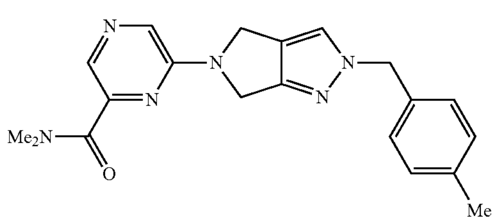 [SMILES: Cc1ccc(Cn2cc3c(n2)CN(c2cncc(C(=O)N(C)C)n2)C3)cc1] | 114 |
| 235 | 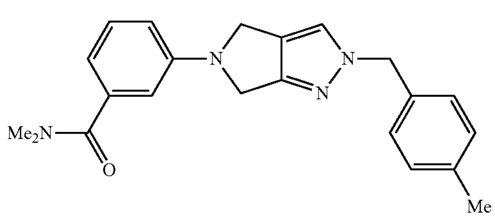 [SMILES: Cc1ccc(Cn2cc3c(n2)CN(c2cccc(C(=O)N(C)C)c2)C3)cc1] | 656 |

TABLE 1-continued

Inhibition of AMPA-mediated neurotoxicity

| Compound | Structure | Potency (nM) |
|---|---|---|
| 236 | 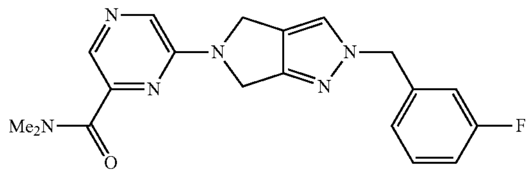 [SMILES: CN(C)C(=O)c1cncc(N2Cc3cn(Cc4cccc(F)c4)nc3C2)n1] | 5000 |
| 237 | 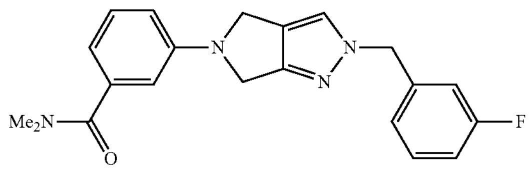 [SMILES: CN(C)C(=O)c1cccc(N2Cc3cn(Cc4cccc(F)c4)nc3C2)c1] | 47 |
| 238 | 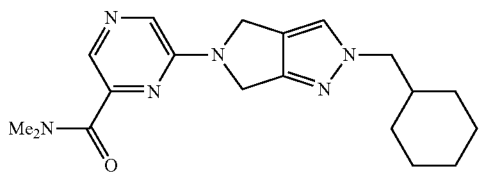 [SMILES: CN(C)C(=O)c1cncc(N2Cc3cn(CC4CCCCC4)nc3C2)n1] | 167 |
| 239 | 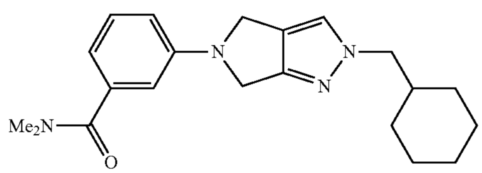 [SMILES: CN(C)C(=O)c1cccc(N2Cc3cn(CC4CCCCC4)nc3C2)c1] | 26 |
| 240 | 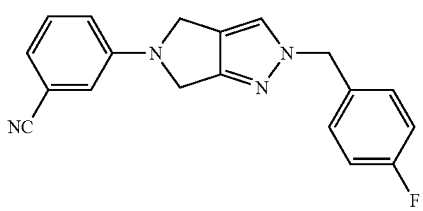 [SMILES: N#Cc1cccc(N2Cc3cn(Cc4ccc(F)cc4)nc3C2)c1] | 35 |
| 241 | 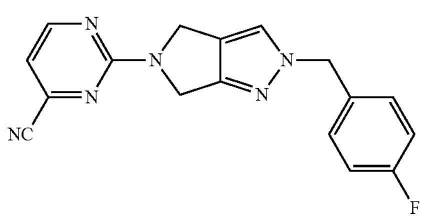 [SMILES: N#Cc1ccnc(N2Cc3cn(Cc4ccc(F)cc4)nc3C2)n1] | 72 |
| 242 | 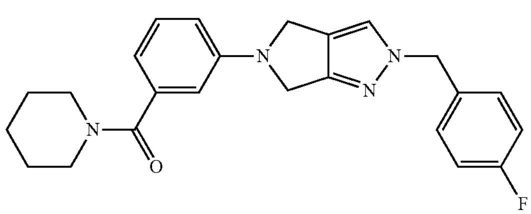 [SMILES: O=C(c1cccc(N2Cc3cn(Cc4ccc(F)cc4)nc3C2)c1)N1CCCCC1] | 79 |
| 243 | 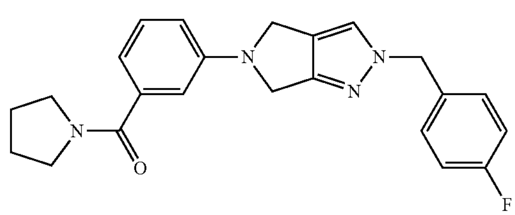 [SMILES: O=C(c1cccc(N2Cc3cn(Cc4ccc(F)cc4)nc3C2)c1)N1CCCC1] | 1149 |

TABLE 1-continued

Inhibition of AMPA-mediated neurotoxicity

| Compound | Structure | Potency (nM) |
|---|---|---|
| 244 | (structure) | 2.4 |
| 245 | (structure) | 771 |
| 246 | (structure) | 8.6 |
| 247 | (structure) | 36 |

The above data demonstrates that certain 2-pyrrolopyrazoles are highly potent inhibitors of the AMPA-mediated neurotoxicity. The data also demonstrate that the 2-pyrrolopyrazoles show a surprising and unexpected enhancement in potency compared to the 1-pyrrolopyrazole reference compound, denoted in the table with "REF".

In Vitro Studies—Surface Plasmon Resonance Target Engagement Assay

This is one of the most commonly used techniques to study modulation of protein-protein interactions by small molecule ligands, providing real-time measurement of binding affinities and association/dissociation kinetics of complexes (compound/protein) in a label-free environment. The ability of our lead compound to disrupt the interaction of GluR2/GAPDH complex was measured by the binding affinity. Compounds were analyzed for competitive GluR2-Venus protein affinity (with GAPDH recombinant protein) using a Reichert 2SPR system. The surface was first charged with nickel (500 μM $NiCl_2$ in HBS-P buffer for 300 s at a flow rate of 5 μL/min). The dextran surface was then activated with a 1:1 mixture of N-ethyl-N-dimethylamino-propylcarbodiimide (EDC) and N-hydroxysuccinimide (NHS) on line for final concentrations of EDC and NHS of 37.5 mg/mL and 5.8 mg/mL, respectively, for 420 s at a flow rate of 25 μL/min. Anti-VENUS antibody was first immobilized by capture onto a 500 KDa CM Dextran sensor chip (Reichert), proceeded by activation of the carboxymethylated dextran surface for mild amine coupling, followed by a final blocking injection of 1 M ethanolamine, pH 8.5. GluR2-VENUS (lysate of HEK293 cells stably transfected with GluR2-VENUS) was then captured for 900 s at a flow rate of 25 μL/min followed by a final blocking injection of 2% BSA, for 300 s at a flow rate of 5 μL/min.

The surface plasmon resonance affinity assay was carried out in a PBS buffer consisting of 0.05% Tween 20. For affinity measurements, compound solutions were prepared using ten three-fold serial dilutions in running buffer from a 10 μM top concentration (prepared from DMSO stocks) along with a zero (running buffer) control, mixed with 100 nM GAPDH peptide (Sigma Aldrich). A flow rate of 30 μl/min was used with a 420 s contact time (using high performance injection parameters) followed by a 120 s dissociation phase. Results were analyzed by subtracting the signals of the reference surface from the signals for the protein-bound surfaces and performing a solvent correction. Competitive binding responses were normalized throughout the screen to the percentage of inhibition of the respective small molecule compound. Three independent experiments were performed.

Biological Study 2

The binding affinity was measured using the surface plasmon resonance assay described above. The results are summarized in Table 2.

TABLE 2

GluR2 Binding Affinity

| Compound | Structure | Potency (nM) |
|---|---|---|
| REF | 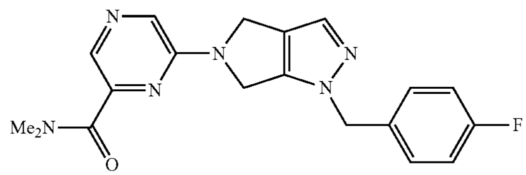 | >1000 |
| 155 | 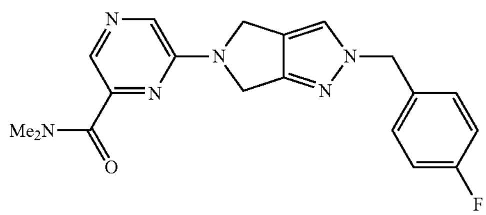 | 0.4 |
| 209 | 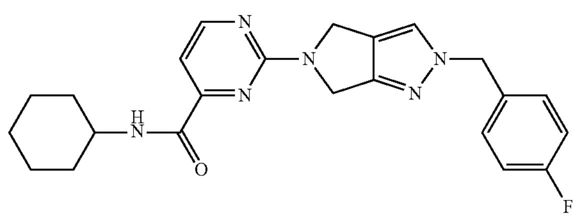 [SMILES: O=C(NC1CCCCC1)c1ccnc(N2Cc3cn(Cc4ccc(F)cc4)nc3C2)n1] | 99 |
| 210 | 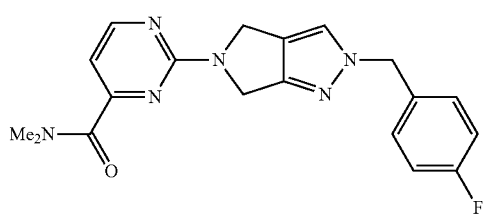 [SMILES: CN(C)C(=O)c1ccnc(N2Cc3cn(Cc4ccc(F)cc4)nc3C2)n1] | 33 |
| 211 | 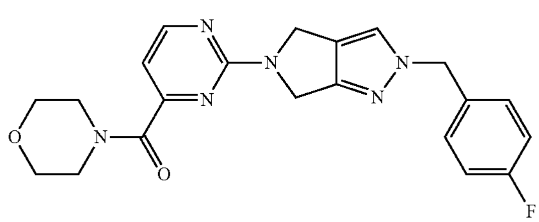 [SMILES: O=C(c1ccnc(N2Cc3cn(Cc4ccc(F)cc4)nc3C2)n1)N1CCOCC1] | 34 |
| 212 | 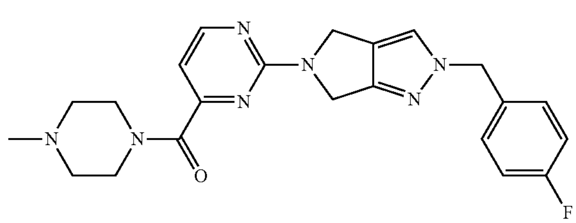 [SMILES: CN1CCN(C(=O)c2ccnc(N3Cc4cn(Cc5ccc(F)cc5)nc4C3)n2)CC1] | 31 |

TABLE 2-continued
GluR2 Binding Affinity
| Compound | Structure | Potency (nM) |
|---|---|---|
| 213 | 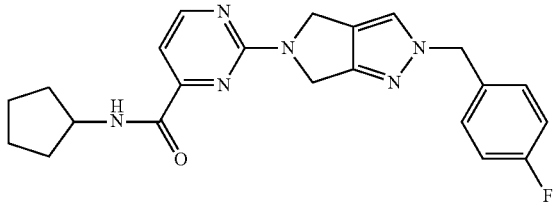 [SMILES: O=C(NC1CCCC1)c1ccnc(N2Cc3cn(Cc4ccc(F)cc4)nc3C2)n1] | 20 |
| 214 | 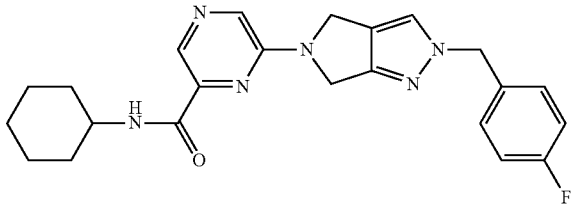 | 24 |
| 215 | 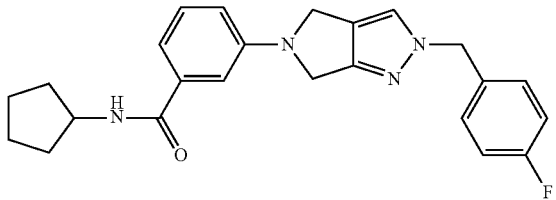 [SMILES: O=C(NC1CCCC1)c1cccc(N2Cc3cn(Cc4ccc(F)cc4)nc3C2)c1] | 48 |
| 216 | 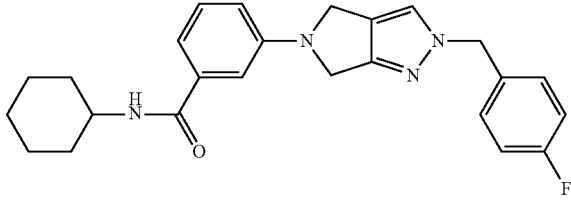 [SMILES: O=C(NC1CCCCC1)c1cccc(N2Cc3cn(Cc4ccc(F)cc4)nc3C2)c1] | 91 |
| 217 | 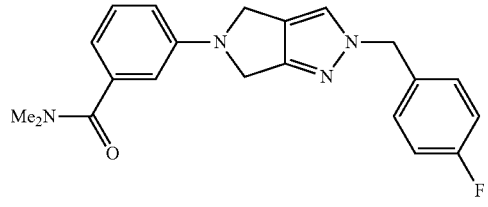 | 67 |
| 218 | 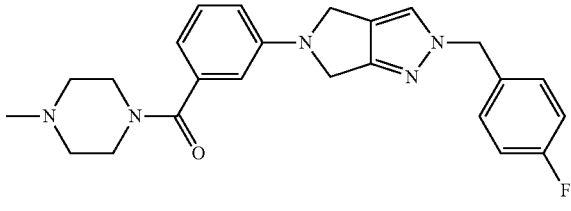 [SMILES: CN1CCN(C(=O)c2cccc(N3Cc4cn(Cc5ccc(F)cc5)nc4C3)c2)CC1] | 99 |
| 219 | 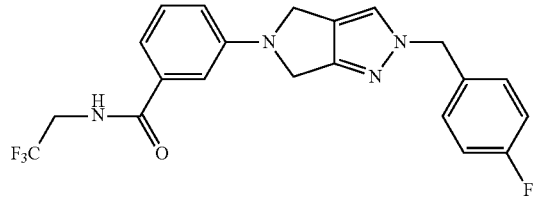 [SMILES: O=C(NCC(F)(F)F)c1cccc(N2Cc3cn(Cc4ccc(F)cc4)nc3C2)c1] | 14 |

TABLE 2-continued
GluR2 Binding Affinity
| Compound | Structure | Potency (nM) |
|---|---|---|
| 220 | 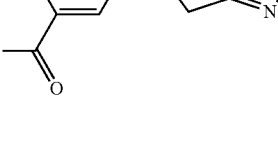 | 85 |
| 231 | 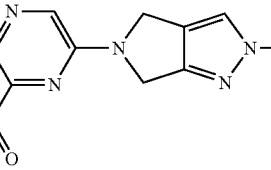 | 86 |
| 232 | 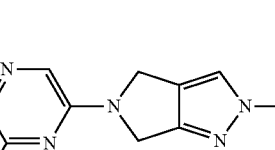 | 88 |
| 233 | 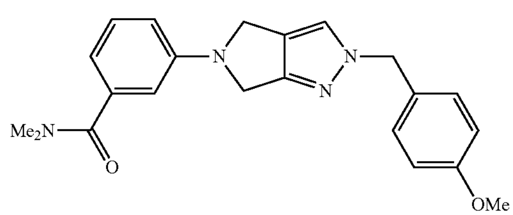 [SMILES: COc1ccc(Cn2cc3c(n2)CN(c2cccc(C(=O)N(C)C)c2)C3)cc1] | 33 |
| 234 | 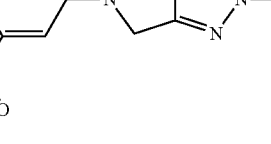 | 139 |
| 235 | 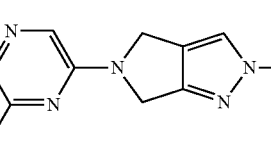 | 1073 |
| 236 | 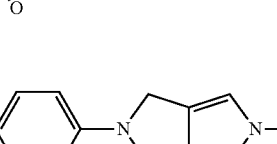 | 275 (wide) |

TABLE 2-continued

| GluR2 Binding Affinity | | |
|---|---|---|
| Compound | Structure | Potency (nM) |
| 237 | | 30 |
| 238 | | 102 |
| 239 | | 41 |
| 240 | | 26 |
| 241 | | 20 |
| 242 | | 8 |
| 243 | | 130 |

TABLE 2-continued

GluR2 Binding Affinity

| Compound | Structure | Potency (nM) |
|---|---|---|
| 244 | 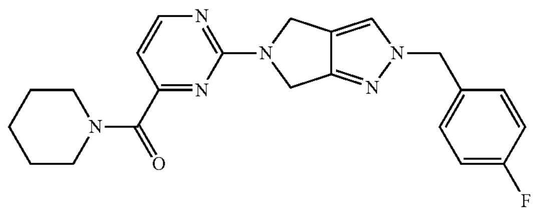 [SMILES: O=C(c1ccnc(N2Cc3cn(Cc4ccc(F)cc4)nc3C2)n1)N1CCCCC1] | 2.4 |
| 245 | 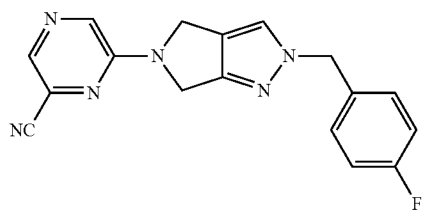 [SMILES: N#Cc1cncc(N2Cc3cn(Cc4ccc(F)cc4)nc3C2)n1] | 206 |
| 246 | 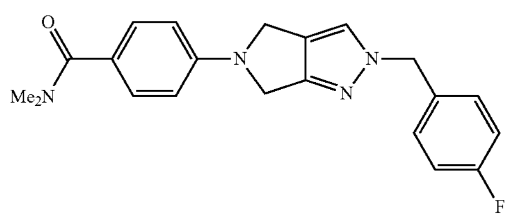 [SMILES: CN(C)C(=O)c1ccc(N2Cc3cn(Cc4ccc(F)cc4)nc3C2)cc1] | 440 |
| 247 | 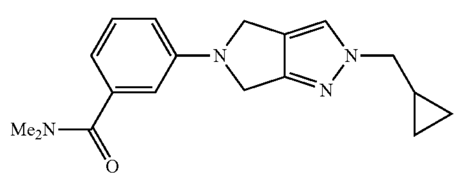 [SMILES: CN(C)C(=O)c1cccc(N2Cc3cn(CC4CC4)nc3C2)c1] | 148 |

The above data demonstrates that certain 2-pyrrolopyrazoles are highly potent competitive inhibitors of the Glu R2-GAPDH interaction and that 2-pyrrolopyrazoles show a surprising and unexpected enhancement in potency compared to the 1-pyrrolopyrazole reference compound.

In Vitro Studies—Human and Rat Liver Microsomal Stability Assays

Metabolic stability of 2-pyrrolopyrazoles derivatives was measured by determination of the rate of compound disappearance when incubated in the presence of human or rat liver microsomes. Liver microsomes are prepared from the endoplasmic reticulum of hepatocytes and are the primary source of the most important enzymes (cytochrome P450) involved in drug metabolism. Study of drug stability in the presence of liver microsomes is accepted as a valuable model permitting rapid prediction of in vivo drug stability.

Protocol Summary

Human or rat liver microsomes were obtained from a commercial source. Test compounds (3 µM) were incubated with pooled liver microsomes (male and female). Samples were incubated for a 45 minute period and removed at 5 time points and test compounds were analyzed by LC-MS/MS Microsomes (final protein concentration 0.5 mg/mL), 0.1 M phosphate buffer pH 7.4, and test compound (final concentration 3 µM; diluted from 10 mM stock solution to give a final DMSO concentration of 0.25%) were incubated at 37° C. prior to the addition of NADPH (final concentration 1 mM) to initiate the reaction. The final incubation volume was 25 µL. A control incubation was included for each compound tested, where 0.1 M phosphate buffer pH 7.4 was added instead of NADPH. The control compounds testosterone and 7-hydroxycoumarin were included in each experiment and all incubations were performed singularly for each compound.

Each compound was incubated for 0, 5, 15, 30, and 45 minutes. The control (minus NADPH) was incubated for 45 minutes only. The reactions were stopped by the addition of 50 µL methanol containing internal standard at the appropriate time points. The incubation plates were centrifuged at 2500 rpm for 20 minutes at 4° C. to precipitate the protein.

Quantitative Analysis:

Following protein precipitation, the sample supernatants were combined in cassettes of up to 4 compounds and analysed using standard LC-MS/MS conditions.

Data Analysis:

From a plot of the natural logarithm of the peak area ratio (i.e., the ratio of compound peak area: internal standard peak area) against time, the gradient of the line was determined. Subsequently, half-life and intrinsic clearance were calculated using the equations below:

Eliminated rate constant $(k)$=(−gradient).

Half-life $(t_{1/2})$ (min)=0.063/$k$.

Intrinsic Clearance $(CL_{int})$ (µL/min/million cells)= $(V \times 0.693)/t_{1/2}$.

wherein $V$=Incubation volume (µL/mg microsomal protein).

Biological Study 3

The metabolic stability of a number of 2-pyrrolopyrazoles was determined and compared with the metabolic stability of a range of structurally related compounds using the assay described previously.

Biological half-life values $(t_{1/2})$ were determined for several 2-pyrrolopyrazoles, as well as the closely-related reference 1-pyrrolopyrazole, using the human liver microsomal stability assay described above. The results are summarized in Tables 3 and 4.

TABLE 3

Human Liver Microsomal Stability Data

| Compound | Structure | T1/2 (min) |
|---|---|---|
| REF | 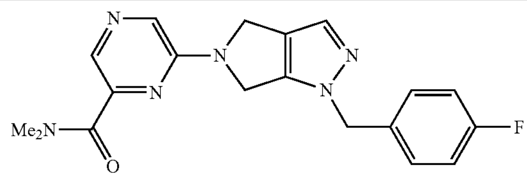 | 73 |
| 155 | 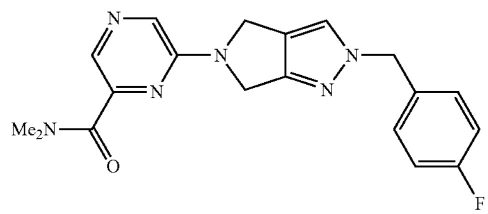 | 329 |
| 209 | 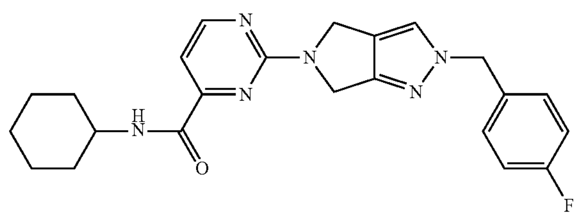 [SMILES: O=C(NC1CCCCC1)c1ccnc(N2Cc3cn(Cc4ccc(F)cc4)nc3C2)n1] | 13 |
| 210 | 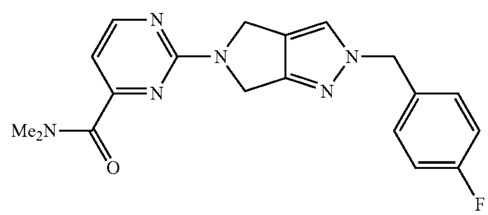 [SMILES: CN(C)C(=O)c1ccnc(N2Cc3cn(Cc4ccc(F)cc4)nc3C2)n1] | 749 |
| 211 | 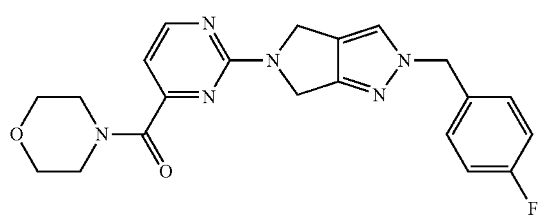 [SMILES: O=C(c1ccnc(N2Cc3cn(Cc4ccc(F)cc4)nc3C2)n1)N1CCOCC1] | 328 |
| 213 | 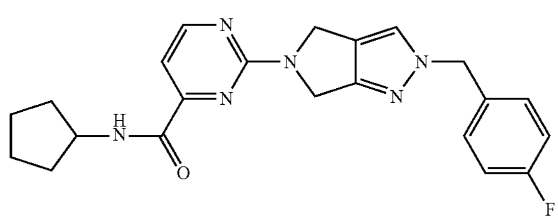 [SMILES: O=C(NC1CCCC1)c1ccnc(N2Cc3cn(Cc4ccc(F)cc4)nc3C2)n1] | 9 |

TABLE 3-continued

Human Liver Microsomal Stability Data

| Compound | Structure | T1/2 (min) |
|---|---|---|
| 216 | 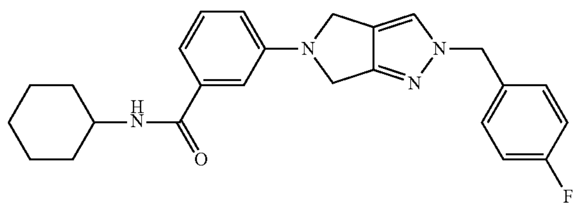 [SMILES: O=C(NC1CCCCC1)c1cccc(N2Cc3cn(Cc4ccc(F)cc4)nc3C2)c1] | >1000 |
| 217 | 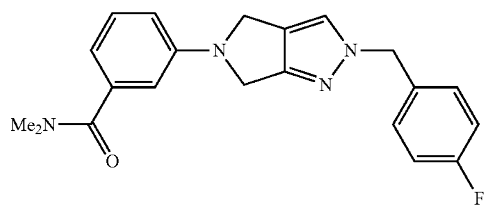 [SMILES: CN(C)C(=O)c1cccc(N2Cc3cn(Cc4ccc(F)cc4)nc3C2)c1] | 96 |
| 219 | 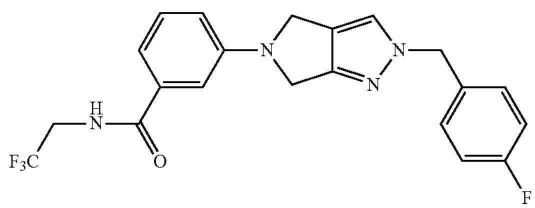 [SMILES: O=C(NCC(F)(F)F)c1cccc(N2Cc3cn(Cc4ccc(F)cc4)nc3C2)c1] | 366 |
| 220 | 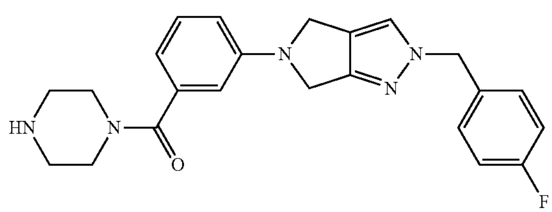 [SMILES: O=C(c1cccc(N2Cc3cn(Cc4ccc(F)cc4)nc3C2)c1)N1CCNCC1] | 226 |
| 226 | 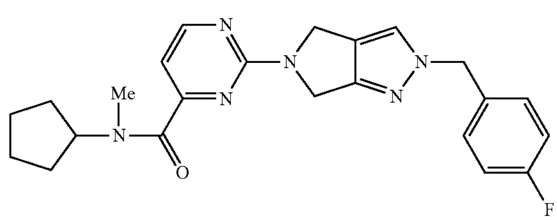 | 7 |
| 228 | 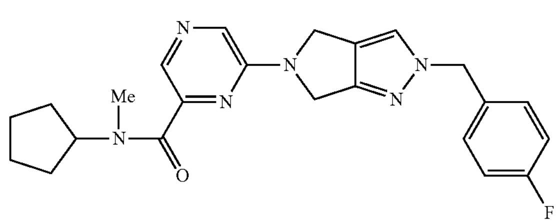 [SMILES: CN(C(=O)c1cncc(N2Cc3cn(Cc4ccc(F)cc4)nc3C2)n1)C1CCCC1] | 8 |
| 230 | 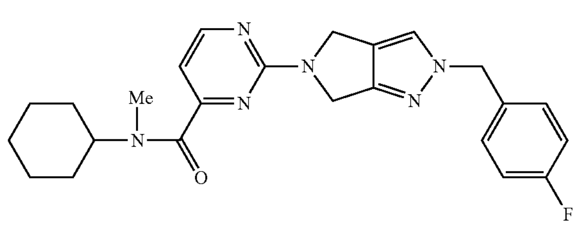 [SMILES: CN(C(=O)c1ccnc(N2Cc3cn(Cc4ccc(F)cc4)nc3C2)n1)C1CCCCC1] | 8 |

TABLE 3-continued

Human Liver Microsomal Stability Data

| Compound | Structure | T1/2 (min) |
|---|---|---|
| 237 | 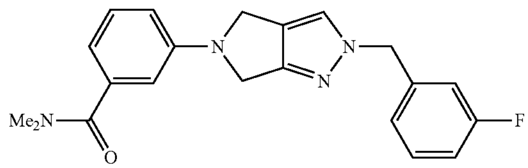 [SMILES: CN(C)C(=O)c1cccc(N2Cc3cn(Cc4cccc(F)c4)nc3C2)c1] | 100 |
| 239 | 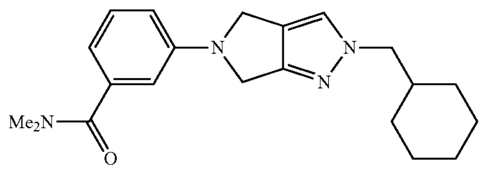 [SMILES: CN(C)C(=O)c1cccc(N2Cc3cn(CC4CCCCC4)nc3C2)c1] | 26 |
| 240 | 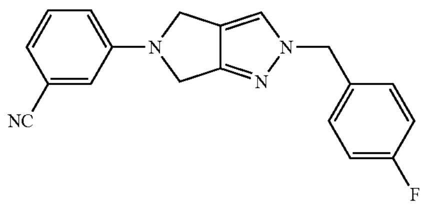 [SMILES: N#Cc1cccc(N2Cc3cn(Cc4ccc(F)cc4)nc3C2)c1] | 42 |
| 241 | 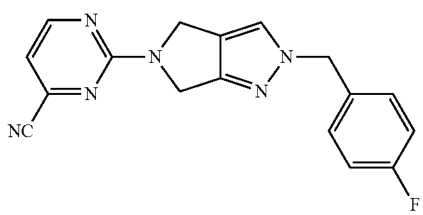 [SMILES: N#Cc1ccnc(N2Cc3cn(Cc4ccc(F)cc4)nc3C2)n1] | 51 |
| 242 | 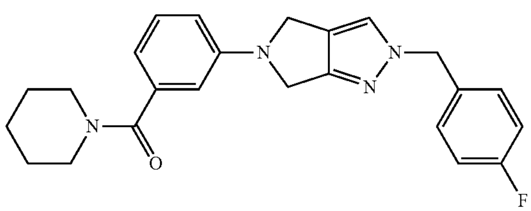 [SMILES: O=C(c1cccc(N2Cc3cn(Cc4ccc(F)cc4)nc3C2)c1)N1CCCCC1] | 18 |
| 244 | 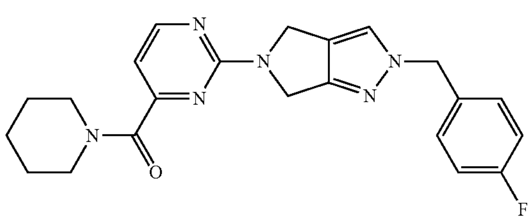 [SMILES: O=C(c1ccnc(N2Cc3cn(Cc4ccc(F)cc4)nc3C2)n1)N1CCCCC1] | 51 |
| 246 | 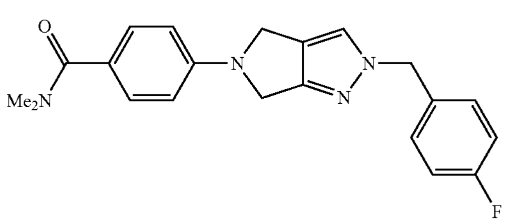 [SMILES: CN(C)C(=O)c1ccc(N2Cc3cn(Cc4ccc(F)cc4)nc3C2)cc1] | 36 |

The above data demonstrate that 2-pyrrolopyrazoles can show considerable improvements in metabolic stability compared to a closely-related 1-pyrrolopyrazole. However, the data also demonstrate that the metabolic stability is not predictable, as not all derivatives show enhanced stability.

TABLE 4

| Compound | Structure | T1/2 (min) |
|---|---|---|
| REF | 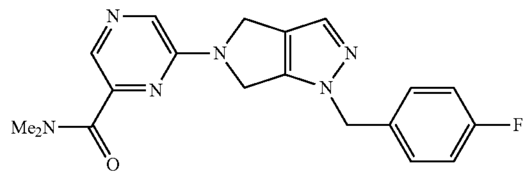 | 37 |
| 155 | 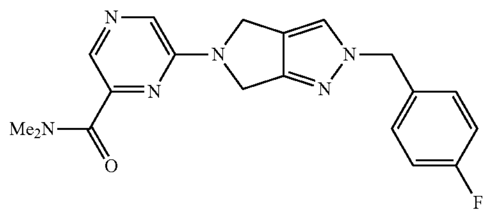 | 309 |
| 209 | 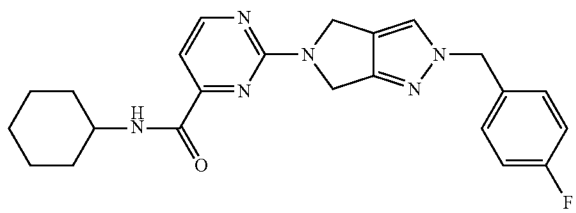 [SMILES: O=C(NC1CCCCC1)c1ccnc(N2Cc3cn(Cc4ccc(F)cc4)nc3C2)n1] | 3.5 |
| 210 | 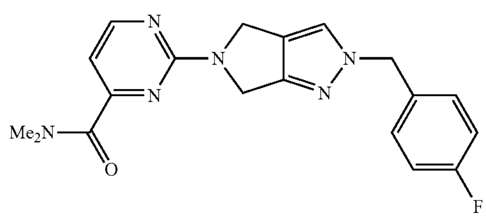 [SMILES: CN(C)C(=O)c1ccnc(N2Cc3cn(Cc4ccc(F)cc4)nc3C2)n1] | 158 |
| 211 | 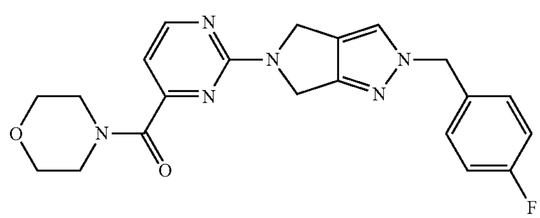 [SMILES: O=C(c1ccnc(N2Cc3cn(Cc4ccc(F)cc4)nc3C2)n1)N1CCOCC1] | 107 |
| 213 | 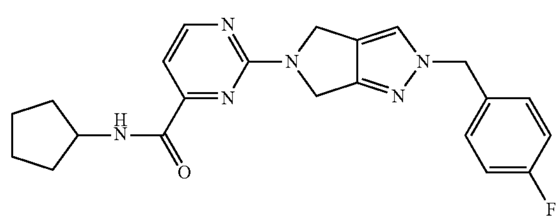 [SMILES: O=C(NC1CCCC1)c1ccnc(N2Cc3cn(Cc4ccc(F)cc4)nc3C2)n1] | 7 |
| 216 | 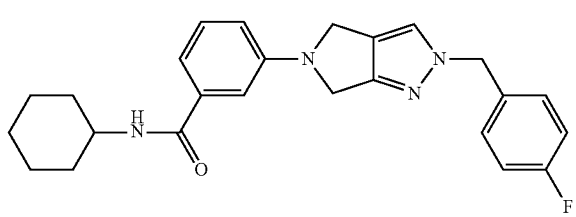 [SMILES: O=C(NC1CCCCC1)c1cccc(N2Cc3cn(Cc4ccc(F)cc4)nc3C2)c1] | 309 |

TABLE 4-continued

Rat Liver Microsomal Stability Data

| Compound | Structure | T1/2 (min) |
|---|---|---|
| 217 | 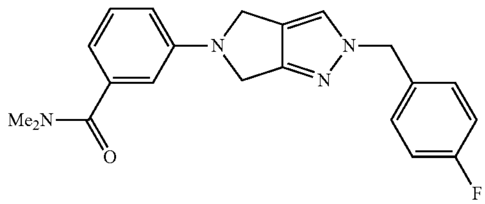 [SMILES: CN(C)C(=O)c1cccc(N2Cc3cn(Cc4ccc(F)cc4)nc3C2)c1] | 154 |
| 219 | 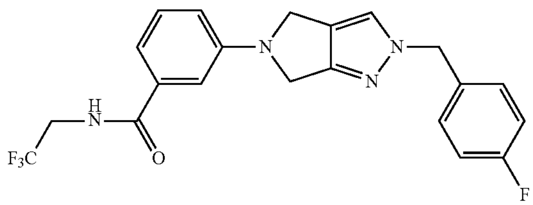 [SMILES: O=C(NCC(F)(F)F)c1cccc(N2Cc3cn(Cc4ccc(F)cc4)nc3C2)c1] | 92 |
| 220 | 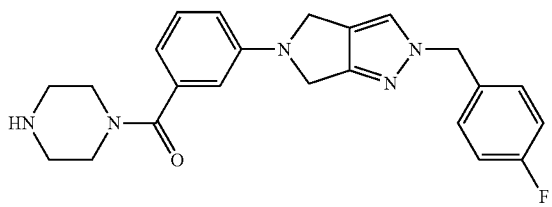 [SMILES: O=C(c1cccc(N2Cc3cn(Cc4ccc(F)cc4)nc3C2)c1)N1CCNCC1] | 13 |
| 226 | 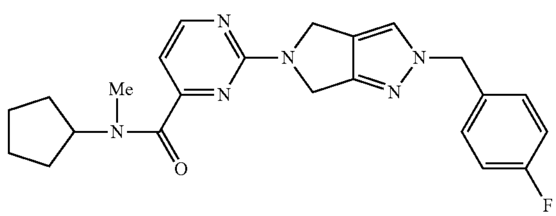 [SMILES: CN(C(=O)c1ccnc(N2Cc3cn(Cc4ccc(F)cc4)nc3C2)n1)C1CCCC1] | <1 |
| 228 | 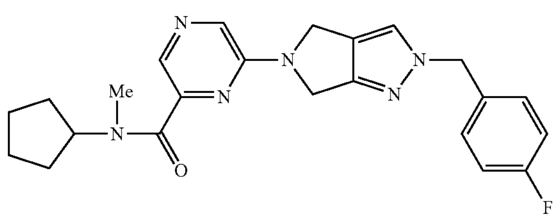 [SMILES: CN(C(=O)c1cncc(N2Cc3cn(Cc4ccc(F)cc4)nc3C2)n1)C1CCCC1] | <1 |
| 230 | 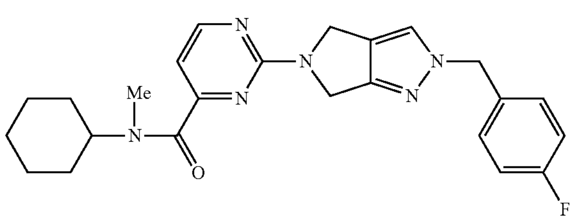 [SMILES: CN(C(=O)c1ccnc(N2Cc3cn(Cc4ccc(F)cc4)nc3C2)n1)C1CCCCC1] | <1 |
| 237 | 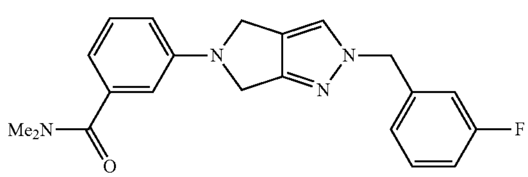 [SMILES: CN(C)C(=O)c1cccc(N2Cc3cn(Cc4cccc(F)c4)nc3C2)c1] | 48 |

TABLE 4-continued
Rat Liver Microsomal Stability Data
| Compound | Structure | T1/2 (min) |
|---|---|---|
| 239 | 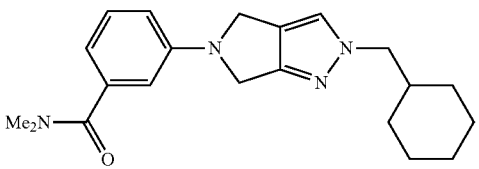 | 1.4 |
| 240 | 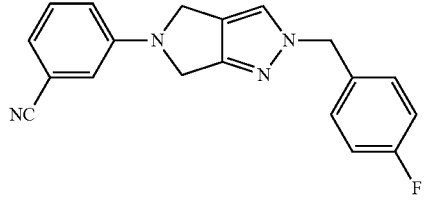 [SMILES: N#Cc1cccc(N2Cc3cn(Cc4ccc(F)cc4)nc3C2)c1] | 1.4 |
| 241 | 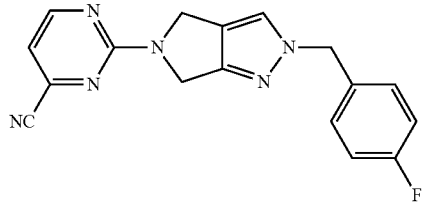 [SMILES: N#Cc1ccnc(N2Cc3cn(Cc4ccc(F)cc4)nc3C2)n1] | 1.7 |
| 242 | 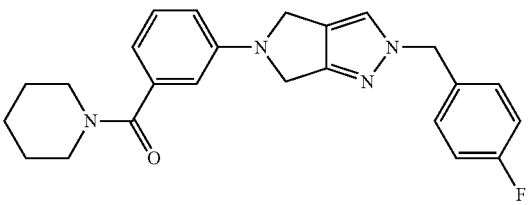 [SMILES: O=C(c1cccc(N2Cc3cn(Cc4ccc(F)cc4)nc3C2)c1)N1CCCCC1] | 14 |
| 244 | 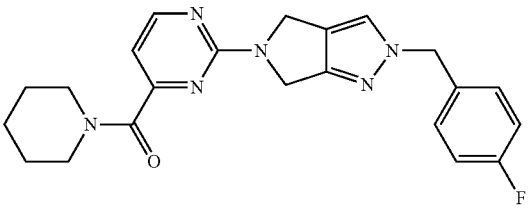 [SMILES: O=C(c1ccnc(N2Cc3cn(Cc4ccc(F)cc4)nc3C2)n1)N1CCCCC1] | 19 |
| 246 | 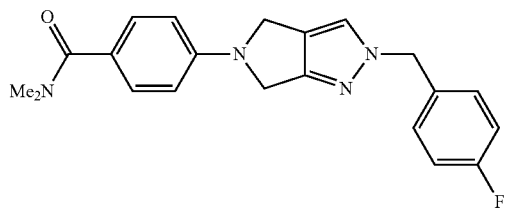 [SMILES: CN(C)C(=O)c1ccc(N2Cc3cn(Cc4ccc(F)cc4)nc3C2)cc1] | 49 |

The above data demonstrate that 2-pyrrolopyrazoles can show considerable improvements in metabolic stability compared to a closely-related 1-pyrrolopyrazole. However, the data also demonstrate that the metabolic stability is not predictable, as not all derivatives show enhanced stability.

What is claimed is:

1. A compound of Formula (Ia)

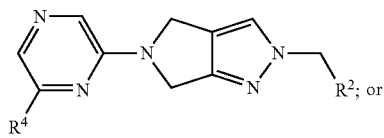

(Ia)

Formula (Ib)

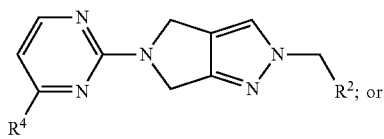

(Ib)

Formula (Ic)

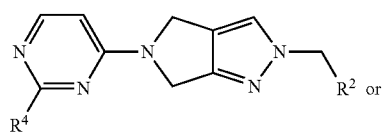

(Ic)

Formula (Id)

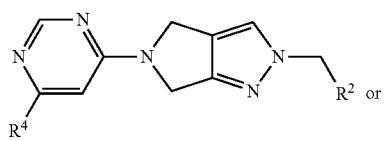

(Id)

Formula (Ie)

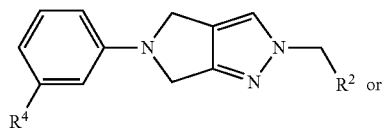

(Ie)

Formula (If)

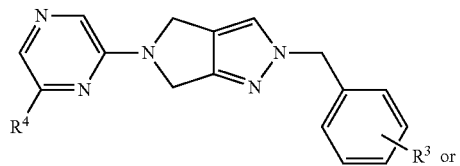

(If)

Formula (Ig)

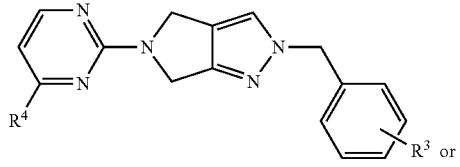

(Ig)

Formula (Ih)

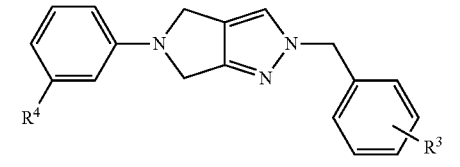

(Ih)

wherein
R² is $(C_3-C_{10})$-cycloalkyl, $(C_3-C_{10})$-heterocycloalkyl, $(C_6-C_{10})$-aryl or $(C_5-C_{10})$-heteroaryl, each of which is optionally substituted with one to three R³;
R³ is halo, —CF₃, —OCF₃, —CN, —NO₂, —R$^d$, —OR$^d$, —SR$^d$, or —NR$^d$R$^e$, wherein R$^d$ and R$^e$ are independently H or $(C_1-C_6)$-alkyl; and
R⁴ is CN or —C(=O)NR$^a$R$^b$, wherein R$^a$ and R$^b$ are independently H, $(C_1-C_6)$-alkyl or $(C_3-C_6)$-cycloalkyl.

2. The compound of claim 1, wherein R³ is halo.
3. The compound of claim 1, wherein R³ is F or Cl.
4. A compound of claim 1, wherein said compound is

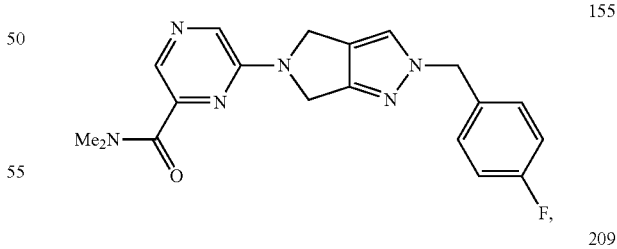

155

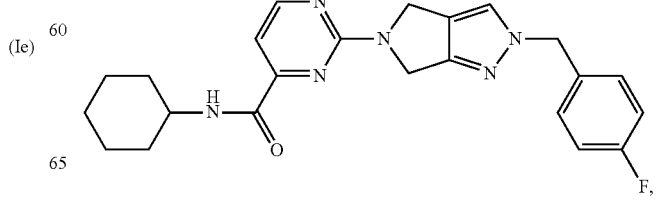

209

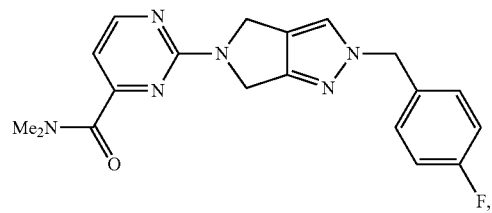
210
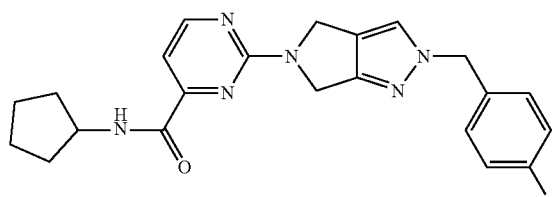
213
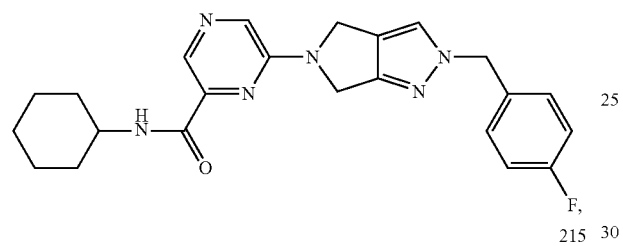
214
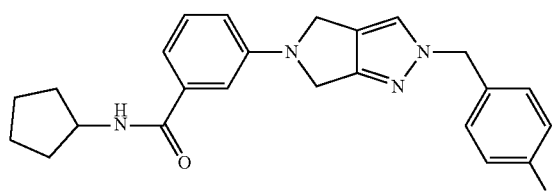
215
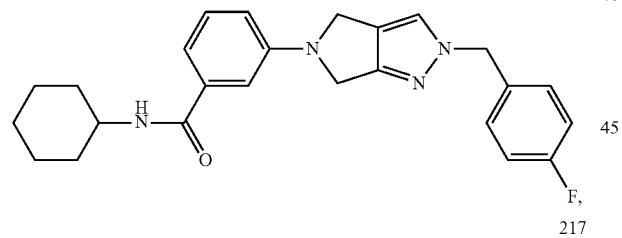
216
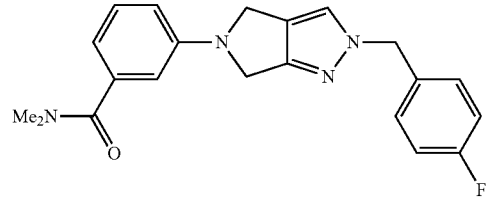
217
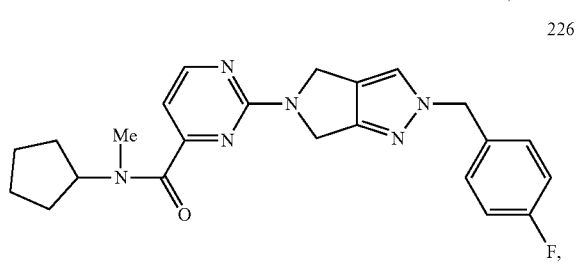
226
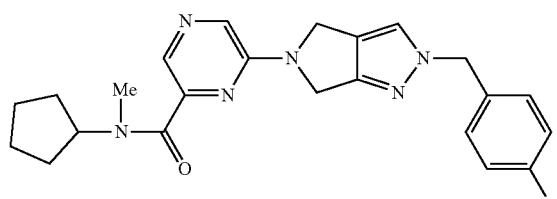
228
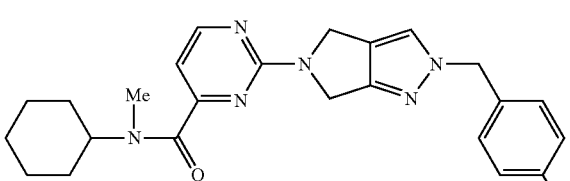
230
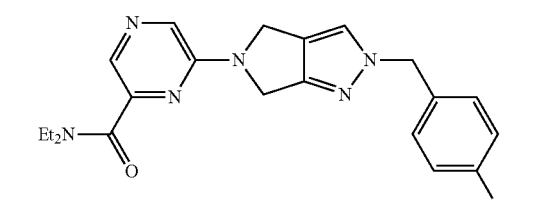
231
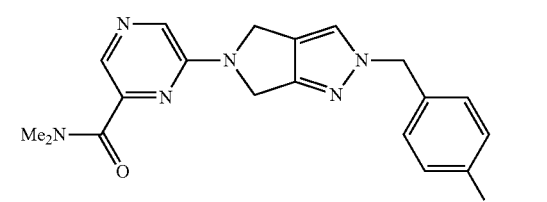
232
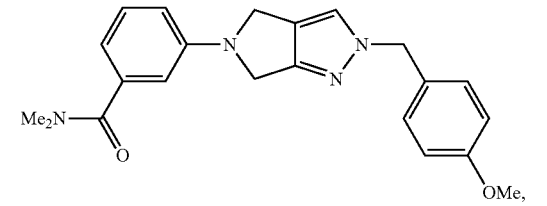
233
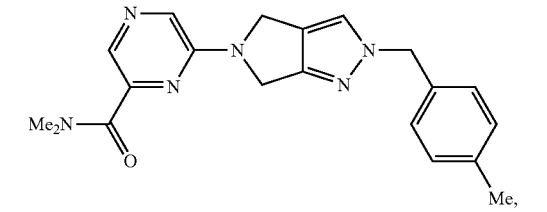
234
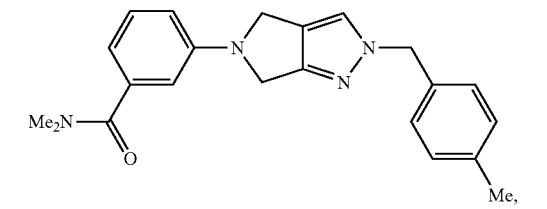
235

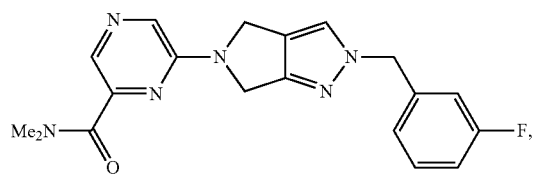
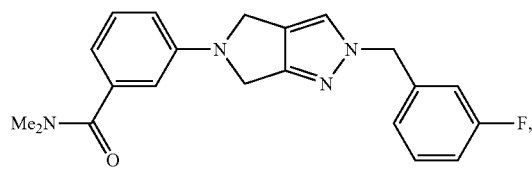
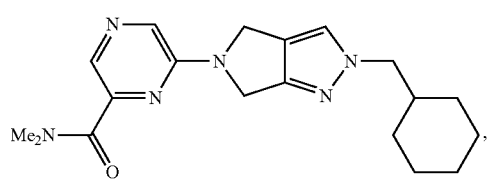
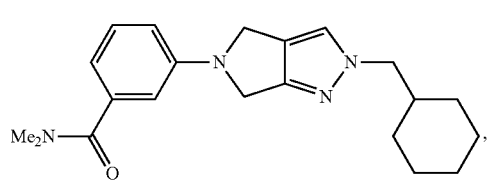
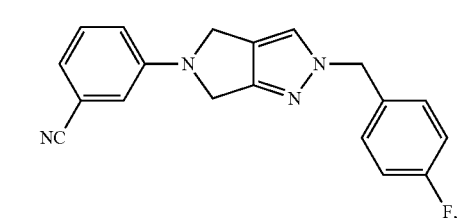
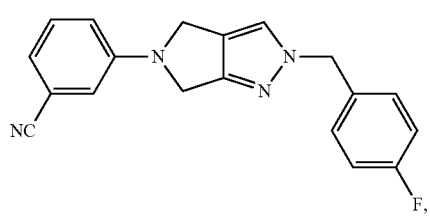
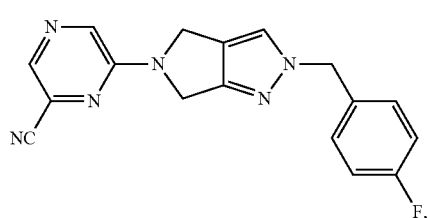
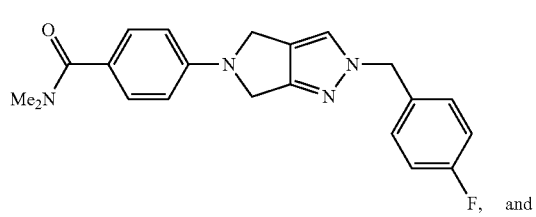
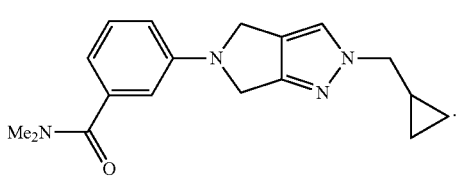
5. A pharmaceutical composition comprising a compound of claim 4, or a pharmaceutically acceptable salt thereof, and a pharmaceutically acceptable carrier.
6. A pharmaceutical composition comprising a compound of claim 1, or a pharmaceutically acceptable salt thereof, and a pharmaceutically acceptable carrier.
7. A compound selected from the group consisting of
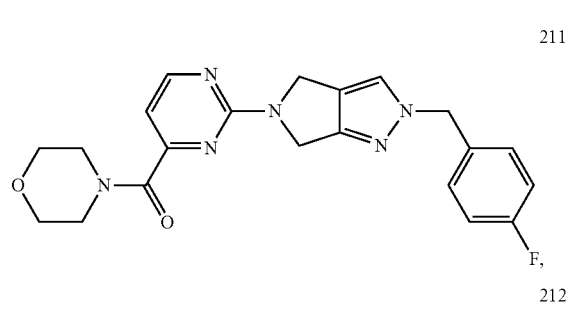
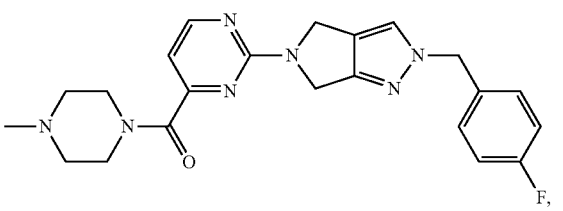
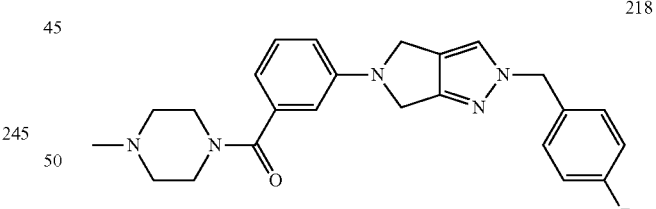
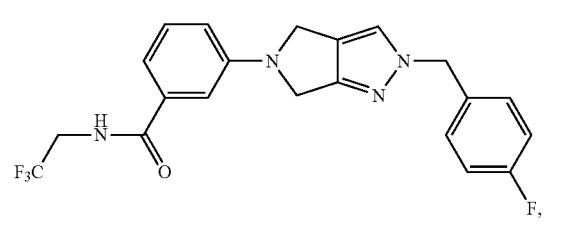

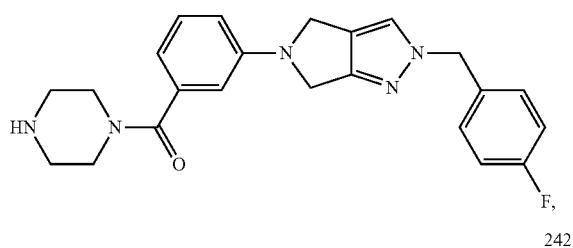

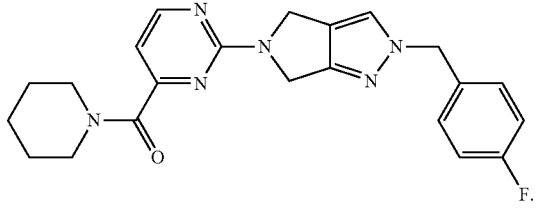

8. A pharmaceutical composition comprising a compound of claim 7, or a pharmaceutically acceptable salt thereof, and a pharmaceutically acceptable carrier.

9. A method of ameliorating or alleviating one or more symptoms of a neurological disease or disorder selected from neuroinflammation, amyotrophic lateral sclerosis (ALS), multiple sclerosis (MS), stroke, and epilepsy, the method comprising administering an effective amount of the compound of claim 1, or a pharmaceutical composition comprising the compound of claim 1, to a human subject in need thereof.

10. The method of claim 9, wherein the neurological disease or disorder is characterized by excessive glutamate receptor-mediated excitotoxicity.

11. A method of ameliorating or alleviating one or more symptoms of a neurological disease or disorder selected from neuroinflammation, amyotrophic lateral sclerosis (ALS), multiple sclerosis (MS), stroke, and epilepsy, the method comprising administering an effective amount of a compound of claim 4, or a pharmaceutical composition comprising a compound of claim 4, to a human subject in need thereof.

* * * * *